United States Patent
Tamarkin et al.

(10) Patent No.: US 10,117,812 B2
(45) Date of Patent: *Nov. 6, 2018

(54) FOAMABLE COMPOSITION COMBINING A POLAR SOLVENT AND A HYDROPHOBIC CARRIER

(75) Inventors: Dov Tamarkin, Maccabim (IL); Doron Friedman, Karmei Yosef (IL); Meir Eini, Ness Ziona (IL); Alex Besonov, Rehovot (IL)

(73) Assignee: Foamix Pharmaceuticals Ltd., Rehovot (IL)

( * ) Notice: Subject to any disclaimer, the term of this patent is extended or adjusted under 35 U.S.C. 154(b) by 1479 days.

This patent is subject to a terminal disclaimer.

(21) Appl. No.: 11/488,989

(22) Filed: Jul. 19, 2006

(65) Prior Publication Data

US 2007/0020213 A1     Jan. 25, 2007

Related U.S. Application Data

(63) Continuation-in-part of application No. 10/835,505, filed on Apr. 28, 2004, now Pat. No. 7,820,145, and a continuation-in-part of application No. 10/911,367, filed on Aug. 4, 2004, now abandoned, and a continuation-in-part of application No. 10/922,358, filed on Aug. 20, 2004, now Pat. No. 7,700,076, and a continuation-in-part of application No. 11/124,676, filed on May 9, 2005, now abandoned, which is a continuation of application No. 10/532,618, filed as application No. PCT/IB03/05527 on Oct. 24, 2003, now abandoned.

(60) Provisional application No. 60/429,546, filed on Nov. 29, 2002, provisional application No. 60/492,385, filed on Aug. 4, 2003, provisional application No. 60/497,648, filed on Aug. 25, 2003, provisional
(Continued)

(51) Int. Cl.
| | |
|---|---|
| A61K 8/04 | (2006.01) |
| A61K 47/14 | (2017.01) |
| A61K 47/22 | (2006.01) |
| A61K 8/49 | (2006.01) |
| A61K 8/06 | (2006.01) |
| A61K 8/31 | (2006.01) |
| A61K 8/37 | (2006.01) |
| A61K 9/00 | (2006.01) |
| A61K 9/107 | (2006.01) |
| A61K 9/12 | (2006.01) |
| A61Q 19/00 | (2006.01) |
| A01N 25/16 | (2006.01) |
| A61K 8/96 | (2006.01) |
| A61K 35/04 | (2006.01) |
| A61K 47/06 | (2006.01) |
| A61K 47/10 | (2017.01) |
| A61K 8/73 | (2006.01) |
| A61K 8/81 | (2006.01) |
| A61K 47/32 | (2006.01) |
| A61K 47/38 | (2006.01) |
| A61Q 19/02 | (2006.01) |
| A61Q 19/08 | (2006.01) |

(52) U.S. Cl.
CPC .............. *A61K 8/046* (2013.01); *A01N 25/16* (2013.01); *A61K 8/062* (2013.01); *A61K 8/31* (2013.01); *A61K 8/37* (2013.01); *A61K 8/375* (2013.01); *A61K 8/4973* (2013.01); *A61K 8/731* (2013.01); *A61K 8/8176* (2013.01); *A61K 8/965* (2013.01); *A61K 9/0014* (2013.01); *A61K 9/107* (2013.01); *A61K 9/122* (2013.01); *A61K 35/04* (2013.01); *A61K 47/06* (2013.01); *A61K 47/10* (2013.01); *A61K 47/14* (2013.01); *A61K 47/22* (2013.01); *A61K 47/32* (2013.01); *A61K 47/38* (2013.01); *A61Q 19/00* (2013.01); *A61Q 19/02* (2013.01); *A61Q 19/08* (2013.01)

(58) Field of Classification Search
None
See application file for complete search history.

(56) References Cited

U.S. PATENT DOCUMENTS

| 1,159,250 A | 11/1915 | Moulton |
| 1,666,684 A | 4/1928 | Carstens |

(Continued)

FOREIGN PATENT DOCUMENTS

| AU | 198780257 | 9/1986 |
| AU | 782515 | 12/2005 |

(Continued)

OTHER PUBLICATIONS

Machine translation of JP-08165218 (1996).*
(Continued)

*Primary Examiner* — Kevin S Orwig
*Assistant Examiner* — Barbara S Frazier
(74) *Attorney, Agent, or Firm* — Finnegan, Henderson, Farabow, Garrett & Dunner, LLP

(57) ABSTRACT

The present invention relates to a foamable vehicle or cosmetic or pharmaceutical composition, comprising: (1) an organic carrier, at a concentration of 10% to 70% by weight, wherein said organic carrier concurrently comprises: (i) at least one hydrophobic organic carrier, and (ii) at least one polar solvent; (2) at least one surface-active agent; (3) water; and (4) at least one liquefied or compressed gas propellant at a concentration of 3% to 25% by weight of the total composition.

The present invention further provides a method of treating, alleviating or preventing a disorder of mammalian subject, comprising administering the above-mentioned compositions to an afflicted target site.

67 Claims, No Drawings

Related U.S. Application Data application No. 60/530,015, filed on Dec. 16, 2003, provisional application No. 60/700,702, filed on Jul. 19, 2005.

(56) References Cited

U.S. PATENT DOCUMENTS

| | | |
|---|---|---|
| 1,924,972 A | 8/1933 | Beckert |
| 2,085,733 A | 7/1937 | Bird |
| 2,390,921 A | 12/1945 | Clark |
| 2,524,590 A | 10/1950 | Boe |
| 2,586,287 A | 2/1952 | Apperson |
| 2,617,754 A | 11/1952 | Neely |
| 2,767,712 A | 10/1956 | Waterman |
| 2,968,628 A | 1/1961 | Reed |
| 3,004,894 A | 10/1961 | Johnson et al. |
| 3,062,715 A | 11/1962 | Reese |
| 3,067,784 A | 12/1962 | Gorman |
| 3,092,255 A | 6/1963 | Hohman |
| 3,092,555 A | 6/1963 | Horn |
| 3,141,821 A | 7/1964 | Compeau |
| 3,142,420 A | 7/1964 | Gawthrop |
| 3,144,386 A | 8/1964 | Brighttenback |
| 3,149,543 A | 9/1964 | Naab |
| 3,154,075 A | 10/1964 | Weckesser |
| 3,178,352 A | 4/1965 | Erickson |
| 3,236,457 A | 2/1966 | Kennedy et al. |
| 3,244,589 A | 4/1966 | Sunnen |
| 3,252,859 A | 5/1966 | Silver |
| 3,261,695 A | 7/1966 | Sienciewicz |
| 3,263,867 A | 8/1966 | Lehmann |
| 3,263,869 A | 8/1966 | Corsette |
| 3,298,919 A | 1/1967 | Charles et al. |
| 3,301,444 A | 1/1967 | Wittke |
| 3,303,970 A | 2/1967 | Breslau et al. |
| 3,330,730 A | 7/1967 | Hernaadez |
| 3,333,333 A | 8/1967 | Noack |
| 3,334,147 A | 8/1967 | Brunelle et al. |
| 3,342,845 A | 9/1967 | Sayigh et al. |
| 3,346,451 A | 10/1967 | Collins et al. |
| 3,366,494 A | 1/1968 | Bower |
| 3,369,034 A | 2/1968 | Chalmers |
| 3,377,004 A | 4/1968 | Wittke |
| 3,383,280 A | 5/1968 | Kuehns |
| 3,384,541 A | 5/1968 | Clark et al. |
| 3,395,214 A | 7/1968 | Mummert |
| 3,395,215 A | 7/1968 | Warren |
| 3,401,849 A | 9/1968 | Weber, III |
| 3,419,658 A | 12/1968 | Amsdon |
| 3,456,052 A | 7/1969 | Gordon |
| 3,527,559 A | 9/1970 | Sliwinski |
| 3,540,448 A | 11/1970 | Sunnen |
| 3,559,890 A | 2/1971 | Brooks et al. |
| 3,561,262 A | 2/1971 | Borocki |
| 3,563,098 A | 2/1971 | Weber, III |
| 3,574,821 A | 4/1971 | Pfirrmann |
| 3,577,518 A | 5/1971 | Shepherd |
| 3,667,461 A | 6/1972 | Zamarra |
| 3,751,562 A | 8/1973 | Nichols |
| 3,770,648 A | 11/1973 | Mackes |
| 3,787,566 A | 1/1974 | Gauvreau |
| 3,819,524 A | 6/1974 | Schubert et al. |
| 3,824,303 A | 7/1974 | Lanzet et al. |
| 3,841,525 A | 10/1974 | Siegel |
| 3,849,569 A | 11/1974 | Mead |
| 3,849,580 A | 11/1974 | Weinstein et al. |
| 3,865,275 A | 2/1975 | De Nunzio |
| 3,866,800 A | 2/1975 | Schmitt |
| 3,878,118 A | 4/1975 | Watson |
| 3,882,228 A | 5/1975 | Boncey et al. |
| 3,886,084 A | 5/1975 | Vassiliades |
| 3,890,305 A | 6/1975 | Weber et al. |
| 3,912,665 A | 10/1975 | Spitzer et al. |
| 3,912,667 A | 10/1975 | Spitzer et al. |
| 3,923,970 A | 12/1975 | Breuer |
| 3,929,985 A | 12/1975 | Webb, Jr. |
| 3,952,916 A | 4/1976 | Phillips |
| 3,953,591 A | 4/1976 | Snyder |
| 3,959,160 A | 5/1976 | Horsler et al. |
| 3,962,150 A | 6/1976 | Viola |
| 3,963,833 A | 6/1976 | DeSalva et al. |
| 3,966,090 A | 6/1976 | Prussin et al. |
| 3,966,632 A | 6/1976 | Colliopoulos et al. |
| 3,970,219 A | 7/1976 | Spitzer et al. |
| 3,970,584 A | 7/1976 | Hart et al. |
| 3,993,224 A | 11/1976 | Harrison |
| 3,997,467 A | 12/1976 | Jederstrom et al. |
| 4,001,391 A | 1/1977 | Feinstone et al. |
| 4,001,442 A | 1/1977 | Stahlberger et al. |
| 4,018,396 A | 4/1977 | Showmaker et al. |
| 4,019,657 A | 4/1977 | Spitzer et al. |
| 4,052,513 A | 10/1977 | Kaplan |
| 4,083,974 A | 4/1978 | Turi |
| 4,100,426 A | 7/1978 | Baranowski et al. |
| 4,102,995 A | 7/1978 | Hebborn |
| 4,110,426 A | 8/1978 | Barnhurst et al. |
| 4,124,149 A | 11/1978 | Spitzer et al. |
| 4,145,411 A | 3/1979 | Mende |
| 4,151,272 A | 4/1979 | Geary et al. |
| 4,160,827 A | 7/1979 | Cho et al. |
| 4,178,373 A | 12/1979 | Klein et al. |
| 4,213,979 A | 7/1980 | Levine |
| 4,214,000 A | 7/1980 | Papa |
| 4,226,344 A | 10/1980 | Booth et al. |
| 4,229,432 A | 10/1980 | Geria |
| 4,230,701 A | 10/1980 | Holick et al. |
| 4,241,048 A | 12/1980 | Durbak et al. |
| 4,241,149 A | 12/1980 | Labes et al. |
| 4,252,787 A | 2/1981 | Sherman et al. |
| 4,254,104 A | 3/1981 | Suzuki et al. |
| 4,268,499 A | 5/1981 | Keil |
| 4,271,149 A | 6/1981 | Winicov et al. |
| 4,278,206 A | 7/1981 | Prussin |
| 4,292,250 A | 9/1981 | DeLuca et al. |
| 4,292,326 A | 9/1981 | Nazzaro-Porro et al. |
| 4,299,826 A | 11/1981 | Luedders |
| 4,305,936 A | 12/1981 | Klein |
| 4,309,995 A | 1/1982 | Sacco |
| 4,310,510 A | 1/1982 | Sherman et al. |
| 4,323,582 A | 4/1982 | Siegel et al. |
| 4,323,694 A | 4/1982 | Scala, Jr. |
| 4,325,939 A | 4/1982 | Shah |
| 4,329,990 A | 5/1982 | Sneider |
| 4,335,120 A | 6/1982 | Holick et al. |
| 4,338,211 A | 7/1982 | Stiros |
| 4,352,808 A | 10/1982 | Rane et al. |
| 4,363,806 A | 12/1982 | Bergström et al. |
| 4,385,161 A | 5/1983 | Caunt et al. |
| 4,386,104 A | 5/1983 | Nazzaro-Porro |
| 4,393,066 A | 7/1983 | Garrett et al. |
| 4,427,670 A | 1/1984 | Ofuchi et al. |
| 4,439,416 A | 3/1984 | Cordon et al. |
| 4,439,441 A | 3/1984 | Hallesy et al. |
| 4,440,320 A | 4/1984 | Wernicke |
| 4,447,486 A | 5/1984 | Hoppe et al. |
| 4,469,674 A | 9/1984 | Shah et al. |
| 4,508,705 A | 4/1985 | Chaudhuri et al. |
| 4,522,948 A | 6/1985 | Walker |
| 4,529,601 A | 7/1985 | Broberg et al. |
| 4,529,605 A | 7/1985 | Lynch et al. |
| 4,552,872 A | 11/1985 | Cooper et al. |
| 4,574,052 A | 3/1986 | Gupte et al. |
| 4,576,961 A | 3/1986 | Lorck et al. |
| 4,595,526 A | 6/1986 | Lai |
| 4,603,812 A | 8/1986 | Stoesser et al. |
| 4,607,101 A | 8/1986 | Bernstein |
| 4,612,193 A | 9/1986 | Gordon et al. |
| 4,627,973 A | 12/1986 | Moran et al. |
| 4,628,063 A | 12/1986 | Haines et al. |
| 4,661,340 A | 4/1987 | Nagy née Kricsfalussy et al. |
| 4,661,524 A | 4/1987 | Thomson et al. |
| 4,672,078 A | 6/1987 | Sakai et al. |
| 4,673,569 A | 6/1987 | Shernov et al. |
| 4,678,463 A | 7/1987 | Millar |
| 4,701,320 A | 10/1987 | Hasegawa et al. |

(56) References Cited

U.S. PATENT DOCUMENTS

| | | |
|---|---|---|
| 4,725,609 A | 2/1988 | Kull, Jr. et al. |
| 4,738,396 A | 4/1988 | Doi et al. |
| 4,741,855 A | 5/1988 | Grote et al. |
| 4,752,465 A | 6/1988 | Mackles |
| 4,770,634 A | 9/1988 | Pellico |
| 4,772,427 A | 9/1988 | Dawson et al. |
| 4,780,309 A | 10/1988 | Geria et al. |
| 4,784,842 A | 11/1988 | London et al. |
| 4,792,062 A | 12/1988 | Goncalves |
| 4,798,682 A | 1/1989 | Ansmann |
| 4,804,674 A | 2/1989 | Curtis-Prior et al. |
| 4,806,262 A | 2/1989 | Snyder |
| 4,808,388 A | 2/1989 | Beutler et al. |
| 4,822,613 A | 4/1989 | Rodero |
| 4,822,614 A | 4/1989 | Rodero |
| 4,826,048 A | 5/1989 | Skorka et al. |
| 4,827,378 A | 5/1989 | Gillan et al. |
| 4,828,837 A | 5/1989 | Uster et al. |
| 4,836,217 A | 6/1989 | Fischer et al. |
| 4,837,019 A | 6/1989 | Georgalas et al. |
| 4,837,378 A | 6/1989 | Borgman |
| 4,844,902 A | 7/1989 | Grohe |
| 4,847,068 A | 7/1989 | Dole et al. |
| 4,849,117 A | 7/1989 | Bronner et al. |
| 4,849,211 A | 7/1989 | Schrauzer |
| 4,851,154 A | 7/1989 | Grollier et al. |
| 4,855,294 A | 8/1989 | Patel et al. |
| 4,863,900 A | 9/1989 | Pollock et al. |
| 4,867,967 A | 9/1989 | Crutcher |
| 4,873,078 A | 10/1989 | Edmundson et al. |
| 4,874,794 A | 10/1989 | Katz |
| 4,876,083 A | 10/1989 | Grollier et al. |
| 4,877,805 A | 10/1989 | Kligman |
| 4,885,282 A | 12/1989 | Thornfeldt |
| 4,897,262 A | 1/1990 | Nandagiri et al. |
| 4,902,281 A | 2/1990 | Avoy |
| 4,906,453 A | 3/1990 | Tsoucalas |
| 4,913,893 A | 4/1990 | Varco et al. |
| 4,919,934 A | 4/1990 | Deckner et al. |
| 4,933,330 A | 6/1990 | Jorgensen et al. |
| 4,950,420 A | 8/1990 | Svarz |
| 4,954,487 A | 9/1990 | Cooper et al. |
| 4,956,049 A | 9/1990 | Bernheim et al. |
| 4,957,732 A | 9/1990 | Grollier et al. |
| 4,963,351 A | 10/1990 | Weston |
| 4,965,063 A | 10/1990 | Casey et al. |
| 4,966,779 A | 10/1990 | Kirk |
| 4,970,067 A | 11/1990 | Panandiker et al. |
| 4,975,466 A | 12/1990 | Bottcher et al. |
| 4,981,367 A | 1/1991 | Brazelton |
| 4,981,677 A | 1/1991 | Thau |
| 4,981,679 A | 1/1991 | Briggs et al. |
| 4,981,845 A | 1/1991 | Pereira et al. |
| 4,985,459 A | 1/1991 | Sunshine et al. |
| 4,992,478 A | 2/1991 | Geria |
| 4,993,496 A | 2/1991 | Riedle et al. |
| 4,996,193 A | 2/1991 | Hewitt et al. |
| 5,002,540 A | 3/1991 | Brodman et al. |
| 5,002,680 A | 3/1991 | Schmidt et al. |
| 5,007,556 A | 4/1991 | Lover |
| 5,013,297 A | 5/1991 | Cattanach |
| 5,015,471 A | 5/1991 | Birtwistle et al. |
| 5,019,375 A | 5/1991 | Tanner et al. |
| 5,034,220 A | 7/1991 | Helioff et al. |
| 5,035,895 A | 7/1991 | Shibusawa et al. |
| 5,053,228 A | 10/1991 | Mori et al. |
| 5,071,648 A | 12/1991 | Rosenblatt |
| 5,071,881 A | 12/1991 | Parfondry et al. |
| 5,073,371 A | 12/1991 | Turner et al. |
| 5,082,651 A | 1/1992 | Healey et al. |
| 5,087,618 A | 2/1992 | Bodor |
| 5,089,252 A | 2/1992 | Grollier et al. |
| 5,091,111 A | 2/1992 | Neumiller |
| 5,094,853 A | 3/1992 | Hagarty |
| 5,100,917 A | 3/1992 | Flynn et al. |
| 5,104,645 A | 4/1992 | Cardin et al. |
| 5,112,359 A | 5/1992 | Murphy et al. |
| 5,114,718 A | 5/1992 | Damani |
| 5,122,519 A | 6/1992 | Ritter |
| 5,130,121 A | 7/1992 | Kopolow et al. |
| 5,133,972 A | 7/1992 | Ferrini et al. |
| 5,135,915 A | 8/1992 | Czarniecki et al. |
| 5,137,714 A | 8/1992 | Scott |
| 5,143,717 A | 9/1992 | Davis |
| 5,156,765 A | 10/1992 | Smrt |
| 5,160,665 A | 11/1992 | Owada et al. |
| 5,164,357 A | 11/1992 | Bartman et al. |
| 5,164,367 A | 11/1992 | Pickart |
| 5,167,950 A | 12/1992 | Lins |
| 5,171,577 A | 12/1992 | Griat et al. |
| 5,196,405 A | 3/1993 | Packman |
| 5,204,090 A | 4/1993 | Han |
| 5,204,093 A | 4/1993 | Victor |
| 5,208,031 A | 5/1993 | Kelly |
| 5,217,707 A | 6/1993 | Szabo et al. |
| 5,219,877 A | 6/1993 | Shah et al. |
| 5,221,534 A | 6/1993 | DesLauriers et al. |
| 5,221,696 A | 6/1993 | Ke et al. |
| 5,230,897 A | 7/1993 | Griffin et al. |
| 5,236,707 A | 8/1993 | Stewart, II |
| 5,252,246 A | 10/1993 | Ding et al. |
| 5,254,334 A | 10/1993 | Ramirez et al. |
| 5,262,407 A | 11/1993 | Leveque et al. |
| 5,266,592 A | 11/1993 | Grub et al. |
| 5,279,819 A | 1/1994 | Hayes |
| 5,286,475 A | 2/1994 | Louvet et al. |
| 5,294,365 A | 3/1994 | Welch et al. |
| 5,300,286 A | 4/1994 | Gee |
| 5,301,841 A | 4/1994 | Fuchs |
| 5,308,643 A | 5/1994 | Osipow et al. |
| 5,314,904 A | 5/1994 | Egidio et al. |
| 5,318,774 A | 6/1994 | Alban et al. |
| 5,322,683 A | 6/1994 | Mackles et al. |
| 5,326,557 A | 7/1994 | Glover et al. |
| 5,344,051 A | 9/1994 | Brown |
| 5,346,135 A | 9/1994 | Vincent |
| 5,352,437 A | 10/1994 | Nakagawa et al. |
| 5,369,131 A | 11/1994 | Poli et al. |
| 5,378,451 A | 1/1995 | Gorman et al. |
| 5,378,730 A | 1/1995 | Lee et al. |
| 5,380,761 A | 1/1995 | Szabo Anna Z. et al. |
| 5,384,308 A | 1/1995 | Henkin |
| 5,385,943 A | 1/1995 | Nazzaro-Porro |
| 5,389,305 A | 2/1995 | Repinec et al. |
| 5,389,676 A | 2/1995 | Michaels |
| 5,397,312 A | 3/1995 | Rademaker et al. |
| 5,398,846 A | 3/1995 | Corba et al. |
| 5,399,205 A | 3/1995 | Shinohara et al. |
| 5,411,992 A | 5/1995 | Eini et al. |
| 5,422,361 A | 6/1995 | Munayyer et al. |
| 5,429,815 A | 7/1995 | Faryniarz et al. |
| 5,435,996 A | 7/1995 | Glover et al. |
| 5,439,670 A | 8/1995 | Purewal et al. |
| 5,439,682 A | 8/1995 | Wivell et al. |
| 5,447,725 A | 9/1995 | Damani et al. |
| 5,449,520 A | 9/1995 | Frigerio et al. |
| 5,451,404 A | 9/1995 | Furman |
| 5,482,965 A | 1/1996 | Rajadhyaksha |
| 5,491,245 A | 2/1996 | Gruning et al. |
| 5,500,211 A | 3/1996 | George et al. |
| 5,508,033 A | 4/1996 | Briand et al. |
| 5,512,555 A | 4/1996 | Waldstreicher |
| 5,514,367 A | 5/1996 | Lentini et al. |
| 5,514,369 A | 5/1996 | Salka et al. |
| 5,520,918 A | 5/1996 | Smith |
| 5,523,078 A | 6/1996 | Baylin |
| 5,527,534 A | 6/1996 | Myhling |
| 5,527,822 A | 6/1996 | Scheiner |
| 5,529,770 A | 6/1996 | McKinzie et al. |
| 5,531,703 A | 7/1996 | Skwarek et al. |
| 5,534,261 A | 7/1996 | Rodgers et al. |
| 5,536,743 A | 7/1996 | Borgman |
| 5,540,853 A | 7/1996 | Trinh et al. |
| 5,545,401 A | 8/1996 | Shanbrom |

(56) References Cited

U.S. PATENT DOCUMENTS

| | | |
|---|---|---|
| 5,547,989 A | 8/1996 | Chamness |
| 5,558,872 A | 9/1996 | Jones et al. |
| 5,560,859 A | 10/1996 | Hartmann et al. |
| 5,567,420 A | 10/1996 | McEleney et al. |
| 5,576,016 A | 11/1996 | Amselem et al. |
| 5,578,315 A | 11/1996 | Chien et al. |
| 5,585,104 A | 12/1996 | Ha et al. |
| 5,589,157 A | 12/1996 | Hatfield |
| 5,589,515 A | 12/1996 | Suzuki et al. |
| 5,597,560 A | 1/1997 | Bergamini et al. |
| 5,603,940 A | 2/1997 | Candau et al. |
| 5,605,679 A | 2/1997 | Hansenne et al. |
| 5,608,119 A | 3/1997 | Amano et al. |
| 5,611,463 A | 3/1997 | Favre |
| 5,612,056 A | 3/1997 | Jenner et al. |
| 5,613,583 A | 3/1997 | Kono et al. |
| 5,613,623 A | 3/1997 | Hildebrandt |
| 5,614,171 A | 3/1997 | Clavenna et al. |
| 5,614,178 A | 3/1997 | Bloom et al. |
| 5,618,516 A | 4/1997 | Clavenna et al. |
| 5,635,469 A | 6/1997 | Fowler et al. |
| 5,641,480 A | 6/1997 | Vermeer |
| 5,643,600 A | 7/1997 | Mathur |
| 5,645,842 A | 7/1997 | Gruning et al. |
| 5,648,380 A | 7/1997 | Martin |
| 5,650,554 A | 7/1997 | Moloney |
| 5,658,575 A | 8/1997 | Ribier et al. |
| 5,658,749 A | 8/1997 | Thornton |
| 5,658,956 A | 8/1997 | Martin et al. |
| 5,663,208 A | 9/1997 | Martin |
| 5,672,634 A | 9/1997 | Tseng et al. |
| 5,679,324 A | 10/1997 | Lisboa et al. |
| 5,683,710 A | 11/1997 | Akemi et al. |
| 5,686,088 A | 11/1997 | Mitra et al. |
| 5,693,258 A | 12/1997 | Tonomura et al. |
| 5,695,551 A | 12/1997 | Buckingham et al. |
| 5,695,747 A | 12/1997 | Forestier et al. |
| 5,700,396 A | 12/1997 | Suzuki et al. |
| 5,705,472 A | 1/1998 | Hayes et al. |
| 5,716,611 A | 2/1998 | Oshlack et al. |
| 5,716,621 A | 2/1998 | Bello |
| 5,719,122 A | 2/1998 | Chiodini et al. |
| 5,719,197 A | 2/1998 | Kanios et al. |
| 5,725,872 A | 3/1998 | Stamm et al. |
| 5,725,874 A | 3/1998 | Oda |
| 5,730,964 A | 3/1998 | Waldstreicher |
| 5,733,558 A | 3/1998 | Breton et al. |
| 5,733,572 A | 3/1998 | Unger et al. |
| 5,747,049 A | 5/1998 | Tominaga |
| 5,753,241 A | 5/1998 | Ribier et al. |
| 5,753,245 A | 5/1998 | Fowler et al. |
| 5,753,270 A | 5/1998 | Beauchamp et al. |
| 5,759,520 A | 6/1998 | Sachetto |
| 5,759,579 A | 6/1998 | Singh et al. |
| 5,767,104 A | 6/1998 | Bar-Shalom et al. |
| 5,773,410 A | 6/1998 | Yamamoto |
| 5,783,202 A | 7/1998 | Tomlinson et al. |
| 5,788,664 A | 8/1998 | Scalise |
| 5,792,448 A | 8/1998 | Dubief et al. |
| 5,792,922 A | 8/1998 | Moloney |
| 5,797,955 A | 8/1998 | Walters |
| 5,804,546 A | 9/1998 | Hall et al. |
| 5,807,571 A | 9/1998 | List |
| 5,817,322 A | 10/1998 | Xu et al. |
| 5,824,650 A | 10/1998 | De Lacharriere et al. |
| 5,833,960 A | 11/1998 | Gers-Barlag et al. |
| 5,833,961 A | 11/1998 | Siegfried et al. |
| 5,837,270 A | 11/1998 | Burgess |
| 5,840,744 A | 11/1998 | Borgman |
| 5,840,771 A | 11/1998 | Oldham et al. |
| 5,843,411 A | 12/1998 | Hernandez et al. |
| 5,846,983 A | 12/1998 | Sandborn et al. |
| 5,849,042 A | 12/1998 | Lim et al. |
| 5,854,246 A | 12/1998 | Francois et al. |
| 5,856,452 A | 1/1999 | Moloney et al. |
| 5,858,371 A | 1/1999 | Singh et al. |
| 5,865,347 A | 2/1999 | Welschoff |
| 5,866,040 A | 2/1999 | Nakama et al. |
| 5,869,529 A | 2/1999 | Sintov et al. |
| 5,871,720 A | 2/1999 | Gutierrez et al. |
| 5,877,216 A | 3/1999 | Place et al. |
| 5,879,469 A | 3/1999 | Avram et al. |
| 5,881,493 A | 3/1999 | Restive |
| 5,885,581 A | 3/1999 | Massand |
| 5,889,028 A | 3/1999 | Sandborn et al. |
| 5,889,054 A | 3/1999 | Yu et al. |
| 5,891,458 A | 4/1999 | Britton et al. |
| 5,902,574 A | 5/1999 | Stoner et al. |
| 5,902,789 A | 5/1999 | Stoltz |
| 5,905,092 A | 5/1999 | Osborne et al. |
| 5,910,382 A | 6/1999 | Goodenough et al. |
| 5,911,981 A | 6/1999 | Dahms et al. |
| 5,912,007 A | 6/1999 | Pan et al. |
| 5,914,122 A | 6/1999 | Otterbeck et al. |
| 5,914,310 A | 6/1999 | Li et al. |
| 5,919,830 A | 7/1999 | Gopalkrishnan et al. |
| 5,922,331 A | 7/1999 | Mausner |
| 5,925,669 A | 7/1999 | Katz et al. |
| 5,939,376 A | 8/1999 | Durbut et al. |
| 5,948,682 A | 9/1999 | Moloney |
| 5,951,544 A | 9/1999 | Konwitz |
| 5,951,989 A | 9/1999 | Heymann |
| 5,951,993 A | 9/1999 | Scholz et al. |
| 5,952,373 A | 9/1999 | Lanzendorfer et al. |
| 5,952,392 A | 9/1999 | Katz et al. |
| 5,955,414 A | 9/1999 | Brown et al. |
| 5,959,161 A | 9/1999 | Kenmochi et al. |
| 5,961,957 A | 10/1999 | McAnalley |
| 5,961,998 A | 10/1999 | Arnaud et al. |
| 5,972,310 A | 10/1999 | Sachetto |
| 5,976,555 A | 11/1999 | Liu et al. |
| 5,980,904 A | 11/1999 | Leverett et al. |
| 5,990,100 A | 11/1999 | Rosenberg et al. |
| 5,993,846 A | 11/1999 | Friedman et al. |
| 6,001,341 A | 12/1999 | Genova et al. |
| 6,006,948 A | 12/1999 | Auer |
| 6,017,912 A | 1/2000 | Bussell |
| 6,019,967 A | 2/2000 | Breton et al. |
| 6,024,942 A | 2/2000 | Tanner et al. |
| 6,030,630 A | 2/2000 | Fleury et al. |
| 6,033,647 A | 3/2000 | Touzan et al. |
| 6,039,936 A | 3/2000 | Restle et al. |
| 6,042,848 A | 3/2000 | Lawyer et al. |
| 6,045,779 A | 4/2000 | Mueller et al. |
| 6,060,041 A | 5/2000 | Candau et al. |
| 6,071,536 A | 6/2000 | Suzuki et al. |
| 6,071,541 A | 6/2000 | Murad |
| 6,075,056 A | 6/2000 | Quigley, Jr. et al. |
| 6,080,394 A | 6/2000 | Lin et al. |
| 6,087,310 A | 7/2000 | Henkel |
| 6,087,317 A | 7/2000 | Gee |
| 6,090,772 A | 7/2000 | Kaiser et al. |
| 6,093,408 A | 7/2000 | Hasenoehrl et al. |
| 6,096,756 A | 8/2000 | Crain et al. |
| 6,110,477 A | 8/2000 | Hernandez et al. |
| 6,110,966 A | 8/2000 | Pollock |
| 6,113,888 A | 9/2000 | Castro et al. |
| 6,116,466 A | 9/2000 | Gueret et al. |
| 6,121,210 A | 9/2000 | Taylor |
| 6,126,920 A | 10/2000 | Jones et al. |
| 6,133,327 A | 10/2000 | Kimura et al. |
| 6,140,355 A | 10/2000 | Egidio et al. |
| 6,146,645 A | 11/2000 | Deckers et al. |
| 6,146,664 A | 11/2000 | Siddiqui |
| 6,162,834 A | 12/2000 | Sebillotte-Arnaud et al. |
| 6,165,455 A | 12/2000 | Torgerson et al. |
| 6,168,576 B1 | 1/2001 | Reynolds |
| 6,171,347 B1 | 1/2001 | Kunz et al. |
| 6,180,662 B1 | 1/2001 | Lanzendörfer et al. |
| 6,180,669 B1 | 1/2001 | Tamarkin |
| 6,183,762 B1 | 2/2001 | Deckers et al. |
| 6,186,367 B1 | 2/2001 | Harrold |
| 6,187,290 B1 | 2/2001 | Gilchrist et al. |
| 6,189,810 B1 | 2/2001 | Nerushai et al. |

(56) References Cited

U.S. PATENT DOCUMENTS

| | | | |
|---|---|---|---|
| 6,190,365 B1 | 2/2001 | Abbott et al. |
| 6,204,285 B1 | 3/2001 | Fabiano et al. |
| 6,210,656 B1 | 4/2001 | Touzan et al. |
| 6,210,742 B1 | 4/2001 | Deckers et al. |
| 6,214,318 B1 | 4/2001 | Osipow et al. |
| 6,214,788 B1 | 4/2001 | Velazco et al. |
| 6,217,887 B1 | 4/2001 | Beerse et al. |
| 6,221,381 B1 | 4/2001 | Shelford et al. |
| 6,221,823 B1 | 4/2001 | Crisanti et al. |
| 6,224,888 B1 | 5/2001 | Vatter et al. |
| 6,231,837 B1 | 5/2001 | Stroud et al. |
| 6,232,315 B1 | 5/2001 | Shafer et al. |
| 6,241,971 B1 | 6/2001 | Fox et al. |
| 6,251,369 B1 | 6/2001 | Stoltz |
| 6,258,374 B1 | 7/2001 | Friess et al. |
| 6,261,544 B1 | 7/2001 | Coury et al. |
| 6,264,964 B1 | 7/2001 | Mohammadi |
| 6,270,781 B1 | 8/2001 | Gehlsen |
| 6,271,295 B1 | 8/2001 | Powell et al. |
| 6,274,150 B1 | 8/2001 | Simonnet et al. |
| 6,283,336 B1 | 9/2001 | Dwyer et al. |
| 6,284,802 B1 | 9/2001 | Bissett et al. |
| 6,287,546 B1 | 9/2001 | Reich et al. |
| 6,294,550 B1 | 9/2001 | Place et al. |
| 6,299,023 B1 | 10/2001 | Arnone |
| 6,299,032 B1 | 10/2001 | Hamilton |
| 6,299,900 B1 | 10/2001 | Reed et al. |
| 6,305,578 B1 | 10/2001 | Hildebrandt et al. |
| 6,306,841 B1 | 10/2001 | Place et al. |
| 6,308,863 B1 | 10/2001 | Harman |
| 6,319,913 B1 | 11/2001 | Mak et al. |
| 6,328,950 B1 | 12/2001 | Franzke et al. |
| 6,328,982 B1 | 12/2001 | Shiroyama et al. |
| 6,333,362 B1 | 12/2001 | Lorant |
| 6,335,022 B1 | 1/2002 | Simonnet et al. |
| 6,341,717 B2 | 1/2002 | Auer |
| 6,344,218 B1 | 2/2002 | Dodd et al. |
| 6,348,229 B1 | 2/2002 | Eini et al. |
| 6,352,727 B1 | 3/2002 | Takahashi |
| 6,355,230 B2 | 3/2002 | Gers-Barlag et al. |
| 6,358,541 B1 | 3/2002 | Goodman |
| 6,358,924 B1 | 3/2002 | Hoffmann |
| 6,364,854 B1 | 4/2002 | Ferrer et al. |
| 6,372,234 B1 | 4/2002 | Deckers et al. |
| 6,375,936 B1 | 4/2002 | Allard et al. |
| 6,375,960 B1 | 4/2002 | Simonnet et al. |
| 6,383,471 B1 | 5/2002 | Chen et al. |
| 6,395,258 B1 | 5/2002 | Steer |
| 6,395,300 B1 | 5/2002 | Straub et al. |
| 6,403,061 B1 | 6/2002 | Candau et al. |
| 6,403,069 B1 | 6/2002 | Chopra et al. |
| 6,410,036 B1 | 6/2002 | De Rosa et al. |
| 6,423,323 B2 | 7/2002 | Neubourg |
| 6,423,329 B1 | 7/2002 | Sine et al. |
| 6,428,772 B1 | 8/2002 | Singh et al. |
| 6,433,003 B1 | 8/2002 | Bobrove et al. |
| 6,433,024 B1 * | 8/2002 | Popp et al. ............... 514/714 |
| 6,433,033 B1 | 8/2002 | Isobe et al. |
| 6,433,068 B1 | 8/2002 | Morrison et al. |
| 6,437,006 B1 | 8/2002 | Yoon et al. |
| 6,440,429 B1 | 8/2002 | Torizuka et al. |
| 6,447,801 B1 | 9/2002 | Salafsky et al. |
| 6,451,777 B1 | 9/2002 | Bradbury et al. |
| 6,455,076 B1 | 9/2002 | Hahn et al. |
| 6,468,989 B1 | 10/2002 | Chang et al. |
| 6,479,058 B1 | 11/2002 | McCadden |
| 6,479,060 B1 | 11/2002 | Jones et al. |
| 6,479,532 B1 | 11/2002 | Kamimura et al. |
| 6,482,810 B1 | 11/2002 | Brem et al. |
| 6,486,168 B1 | 11/2002 | Skwierczynski et al. |
| 6,488,947 B1 | 12/2002 | Bekele |
| 6,511,655 B1 | 1/2003 | Muller et al. |
| 6,514,487 B1 | 2/2003 | Barr |
| 6,524,594 B1 | 2/2003 | Santora et al. |
| 6,531,118 B1 | 3/2003 | Gonzalez et al. |
| 6,534,455 B1 | 3/2003 | Maurin et al. |
| 6,536,629 B2 | 3/2003 | van der Heijden |
| 6,544,530 B1 | 4/2003 | Friedman |
| 6,544,562 B2 | 4/2003 | Singh et al. |
| 6,547,063 B1 | 4/2003 | Zaveri et al. |
| 6,548,074 B1 | 4/2003 | Mohammadi |
| 6,551,604 B1 | 4/2003 | Beck et al. |
| 6,562,355 B1 | 5/2003 | Renault |
| 6,566,350 B2 | 5/2003 | Ono et al. |
| 6,582,679 B2 | 6/2003 | Stein et al. |
| 6,582,710 B2 | 6/2003 | Deckers et al. |
| 6,589,509 B2 | 7/2003 | Keller et al. |
| 6,596,287 B2 | 7/2003 | Deckers et al. |
| 6,599,513 B2 | 7/2003 | Deckers et al. |
| 6,607,716 B1 | 8/2003 | Smith et al. |
| 6,610,315 B2 | 8/2003 | Scholz et al. |
| 6,620,773 B1 | 9/2003 | Stork et al. |
| 6,638,981 B2 | 10/2003 | Williams et al. |
| 6,649,571 B1 | 11/2003 | Morgan |
| 6,649,574 B2 | 11/2003 | Cardis et al. |
| 6,672,483 B1 | 1/2004 | Roy |
| 6,682,726 B2 | 1/2004 | Marchesi et al. |
| 6,682,750 B2 | 1/2004 | Loeffler et al. |
| 6,691,898 B2 | 2/2004 | Hurray et al. |
| 6,706,290 B1 | 3/2004 | Kajander et al. |
| 6,709,663 B2 | 3/2004 | Espinoza |
| 6,723,309 B1 | 4/2004 | Deane |
| 6,730,288 B1 | 5/2004 | Abram |
| 6,736,860 B2 | 5/2004 | Patel et al. |
| 6,753,000 B2 | 6/2004 | Breton et al. |
| 6,753,013 B1 | 6/2004 | Didriksen et al. |
| 6,753,167 B2 | 6/2004 | Moloney et al. |
| 6,762,158 B2 | 7/2004 | Lukenbach et al. |
| 6,765,001 B2 | 7/2004 | Gans et al. |
| 6,774,114 B2 | 8/2004 | Castiel et al. |
| 6,777,591 B1 | 8/2004 | Chaudhary |
| 6,790,435 B1 | 9/2004 | Ma et al. |
| 6,796,973 B1 | 9/2004 | Contente et al. |
| RE38,623 E | 10/2004 | Hernandez et al. |
| 6,811,767 B1 | 11/2004 | Bosch et al. |
| 6,834,778 B2 | 12/2004 | Jinbo et al. |
| 6,841,547 B2 | 1/2005 | Brown et al. |
| 6,843,390 B1 | 1/2005 | Bristor |
| 6,875,438 B2 | 4/2005 | Kraemer et al. |
| 6,881,271 B2 | 4/2005 | Ochiai |
| 6,890,567 B2 | 5/2005 | Nakatsu et al. |
| 6,897,195 B2 | 5/2005 | Su et al. |
| 6,902,737 B2 | 6/2005 | Quemin et al. |
| 6,911,211 B2 | 6/2005 | Eini et al. |
| 6,914,057 B1 | 7/2005 | Ryan et al. |
| 6,946,120 B2 | 9/2005 | Wai-Chiu So et al. |
| 6,946,139 B2 | 9/2005 | Henning |
| 6,951,654 B2 | 10/2005 | Malcolm et al. |
| 6,955,816 B2 | 10/2005 | Klysz |
| 6,956,062 B2 | 10/2005 | Beilfuss et al. |
| 6,958,154 B2 | 10/2005 | Andolino Brandt et al. |
| 6,967,023 B1 | 11/2005 | Eini et al. |
| 6,968,982 B1 | 11/2005 | Burns |
| 6,969,521 B1 | 11/2005 | Gonzalez et al. |
| RE38,964 E | 1/2006 | Shillington |
| 6,994,863 B2 | 2/2006 | Eini et al. |
| 7,002,486 B2 | 2/2006 | Lawrence |
| 7,014,844 B2 | 3/2006 | Mahalingam et al. |
| 7,021,499 B2 | 4/2006 | Hansen et al. |
| 7,029,659 B2 | 4/2006 | Abram et al. |
| 7,060,253 B1 | 6/2006 | Mundschenk |
| 7,078,058 B2 | 7/2006 | Jones et al. |
| 7,083,799 B1 | 8/2006 | Giacomoni |
| 7,137,536 B2 | 11/2006 | Walters et al. |
| 7,195,135 B1 | 3/2007 | Garcia et al. |
| 7,222,802 B2 | 5/2007 | Sweeton |
| 7,225,518 B2 | 6/2007 | Eidenschink et al. |
| 7,226,230 B2 | 6/2007 | Liberatore |
| 7,235,251 B2 | 6/2007 | Hamer et al. |
| 7,252,816 B1 | 8/2007 | Angel et al. |
| 7,270,828 B2 | 9/2007 | Masuda et al. |
| 7,455,195 B2 | 11/2008 | Mekata |
| 7,497,354 B2 | 3/2009 | Decottignies et al. |
| 7,575,739 B2 | 8/2009 | Tamarkin et al. |

(56) References Cited

U.S. PATENT DOCUMENTS

| | | | |
|---|---|---|---|
| 7,645,803 B2 | 1/2010 | Tamarkin et al. | |
| 7,654,415 B2 | 2/2010 | van der Heijden | |
| 7,682,623 B2 | 3/2010 | Eini et al. | |
| 7,700,076 B2 | 4/2010 | Tamarkin et al. | |
| 7,704,518 B2 | 4/2010 | Tamarkin et al. | |
| 7,758,888 B2 | 7/2010 | Lapidot et al. | |
| 7,793,807 B2 | 9/2010 | Goujon et al. | |
| 7,820,145 B2 | 10/2010 | Tamarkin et al. | |
| 7,842,791 B2 | 11/2010 | Britten et al. | |
| 7,960,416 B2 | 6/2011 | Sato et al. | |
| 8,114,385 B2 | 2/2012 | Tamarkin et al. | |
| 8,158,109 B2 | 4/2012 | Abram et al. | |
| 8,192,749 B2 | 6/2012 | Ashley | |
| 8,211,874 B2 | 7/2012 | Theobald et al. | |
| 8,343,945 B2 | 1/2013 | Tamarkin et al. | |
| 8,362,091 B2 | 1/2013 | Tamarkin et al. | |
| 8,435,498 B2 | 5/2013 | Tamarkin et al. | |
| 8,486,375 B2 | 7/2013 | Tamarkin et al. | |
| 8,518,376 B2 | 8/2013 | Tamarkin et al. | |
| 8,592,380 B2 | 11/2013 | Trumbore et al. | |
| 8,618,081 B2 | 12/2013 | Tamarkin et al. | |
| 8,623,330 B2 | 1/2014 | Gurge et al. | |
| 8,652,443 B2 | 2/2014 | Varanasi et al. | |
| 8,735,377 B1 | 5/2014 | Sipos | |
| 8,778,365 B1 | 7/2014 | Hardas et al. | |
| 8,784,780 B2 | 7/2014 | Gurge et al. | |
| 8,846,039 B2 | 9/2014 | Chung et al. | |
| 8,895,536 B2 | 11/2014 | Bannister et al. | |
| 8,992,896 B2 | 3/2015 | Tamarkin et al. | |
| 9,050,253 B2 | 6/2015 | Tamarkin et al. | |
| 9,101,662 B2 | 8/2015 | Tamarkin et al. | |
| 9,192,558 B2 | 11/2015 | Chen et al. | |
| 9,265,725 B2 * | 2/2016 | Tamarkin | A61K 8/362 |
| 9,265,740 B2 | 2/2016 | Johnston et al. | |
| 9,439,857 B2 | 9/2016 | Tamarkin et al. | |
| 9,474,720 B2 | 10/2016 | Yamamoto | |
| 9,492,412 B2 | 11/2016 | Tamarkin et al. | |
| 9,539,208 B2 | 1/2017 | Tamarkin et al. | |
| 9,539,266 B2 | 1/2017 | Mansouri | |
| 9,549,898 B2 | 1/2017 | Tamarkin et al. | |
| 9,572,775 B2 | 2/2017 | Tamarkin et al. | |
| 9,592,246 B2 | 3/2017 | Salman et al. | |
| 9,622,947 B2 | 4/2017 | Tamarkin et al. | |
| 9,636,405 B2 | 5/2017 | Tamarkin et al. | |
| 9,662,298 B2 | 5/2017 | Tamarkin et al. | |
| 9,668,972 B2 | 6/2017 | Tamarkin et al. | |
| 9,675,700 B2 | 6/2017 | Tamarkin et al. | |
| 9,682,021 B2 | 6/2017 | Tamarkin et al. | |
| 9,713,643 B2 | 7/2017 | Friedman et al. | |
| 9,795,564 B2 | 10/2017 | Tamarkin et al. | |
| 9,849,142 B2 | 12/2017 | Tamarkin et al. | |
| 9,884,017 B2 | 2/2018 | Tamarkin et al. | |
| 2001/0006654 A1 | 7/2001 | Cannell et al. | |
| 2001/0027218 A1 | 10/2001 | Stern et al. | |
| 2001/0027981 A1 | 10/2001 | Yquel | |
| 2001/0033838 A1 | 10/2001 | Farmer | |
| 2001/0036450 A1 | 11/2001 | Verite et al. | |
| 2001/0054574 A1 | 12/2001 | Navarro | |
| 2002/0002151 A1 | 1/2002 | Ono et al. | |
| 2002/0004063 A1 | 1/2002 | Zhang | |
| 2002/0013481 A1 | 1/2002 | Schonrock et al. | |
| 2002/0015721 A1 | 2/2002 | Simonnet et al. | |
| 2002/0031478 A1 | 3/2002 | Keller et al. | |
| 2002/0032171 A1 | 3/2002 | Chen et al. | |
| 2002/0035046 A1 | 3/2002 | Lukenbach et al. | |
| 2002/0035070 A1 | 3/2002 | Gardlik et al. | |
| 2002/0035087 A1 | 3/2002 | Barclay | |
| 2002/0035182 A1 | 3/2002 | L'Alloret et al. | |
| 2002/0039591 A1 | 4/2002 | Dahle | |
| 2002/0044659 A1 | 4/2002 | Ohta | |
| 2002/0045659 A1 | 4/2002 | Michelet et al. | |
| 2002/0048798 A1 | 4/2002 | Avery et al. | |
| 2002/0058010 A1 | 5/2002 | Picard-Lesboueyries et al. | |
| 2002/0072544 A1 | 6/2002 | Miller et al. | |
| 2002/0090386 A1 | 7/2002 | Haslwanter et al. | |
| 2002/0098215 A1 | 7/2002 | Douin et al. | |
| 2002/0111281 A1 | 8/2002 | Vishnupad | |
| 2002/0117516 A1 | 8/2002 | Lasserre et al. | |
| 2002/0134376 A1 | 9/2002 | Castro et al. | |
| 2002/0136755 A1 | 9/2002 | Tyrrell et al. | |
| 2002/0143188 A1 | 10/2002 | Garvey et al. | |
| 2002/0153390 A1 | 10/2002 | Vlodek | |
| 2002/0165170 A1 | 11/2002 | Wilson et al. | |
| 2002/0182162 A1 | 12/2002 | Shahinpoor et al. | |
| 2002/0182234 A1 | 12/2002 | Riedel et al. | |
| 2002/0187181 A1 | 12/2002 | Godbey et al. | |
| 2002/0198136 A1 | 12/2002 | Mak et al. | |
| 2003/0006193 A1 | 1/2003 | Ikeda et al. | |
| 2003/0013692 A1 | 1/2003 | Gullans et al. | |
| 2003/0017181 A1 | 1/2003 | Rood et al. | |
| 2003/0031693 A1 | 2/2003 | Breton et al. | |
| 2003/0053961 A1 | 3/2003 | Eccard | |
| 2003/0077297 A1 | 4/2003 | Chen et al. | |
| 2003/0077301 A1 | 4/2003 | Maibach et al. | |
| 2003/0078172 A1 | 4/2003 | Guiramand et al. | |
| 2003/0082120 A1 | 5/2003 | Milstein | |
| 2003/0108502 A1 | 6/2003 | Uchida et al. | |
| 2003/0114520 A1 | 6/2003 | Pereira et al. | |
| 2003/0118515 A1 | 6/2003 | Jew et al. | |
| 2003/0118527 A1 | 6/2003 | Jager et al. | |
| 2003/0129259 A1 | 7/2003 | Mahalingam et al. | |
| 2003/0130247 A1 | 7/2003 | Gans et al. | |
| 2003/0148949 A1 | 8/2003 | Podolsky | |
| 2003/0175232 A1 | 9/2003 | Elliott et al. | |
| 2003/0175315 A1 | 9/2003 | Yoo et al. | |
| 2003/0180347 A1 | 9/2003 | Young et al. | |
| 2003/0185839 A1 | 10/2003 | Podolsky | |
| 2003/0185861 A1 | 10/2003 | Hori et al. | |
| 2003/0194379 A1 | 10/2003 | Brugger et al. | |
| 2003/0195128 A1 | 10/2003 | Deckman et al. | |
| 2003/0206955 A1 | 11/2003 | Sonneville-Aubrun et al. | |
| 2003/0215418 A1 | 11/2003 | Asmus et al. | |
| 2003/0215472 A1 | 11/2003 | Bonda et al. | |
| 2003/0235597 A1 | 12/2003 | Withiam et al. | |
| 2004/0002550 A1 | 1/2004 | Mercurio | |
| 2004/0018228 A1 | 1/2004 | Fischell et al. | |
| 2004/0028752 A1 | 2/2004 | Kamm et al. | |
| 2004/0038912 A1 | 2/2004 | Michelet et al. | |
| 2004/0053797 A1 | 3/2004 | Chen et al. | |
| 2004/0058878 A1 | 3/2004 | Walker | |
| 2004/0063787 A1 | 4/2004 | Villanueva | |
| 2004/0067970 A1 | 4/2004 | Foster et al. | |
| 2004/0072638 A1 | 4/2004 | Enos et al. | |
| 2004/0076651 A1 | 4/2004 | Brocks et al. | |
| 2004/0078896 A1 | 4/2004 | Hellyer et al. | |
| 2004/0079361 A1 | 4/2004 | Clayton et al. | |
| 2004/0105825 A1 | 6/2004 | Henning | |
| 2004/0106688 A1 | 6/2004 | Koike et al. | |
| 2004/0120917 A1 | 6/2004 | Perrier et al. | |
| 2004/0127554 A1 | 7/2004 | Ghisalberti | |
| 2004/0138179 A1 | 7/2004 | Goldstein et al. | |
| 2004/0151671 A1 | 8/2004 | Abram et al. | |
| 2004/0151756 A1 | 8/2004 | Richards et al. | |
| 2004/0161447 A1 | 8/2004 | Paul | |
| 2004/0184992 A1 | 9/2004 | Abram | |
| 2004/0185123 A1 | 9/2004 | Mazzio et al. | |
| 2004/0191196 A1 | 9/2004 | Tamarkin | |
| 2004/0192754 A1 | 9/2004 | Shapira et al. | |
| 2004/0195276 A1 | 10/2004 | Fuchs | |
| 2004/0197276 A1 | 10/2004 | Takase et al. | |
| 2004/0197295 A1 | 10/2004 | Riedel et al. | |
| 2004/0198706 A1 | 10/2004 | Carrara | |
| 2004/0219122 A1 | 11/2004 | Masuda et al. | |
| 2004/0219176 A1 | 11/2004 | Dominguez | |
| 2004/0220187 A1 | 11/2004 | Stephenson et al. | |
| 2004/0229813 A1 | 11/2004 | DiPiano et al. | |
| 2004/0234475 A1 | 11/2004 | Lannibois-Drean et al. | |
| 2004/0241099 A1 | 12/2004 | Popp et al. | |
| 2004/0247531 A1 | 12/2004 | Riedel et al. | |
| 2004/0253275 A1 | 12/2004 | Eini et al. | |
| 2004/0258627 A1 | 12/2004 | Riedel et al. | |
| 2004/0258628 A1 | 12/2004 | Riedel et al. | |
| 2004/0265240 A1 | 12/2004 | Tamarkin et al. | |
| 2005/0002976 A1 | 1/2005 | Wu | |

(56) References Cited

U.S. PATENT DOCUMENTS

| | | |
|---|---|---|
| 2005/0013853 A1 | 1/2005 | Gil-Ad et al. |
| 2005/0031547 A1 | 2/2005 | Tamarkin et al. |
| 2005/0042182 A1 | 2/2005 | Arkin |
| 2005/0054991 A1 | 3/2005 | Tobyn et al. |
| 2005/0069566 A1 | 3/2005 | Tamarkin et al. |
| 2005/0074414 A1 | 4/2005 | Tamarkin et al. |
| 2005/0075407 A1 | 4/2005 | Tamarkin et al. |
| 2005/0079139 A1 | 4/2005 | Jacques et al. |
| 2005/0079228 A1 | 4/2005 | Jaiswal et al. |
| 2005/0084551 A1 | 4/2005 | Jensen et al. |
| 2005/0085843 A1 | 4/2005 | Opolski et al. |
| 2005/0100517 A1 | 5/2005 | Sanzgiri et al. |
| 2005/0101936 A1 | 5/2005 | Gonzales et al. |
| 2005/0106197 A1 | 5/2005 | Blin et al. |
| 2005/0123494 A1 | 6/2005 | Swaile et al. |
| 2005/0123496 A1 | 6/2005 | Shah et al. |
| 2005/0148552 A1 | 7/2005 | Ryan et al. |
| 2005/0153943 A1 | 7/2005 | Ashley |
| 2005/0164993 A1 | 7/2005 | Ashley |
| 2005/0186142 A1 | 8/2005 | Tamarkin et al. |
| 2005/0186147 A1 | 8/2005 | Tamarkin et al. |
| 2005/0189377 A1 | 9/2005 | Lanzendorfer et al. |
| 2005/0196414 A1 | 9/2005 | Dake et al. |
| 2005/0205086 A1 | 9/2005 | Tamarkin et al. |
| 2005/0207837 A1 | 9/2005 | Kosh et al. |
| 2005/0222090 A1 | 10/2005 | Cheng et al. |
| 2005/0232869 A1 | 10/2005 | Tamarkin et al. |
| 2005/0244342 A1 | 11/2005 | Friedman et al. |
| 2005/0244354 A1 | 11/2005 | Speron |
| 2005/0245902 A1 | 11/2005 | Cornish et al. |
| 2005/0252995 A1 | 11/2005 | Westphal et al. |
| 2005/0255048 A1 | 11/2005 | Hirsh et al. |
| 2005/0258189 A1 | 11/2005 | Peterson et al. |
| 2005/0266035 A1 | 12/2005 | Healy et al. |
| 2005/0268416 A1 | 12/2005 | Sommers |
| 2005/0271596 A1 | 12/2005 | Friedman et al. |
| 2005/0271598 A1 | 12/2005 | Friedman et al. |
| 2005/0276836 A1 | 12/2005 | Wilson et al. |
| 2005/0281749 A1 | 12/2005 | Willcox et al. |
| 2005/0281755 A1 | 12/2005 | Zarif et al. |
| 2005/0281766 A1 | 12/2005 | Martin et al. |
| 2005/0285912 A1 | 12/2005 | Delametter et al. |
| 2005/0287081 A1 | 12/2005 | Aust et al. |
| 2006/0008432 A1 | 1/2006 | Scarampi et al. |
| 2006/0018937 A1 | 1/2006 | Friedman |
| 2006/0018938 A1 | 1/2006 | Neubourg |
| 2006/0029565 A1 | 2/2006 | Xu et al. |
| 2006/0051301 A1 | 3/2006 | Galopin et al. |
| 2006/0054634 A1 | 3/2006 | Mekata |
| 2006/0057168 A1 | 3/2006 | Larm |
| 2006/0088561 A1 | 4/2006 | Eini et al. |
| 2006/0099151 A1 | 5/2006 | Neubourg |
| 2006/0108377 A1 | 5/2006 | Glynn et al. |
| 2006/0110415 A1 | 5/2006 | Gupta |
| 2006/0110418 A1 | 5/2006 | Johnson |
| 2006/0114745 A1 | 6/2006 | Ollmann et al. |
| 2006/0121073 A1 | 6/2006 | Goyal et al. |
| 2006/0140984 A1 | 6/2006 | Tamarkin et al. |
| 2006/0140990 A1 | 6/2006 | Bortz et al. |
| 2006/0160713 A1 | 7/2006 | Sekine et al. |
| 2006/0165616 A1 | 7/2006 | Brock et al. |
| 2006/0177392 A1 | 8/2006 | Walden |
| 2006/0193789 A1 | 8/2006 | Tamarkin et al. |
| 2006/0193813 A1 | 8/2006 | Simonnet |
| 2006/0204446 A1 | 9/2006 | Lulla et al. |
| 2006/0222675 A1 | 10/2006 | Sabnis et al. |
| 2006/0233721 A1 | 10/2006 | Tamarkin et al. |
| 2006/0239937 A2 | 10/2006 | Neubourg |
| 2006/0251684 A1 | 11/2006 | Annis et al. |
| 2006/0254597 A1 | 11/2006 | Thompson |
| 2006/0263323 A1 | 11/2006 | Hoang et al. |
| 2006/0269485 A1 | 11/2006 | Friedman et al. |
| 2006/0272199 A1 | 12/2006 | Licciardello |
| 2006/0275218 A1 | 12/2006 | Tamarkin et al. |
| 2006/0275221 A1 | 12/2006 | Tamarkin et al. |
| 2006/0285912 A1 | 12/2006 | Eini et al. |
| 2006/0292080 A1 | 12/2006 | Abram et al. |
| 2007/0009607 A1 | 1/2007 | Jones |
| 2007/0010580 A1 | 1/2007 | De Paoli Ambrosi |
| 2007/0015739 A1 | 1/2007 | Walker et al. |
| 2007/0017696 A1 | 1/2007 | Lin et al. |
| 2007/0020213 A1 | 1/2007 | Tamarkin |
| 2007/0020304 A1 | 1/2007 | Tamarkin et al. |
| 2007/0027055 A1 | 2/2007 | Koivisto et al. |
| 2007/0036831 A1 | 2/2007 | Baker |
| 2007/0053943 A1 | 3/2007 | Wang et al. |
| 2007/0059253 A1 | 3/2007 | Popp et al. |
| 2007/0069046 A1 | 3/2007 | Eini et al. |
| 2007/0071688 A1 | 3/2007 | Illel et al. |
| 2007/0098647 A1 | 5/2007 | Neubourg |
| 2007/0111956 A1 | 5/2007 | Matsushima et al. |
| 2007/0134174 A1 | 6/2007 | Irwin et al. |
| 2007/0140998 A1 | 6/2007 | Kato et al. |
| 2007/0140999 A1 | 6/2007 | Puglia et al. |
| 2007/0141086 A1 | 6/2007 | Ohara et al. |
| 2007/0142263 A1 | 6/2007 | Stahl et al. |
| 2007/0148112 A1 | 6/2007 | Dingley et al. |
| 2007/0148194 A1 | 6/2007 | Amiji et al. |
| 2007/0154402 A1 | 7/2007 | Trumbore et al. |
| 2007/0160548 A1 | 7/2007 | Riccardi et al. |
| 2007/0166274 A1 | 7/2007 | Mazur et al. |
| 2007/0224143 A1 | 9/2007 | Konis |
| 2007/0237724 A1 | 10/2007 | Abram et al. |
| 2007/0253911 A1 | 11/2007 | Tamarkin et al. |
| 2007/0264317 A1 | 11/2007 | Yosha et al. |
| 2007/0271235 A1 | 11/2007 | Frank et al. |
| 2007/0280891 A1 | 12/2007 | Tamarkin et al. |
| 2007/0281999 A1 | 12/2007 | Fox et al. |
| 2007/0292355 A1 | 12/2007 | Tamarkin et al. |
| 2007/0292359 A1 | 12/2007 | Friedman et al. |
| 2007/0292461 A1 | 12/2007 | Tamarkin et al. |
| 2008/0008397 A1 | 1/2008 | Kisilev |
| 2008/0015263 A1 | 1/2008 | Bolotin et al. |
| 2008/0015271 A1 | 1/2008 | Abram et al. |
| 2008/0031907 A1 | 2/2008 | Tamarkin et al. |
| 2008/0031908 A1 | 2/2008 | Aubrun-Sonneville et al. |
| 2008/0035155 A1 | 2/2008 | Dahl |
| 2008/0044444 A1 | 2/2008 | Tamarkin et al. |
| 2008/0050317 A1 | 2/2008 | Tamarkin et al. |
| 2008/0058055 A1 | 3/2008 | LeMay et al. |
| 2008/0063682 A1 | 3/2008 | Cashman et al. |
| 2008/0069779 A1 | 3/2008 | Tamarkin et al. |
| 2008/0131378 A1 | 6/2008 | Keller et al. |
| 2008/0138293 A1 | 6/2008 | Tamarkin et al. |
| 2008/0138296 A1 | 6/2008 | Tamarkin et al. |
| 2008/0152596 A1 | 6/2008 | Friedman et al. |
| 2008/0153789 A1 | 6/2008 | Dmowski et al. |
| 2008/0166303 A1 | 7/2008 | Tamarkin et al. |
| 2008/0167376 A1 | 7/2008 | Bar-Or et al. |
| 2008/0181854 A1 | 7/2008 | Eini et al. |
| 2008/0188445 A1 | 8/2008 | Muldoon et al. |
| 2008/0188446 A1 | 8/2008 | Muldoon et al. |
| 2008/0193762 A1 | 8/2008 | Dubertret et al. |
| 2008/0206155 A1 | 8/2008 | Tamarkin et al. |
| 2008/0206159 A1 | 8/2008 | Tamarkin et al. |
| 2008/0206161 A1 | 8/2008 | Tamarkin et al. |
| 2008/0241079 A1 | 10/2008 | Neubourg |
| 2008/0253973 A1 | 10/2008 | Tamarkin et al. |
| 2008/0255498 A1 | 10/2008 | Houle |
| 2008/0260655 A1 | 10/2008 | Tamarkin et al. |
| 2008/0292560 A1 | 11/2008 | Tamarkin et al. |
| 2008/0299220 A1 | 12/2008 | Tamarkin et al. |
| 2008/0311167 A1 | 12/2008 | Oronsky et al. |
| 2008/0317679 A1 | 12/2008 | Tamarkin et al. |
| 2009/0017147 A1 | 1/2009 | Lintner et al. |
| 2009/0041680 A1 | 2/2009 | Tamarkin et al. |
| 2009/0053290 A1 | 2/2009 | Sand et al. |
| 2009/0061001 A1 | 3/2009 | Hougaz |
| 2009/0068118 A1 | 3/2009 | Eini et al. |
| 2009/0093514 A1 | 4/2009 | Statham et al. |
| 2009/0130029 A1 | 5/2009 | Tamarkin et al. |
| 2009/0131488 A1 | 5/2009 | Harel et al. |
| 2009/0175799 A1 | 7/2009 | Tamarkin et al. |
| 2009/0180970 A1 | 7/2009 | Tamarkin et al. |

(56) References Cited

U.S. PATENT DOCUMENTS

| | | |
|---|---|---|
| 2009/0214628 A1 | 8/2009 | De Rijk |
| 2009/0291917 A1 | 11/2009 | Akama et al. |
| 2009/0317338 A1 | 12/2009 | Tamarkin et al. |
| 2010/0111879 A1 | 5/2010 | Tamarkin et al. |
| 2010/0137198 A1 | 6/2010 | Eini et al. |
| 2010/0221194 A1 | 9/2010 | Loupenok |
| 2010/0221195 A1 | 9/2010 | Tamarkin et al. |
| 2010/0266510 A1 | 10/2010 | Tamarkin et al. |
| 2010/0286417 A1 | 11/2010 | Mendes et al. |
| 2011/0002857 A1 | 1/2011 | Tamarkin et al. |
| 2011/0002969 A1 | 1/2011 | Serraima et al. |
| 2011/0008266 A1 | 1/2011 | Tamarkin et al. |
| 2011/0045037 A1 | 2/2011 | Tamarkin et al. |
| 2011/0097279 A1 | 4/2011 | Tamarkin et al. |
| 2011/0207765 A1 | 8/2011 | Van Den Bussche et al. |
| 2011/0212033 A1 | 9/2011 | Tamarkin et al. |
| 2011/0262542 A1 | 10/2011 | Ashley |
| 2011/0268665 A1 | 11/2011 | Tamarkin et al. |
| 2011/0281827 A1 | 11/2011 | Tamarkin et al. |
| 2012/0064136 A1 | 3/2012 | Baker, Jr. et al. |
| 2012/0082632 A1 | 4/2012 | Phillips et al. |
| 2012/0087872 A1 | 4/2012 | Tamarkin et al. |
| 2012/0128598 A1 | 5/2012 | Trumbore et al. |
| 2012/0141384 A1 | 6/2012 | Tamarkin |
| 2012/0148503 A1 | 6/2012 | Tamarkin et al. |
| 2012/0156144 A1 | 6/2012 | Tamarkin et al. |
| 2012/0164087 A1 | 6/2012 | Carter |
| 2012/0181201 A1 | 7/2012 | Heggie |
| 2012/0195836 A1 | 8/2012 | Tamarkin et al. |
| 2012/0213709 A1 | 8/2012 | Tamarkin et al. |
| 2012/0213710 A1 | 8/2012 | Tamarkin et al. |
| 2012/0237453 A1 | 9/2012 | Tamarkin et al. |
| 2013/0011342 A1 | 1/2013 | Tamarkin et al. |
| 2013/0028850 A1 | 1/2013 | Tamarkin et al. |
| 2013/0053353 A1 | 2/2013 | Tamarkin et al. |
| 2013/0064777 A1 | 3/2013 | Tamarkin et al. |
| 2013/0115173 A1 | 5/2013 | Trumbore et al. |
| 2013/0161351 A1 | 6/2013 | Eini et al. |
| 2013/0164225 A1 | 6/2013 | Tamarkin et al. |
| 2013/0183250 A1 | 7/2013 | Friedman et al. |
| 2013/0183251 A1 | 7/2013 | Tamarkin et al. |
| 2013/0189191 A1 | 7/2013 | Tamarkin et al. |
| 2013/0189193 A1 | 7/2013 | Tamarkin et al. |
| 2013/0189195 A1 | 7/2013 | Tamarkin et al. |
| 2013/0189196 A1 | 7/2013 | Tamarkin et al. |
| 2013/0195769 A1 | 8/2013 | Tamarkin et al. |
| 2013/0225536 A1 | 8/2013 | Tamarkin et al. |
| 2013/0251644 A1 | 9/2013 | Majhi et al. |
| 2013/0261565 A1 | 10/2013 | Wong et al. |
| 2013/0295022 A1 | 11/2013 | Friedman et al. |
| 2013/0296387 A1 | 11/2013 | Saad |
| 2014/0050673 A1 | 2/2014 | Tamarkin et al. |
| 2014/0066524 A1 | 3/2014 | Tamarkin et al. |
| 2014/0086848 A1 | 3/2014 | Tamarkin et al. |
| 2014/0121188 A1 | 5/2014 | Tamarkin et al. |
| 2014/0140937 A1 | 5/2014 | Gurge et al. |
| 2014/0147504 A1 | 5/2014 | Salman et al. |
| 2014/0182585 A1 | 7/2014 | Tamarkin et al. |
| 2014/0186269 A1 | 7/2014 | Tamarkin et al. |
| 2014/0186442 A1 | 7/2014 | Mansouri |
| 2014/0221320 A1 | 8/2014 | Joks et al. |
| 2014/0227199 A1 | 8/2014 | Tamarkin et al. |
| 2014/0228355 A1 | 8/2014 | Kortagere et al. |
| 2014/0242016 A1 | 8/2014 | Binks et al. |
| 2014/0248219 A1 | 9/2014 | Tamarkin et al. |
| 2014/0271494 A1 | 9/2014 | Tamarkin et al. |
| 2015/0025060 A1 | 1/2015 | Tamarkin et al. |
| 2015/0098907 A1 | 4/2015 | Tamarkin et al. |
| 2015/0118164 A1 | 4/2015 | Tamarkin et al. |
| 2015/0125496 A1 | 5/2015 | Yamamoto |
| 2015/0141381 A1 | 5/2015 | Levy et al. |
| 2015/0157586 A1 | 6/2015 | Tamarkin et al. |
| 2015/0164922 A1 | 6/2015 | Tamarkin et al. |
| 2015/0174144 A1 | 6/2015 | Bowser et al. |
| 2015/0190409 A1 | 7/2015 | Tamarkin et al. |
| 2015/0196570 A1 | 7/2015 | Tamarkin et al. |
| 2015/0209296 A1 | 7/2015 | Yamamoto |
| 2015/0374625 A1 | 12/2015 | Tamarkin et al. |
| 2016/0101051 A1 | 4/2016 | Tamarkin et al. |
| 2016/0101184 A1 | 4/2016 | Tamarkin et al. |
| 2016/0128944 A1 | 5/2016 | Chawrai et al. |
| 2016/0158261 A1 | 6/2016 | Friedman et al. |
| 2016/0213757 A1 | 7/2016 | Edelson et al. |
| 2016/0279152 A1 | 9/2016 | Chen et al. |
| 2016/0287615 A1 | 10/2016 | Chan et al. |
| 2016/0354473 A1 | 12/2016 | Tamarkin et al. |
| 2016/0361252 A1 | 12/2016 | Franke |
| 2016/0361320 A1 | 12/2016 | Zhao et al. |
| 2017/0014517 A1 | 1/2017 | Tamarkin |
| 2017/0049712 A1 | 2/2017 | Bhalani et al. |
| 2017/0119665 A1 | 5/2017 | Tamarkin et al. |
| 2017/0157175 A1 | 6/2017 | Tamarkin et al. |
| 2017/0172857 A1 | 6/2017 | Tamarkin et al. |
| 2017/0181970 A1 | 6/2017 | Tamarkin et al. |
| 2017/0216334 A1 | 8/2017 | Tamarkin et al. |
| 2017/0231909 A1 | 8/2017 | Tamarkin et al. |
| 2017/0274084 A1 | 9/2017 | Friedman et al. |
| 2017/0340743 A1 | 11/2017 | Tamarkin et al. |
| 2017/0348418 A1 | 12/2017 | Tamarkin et al. |
| 2017/0354597 A1 | 12/2017 | Tamarkin et al. |
| 2017/0360705 A1 | 12/2017 | Tamarkin et al. |
| 2018/0000734 A1 | 1/2018 | Tamarkin et al. |
| 2018/0064638 A1 | 3/2018 | Tamarkin et al. |

FOREIGN PATENT DOCUMENTS

| | | |
|---|---|---|
| AU | 2010219295 | 9/2012 |
| CA | 2114537 | 2/1993 |
| CA | 2154438 | 1/1996 |
| CA | 2422244 | 9/2003 |
| CA | 2502986 | 8/2011 |
| CA | 2534372 | 1/2012 |
| CA | 2536482 | 7/2012 |
| CH | 639913 | 12/1983 |
| DE | 1 882 100 | 11/1963 |
| DE | 1926796 | 11/1965 |
| DE | 4140474 | 6/1993 |
| DE | 10009233 | 8/2000 |
| DE | 10138495 | 2/2003 |
| DE | 102004016710 | 10/2005 |
| DE | 2 608 226 | 9/2007 |
| EP | 52404 | 5/1982 |
| EP | 0156507 A1 | 10/1985 |
| EP | 0186453 | 7/1986 |
| EP | 0 211 550 | 2/1987 |
| EP | 0 213 827 | 3/1987 |
| EP | 0214865 A2 | 3/1987 |
| EP | 0 216 856 | 4/1987 |
| EP | 0270316 | 6/1988 |
| EP | 297436 | 1/1989 |
| EP | 0 326 196 | 8/1989 |
| EP | 0 336 812 | 10/1989 |
| EP | 0 391 124 | 10/1990 |
| EP | 0404376 | 12/1990 |
| EP | 414920 | 3/1991 |
| EP | 0 454 102 A2 | 10/1991 |
| EP | 0 485 299 | 5/1992 |
| EP | 0484530 A1 | 5/1992 |
| EP | 0488089 A1 | 6/1992 |
| EP | 0 504 301 | 9/1992 |
| EP | 0 528 190 | 2/1993 |
| EP | 0535327 | 4/1993 |
| EP | 0 552 612 | 7/1993 |
| EP | 0569773 A2 | 11/1993 |
| EP | 0598412 | 11/1993 |
| EP | 0 662 431 | 7/1995 |
| EP | 0676198 | 10/1995 |
| EP | 0738516 | 10/1996 |
| EP | 0 757 959 | 2/1997 |
| EP | 0824911 | 2/1998 |
| EP | 0 829 259 | 3/1998 |
| EP | 0 928 608 | 7/1999 |
| EP | 0 979 654 | 2/2000 |
| EP | 0993827 A1 | 4/2000 |

(56) References Cited

FOREIGN PATENT DOCUMENTS

| | | |
|---|---|---|
| EP | 1 025 836 | 8/2000 |
| EP | 1055425 A2 | 11/2000 |
| EP | 0 506 197 | 7/2001 |
| EP | 1215258 | 6/2002 |
| EP | 1287813 | 3/2003 |
| EP | 1 308 169 | 5/2003 |
| EP | 1 375 386 | 1/2004 |
| EP | 1428521 | 6/2004 |
| EP | 1438946 | 7/2004 |
| EP | 1189579 | 9/2004 |
| EP | 1475381 | 11/2004 |
| EP | 1 483 001 | 12/2004 |
| EP | 1 500 385 | 1/2005 |
| EP | 1 537 916 | 6/2005 |
| EP | 1 600 185 | 11/2005 |
| EP | 1 653 932 | 5/2006 |
| EP | 1 734 927 | 12/2006 |
| EP | 1 758 547 | 3/2007 |
| EP | 1584324 | 11/2007 |
| EP | 1 889 609 | 2/2008 |
| EP | 1 902 706 | 3/2008 |
| EP | 2 129 383 | 12/2009 |
| EP | 2422768 | 2/2012 |
| EP | 2494959 | 9/2012 |
| FR | 2 456 522 | 12/1980 |
| FR | 2 591 331 | 6/1987 |
| FR | 2 640 942 | 6/1990 |
| FR | 2 736 824 | 1/1997 |
| FR | 2 774 595 | 8/1999 |
| FR | 2 789 371 | 8/2000 |
| FR | 2 793 479 | 11/2000 |
| FR | 2 814 959 | 4/2002 |
| FR | 2 833 246 | 6/2003 |
| FR | 2 840 903 | 12/2003 |
| FR | 2 843 373 | 2/2004 |
| FR | 2 845 672 | 4/2004 |
| FR | 2 848 998 | 6/2004 |
| FR | 2 860 976 | 4/2005 |
| FR | 2915891 | 11/2008 |
| GB | 808104 | 1/1959 |
| GB | 808105 | 1/1959 |
| GB | 922930 | 4/1963 |
| GB | 933486 | 8/1963 |
| GB | 998 490 | 7/1965 |
| GB | 1026831 | 4/1966 |
| GB | 1 033 299 | 6/1966 |
| GB | 1 081 949 | 9/1967 |
| GB | 1121358 | 7/1968 |
| GB | 1 162 684 | 8/1969 |
| GB | 1 170 152 | 11/1969 |
| GB | 1 201 918 | 8/1970 |
| GB | 1 347 950 | 2/1974 |
| GB | 1 351 761 | 5/1974 |
| GB | 1 351 762 | 5/1974 |
| GB | 1 353 381 | 5/1974 |
| GB | 1 376 649 | 12/1974 |
| GB | 1397285 | 6/1975 |
| GB | 1 408 036 | 10/1975 |
| GB | 1 457 671 | 12/1976 |
| GB | 1 489 672 | 10/1977 |
| GB | 2 004 746 | 4/1979 |
| GB | 1 561 423 | 2/1980 |
| GB | 2114580 | 8/1983 |
| GB | 2 153 686 | 8/1985 |
| GB | 2 172 298 | 9/1986 |
| GB | 2 206 099 | 12/1988 |
| GB | 2166651 | 5/1996 |
| GB | 2337461 | 11/1999 |
| GB | 2 367 809 | 4/2002 |
| GB | 2 406 330 | 3/2005 |
| GB | 2 406 791 | 4/2005 |
| GB | 2 474 930 | 7/2012 |
| IL | 49491 | 9/1979 |
| IL | 0152486 | 5/2003 |
| JP | 60001113 | 4/1978 |
| JP | 55069682 | 5/1980 |
| JP | 57044429 | 3/1982 |
| JP | 56039815 | 4/1984 |
| JP | 61275395 | 12/1986 |
| JP | 62241701 | 10/1987 |
| JP | 63119420 | 5/1988 |
| JP | 01100111 | 4/1989 |
| JP | 01156906 | 6/1989 |
| JP | 2184614 | 7/1990 |
| JP | 2255890 | 10/1990 |
| JP | 4-51958 | 2/1992 |
| JP | 04282311 | 10/1992 |
| JP | 4312521 | 11/1992 |
| JP | 5070340 | 3/1993 |
| JP | 5213734 | 8/1993 |
| JP | 6100414 | 4/1994 |
| JP | H06-263630 | 6/1994 |
| JP | 6329532 | 11/1994 |
| JP | 2007/155667 | 6/1995 |
| JP | 7215835 | 8/1995 |
| JP | 8501529 | 2/1996 |
| JP | 2008040899 | 2/1996 |
| JP | 8119831 | 5/1996 |
| JP | 8165218 | 6/1996 |
| JP | 8277209 | 10/1996 |
| JP | 09 084855 | 3/1997 |
| JP | 9099553 | 4/1997 |
| JP | 9110636 | 4/1997 |
| JP | 10114619 | 5/1998 |
| JP | 3050289 | 9/1998 |
| JP | 2010/332456 | 12/1998 |
| JP | 11501045 | 1/1999 |
| JP | 11250543 | 9/1999 |
| JP | 2000/017174 | 1/2000 |
| JP | 2000080017 | 3/2000 |
| JP | 2000128734 | 5/2000 |
| JP | 2000191429 | 7/2000 |
| JP | 2000/239140 | 9/2000 |
| JP | 2000/354623 | 12/2000 |
| JP | 2000351726 | 12/2000 |
| JP | 2001/002526 | 1/2001 |
| JP | 2001019606 | 1/2001 |
| JP | 2001072963 | 3/2001 |
| JP | 2002012513 | 1/2002 |
| JP | 2002047136 | 2/2002 |
| JP | 2002/524490 | 8/2002 |
| JP | 2002/302419 | 10/2002 |
| JP | 2003/012511 | 1/2003 |
| JP | 2003055146 | 2/2003 |
| JP | 2004/047136 | 2/2004 |
| JP | 2004/250435 | 9/2004 |
| JP | 2004/348277 | 12/2004 |
| JP | 2005/314323 | 11/2005 |
| JP | 2005350378 | 12/2005 |
| JP | 2006008574 | 1/2006 |
| JP | 2006/036317 | 2/2006 |
| JP | 2006/103799 | 4/2006 |
| JP | 2006525145 | 11/2006 |
| JP | 2007131539 | 5/2007 |
| JP | 4892282 | 3/2012 |
| KR | 143232 | 7/1998 |
| KR | 2001/003063 | 1/2001 |
| NZ | 520014 | 5/2005 |
| NZ | 540166 | 6/2007 |
| RU | 2277501 | 6/2006 |
| UA | 66796 | 6/2004 |
| WO | 82/01821 | 6/1982 |
| WO | WO-86/05389 | 9/1986 |
| WO | 88/01502 | 3/1988 |
| WO | WO-88/01863 | 3/1988 |
| WO | 88/08316 | 11/1988 |
| WO | WO-89/06537 | 7/1989 |
| WO | WO-90/05774 | 5/1990 |
| WO | WO-91/11991 | 8/1991 |
| WO | WO-92/00077 | 1/1992 |
| WO | 92/05142 | 4/1992 |
| WO | 92/05763 | 4/1992 |
| WO | WO-92/11839 | 7/1992 |
| WO | WO 92/13602 | 8/1992 |

(56) References Cited

FOREIGN PATENT DOCUMENTS

| | | |
|---|---|---|
| WO | 93/25189 | 12/1993 |
| WO | 94/06440 | 3/1994 |
| WO | WO 96/03115 | 2/1996 |
| WO | WO-96/03115 | 2/1996 |
| WO | WO-96/19921 | 7/1996 |
| WO | WO 96/19921 | 7/1996 |
| WO | 96/24325 | 8/1996 |
| WO | 96/26711 | 9/1996 |
| WO | WO-96/27376 | 9/1996 |
| WO | WO-96/39119 | 12/1996 |
| WO | 97/03638 | 2/1997 |
| WO | 97/39745 | 10/1997 |
| WO | 98/17282 | 4/1998 |
| WO | WO-98/18472 | 5/1998 |
| WO | WO-98/19654 | 5/1998 |
| WO | WO-98/21955 | 5/1998 |
| WO | WO-98/23291 | 6/1998 |
| WO | WO 98/31339 | 7/1998 |
| WO | WO-98/36733 | 8/1998 |
| WO | 98/52536 | 11/1998 |
| WO | WO-99/08649 | 2/1999 |
| WO | WO-99/20250 | 4/1999 |
| WO | WO-99/37282 | 7/1999 |
| WO | 99/53923 | 10/1999 |
| WO | WO-00/09082 | 2/2000 |
| WO | WO-00/15193 | 3/2000 |
| WO | 00/23051 | 4/2000 |
| WO | WO 00/62776 | 4/2000 |
| WO | 00/33825 | 6/2000 |
| WO | 00/38731 | 7/2000 |
| WO | WO-00/61076 | 10/2000 |
| WO | WO 00/72805 | 12/2000 |
| WO | WO-00/76461 | 12/2000 |
| WO | 01/05366 | 1/2001 |
| WO | WO 01/01949 | 1/2001 |
| WO | 01/10961 | 2/2001 |
| WO | WO-01/08681 | 2/2001 |
| WO | 01/53198 | 7/2001 |
| WO | 01/54212 | 7/2001 |
| WO | 01/62209 | 8/2001 |
| WO | WO-01/54679 | 8/2001 |
| WO | WO-01/70242 A2 | 9/2001 |
| WO | WO 2001/76579 A1 | 10/2001 |
| WO | 01/82880 | 11/2001 |
| WO | 01/82890 | 11/2001 |
| WO | 01/85102 | 11/2001 |
| WO | 01/85128 | 11/2001 |
| WO | 01/95728 | 12/2001 |
| WO | WO-02/00820 | 1/2002 |
| WO | WO 02/07685 | 1/2002 |
| WO | 02/15860 | 2/2002 |
| WO | 02/15873 | 2/2002 |
| WO | WO 02/24161 | 3/2002 |
| WO | WO-02/28435 | 4/2002 |
| WO | WO-02/41847 A1 | 5/2002 |
| WO | WO-02/43490 | 6/2002 |
| WO | WO-02/062324 | 8/2002 |
| WO | 02/078667 | 10/2002 |
| WO | 02/087519 | 11/2002 |
| WO | 03/000223 | 1/2003 |
| WO | 03/002082 | 1/2003 |
| WO | WO 03/005985 | 1/2003 |
| WO | 03/013984 | 2/2003 |
| WO | WO 03/015699 | 2/2003 |
| WO | WO-03/051294 | 6/2003 |
| WO | 03/055454 | 7/2003 |
| WO | WO-03/053292 | 7/2003 |
| WO | WO-03/055445 | 7/2003 |
| WO | 03/070301 | 8/2003 |
| WO | 03/071995 | 9/2003 |
| WO | WO-03/075851 | 9/2003 |
| WO | 03/097002 | 11/2003 |
| WO | WO-03/092641 | 11/2003 |
| WO | WO 03/094873 | 11/2003 |
| WO | 2004/017962 | 3/2004 |
| WO | 2004/037197 | 5/2004 |
| WO | WO-2004/037225 | 5/2004 |
| WO | 2004/003284 | 8/2004 |
| WO | 2004/064769 | 8/2004 |
| WO | WO-2004/064833 | 8/2004 |
| WO | WO-2004/071479 A1 | 8/2004 |
| WO | 2004/078158 | 9/2004 |
| WO | WO-2004/078896 | 9/2004 |
| WO | 2004/093895 | 11/2004 |
| WO | WO-2004/112780 | 12/2004 |
| WO | WO 2005/009416 | 2/2005 |
| WO | WO-2005/011567 A2 | 2/2005 |
| WO | WO-2005/018530 | 3/2005 |
| WO | WO-2005/018530 A2 | 3/2005 |
| WO | WO-2005/032522 | 4/2005 |
| WO | WO-2005/044219 | 5/2005 |
| WO | 2005/063224 | 7/2005 |
| WO | WO-2005/065652 | 7/2005 |
| WO | WO-2005/076697 | 8/2005 |
| WO | WO-2005/097068 | 10/2005 |
| WO | WO-2005/097068 A1 | 10/2005 |
| WO | 2005/102282 | 11/2005 |
| WO | 2005/102539 | 11/2005 |
| WO | WO-2005/117813 | 12/2005 |
| WO | WO-2006/003481 A2 | 1/2006 |
| WO | 2006/011046 | 2/2006 |
| WO | 2006/020682 | 2/2006 |
| WO | WO-2006/010589 | 2/2006 |
| WO | 2006/028339 | 3/2006 |
| WO | WO-2006/031271 | 3/2006 |
| WO | 2006/045170 | 5/2006 |
| WO | 2006/079632 | 8/2006 |
| WO | 2006/081327 | 8/2006 |
| WO | WO-2006/091229 | 8/2006 |
| WO | WO-2006/100485 | 9/2006 |
| WO | 2006/121610 | 11/2006 |
| WO | 2006/122158 | 11/2006 |
| WO | WO-2006/120682 | 11/2006 |
| WO | WO-2006/129161 | 12/2006 |
| WO | WO-2006/131784 | 12/2006 |
| WO | WO-2007/007208 | 1/2007 |
| WO | WO 2007/010494 | 1/2007 |
| WO | WO-2007/012977 | 2/2007 |
| WO | WO-2007/023396 | 3/2007 |
| WO | WO-2007/031621 A2 | 3/2007 |
| WO | WO-2007/039825 | 4/2007 |
| WO | WO-2007/050543 | 5/2007 |
| WO | WO-2007/054818 | 5/2007 |
| WO | WO-2007/072216 | 6/2007 |
| WO | WO 2007/082698 | 7/2007 |
| WO | WO-2007/085899 | 8/2007 |
| WO | WO-2007/085902 | 8/2007 |
| WO | WO-2007/099396 | 9/2007 |
| WO | 2007/111962 | 10/2007 |
| WO | 2008/010963 | 1/2008 |
| WO | WO-2008/008397 | 1/2008 |
| WO | 2008/041045 | 4/2008 |
| WO | WO-2008/038147 | 4/2008 |
| WO | WO-2008/075207 | 6/2008 |
| WO | WO-2008/087148 | 7/2008 |
| WO | WO 2008/104734 | 9/2008 |
| WO | WO-2008/110872 A2 | 9/2008 |
| WO | 2008/152444 | 12/2008 |
| WO | WO-2009/007785 A2 | 1/2009 |
| WO | WO-2009/069006 A2 | 6/2009 |
| WO | WO-2009/072007 A2 | 6/2009 |
| WO | 2009090558 | 7/2009 |
| WO | WO-2009/087578 A2 | 7/2009 |
| WO | WO-2009/090495 A2 | 7/2009 |
| WO | WO-2009/090558 A2 | 7/2009 |
| WO | WO-2009/098595 A2 | 8/2009 |
| WO | WO 2011/006026 | 1/2011 |
| WO | WO 2011/013008 A2 | 2/2011 |
| WO | WO 2011/013009 A2 | 2/2011 |
| WO | WO 2011/026094 | 3/2011 |
| WO | 2011/039637 | 4/2011 |
| WO | 2011/039638 | 4/2011 |
| WO | WO 2011/064631 | 6/2011 |
| WO | WO 2011/106026 | 9/2011 |

(56) References Cited

FOREIGN PATENT DOCUMENTS

| | | |
|---|---|---|
| WO | WO 2011/138678 | 11/2011 |
| WO | WO 2013/136192 | 9/2013 |
| WO | WO 2014/134394 | 9/2014 |
| WO | WO 2014/134427 | 9/2014 |
| WO | WO 2014/151347 | 9/2014 |
| WO | WO 2014/201541 | 12/2014 |
| WO | WO 2015/075640 | 5/2015 |
| WO | WO 2015/114320 | 8/2015 |
| WO | WO 2015/153864 | 10/2015 |
| WO | WO 2017/029647 A1 | 2/2017 |
| WO | WO 2017/030555 A1 | 2/2017 |

OTHER PUBLICATIONS http://www.naturalwellbeing.com/learning-center/Cetearyl_Alcohol (accessed Jan. 13, 2014).*
Effendy I. et al., "Surfactants and experimental irritant contact dermatitis", Contact Dermatitis, 33(4), pp. 217-225 (1995) (abstract).*
Barry, B.W. et al, Comparative bio-availability and activity of proprietary topical corticosteroid preparations: vasoconstrictor assays on thirty-one ointments, British Journal of Dermatology, 93, 563-571, 1975.
Martindale, The extra pharmacopoeia [28th] edition, Eds.: Reynolds, J.E.F. and Prasad, A.B., The Pharmaceutical Press, London, pp. 862-864, 1982.
Wormser et al., Protective effect of povidone-iodine ointment against skin lesions induced by sulphur and nitrogen mustards and by non-mustard vesicants, Arch. Toxicol., 1997, 71, 165-170.
Wormser, Early topical treatment with providone-iodine ointment reduces, and sometimes prevents, skin damage following heat stimulus, Letter to the Editor, Burns 24, pp. 383, 1998.
Alcohol SDA 40B.http://www.pharmco-prod.com/pages/MSDS/SDA_40B_200.pdf Accessed Dec. 9, 2008, 2 pages.
Ambrose, Ursual et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds," Antimicrobial Agents and Chemotherapy, vol. 35, No. 9, pp. 1799-1803, 1991.
Arisan, http://www.arisankimya.com/kozmetik.htm Accessed Dec. 10, 2008.
Benet, et al., Application of NMR for the Determination of HLB Values of Nonionic Surfactants, Journal of the American Oil Chemists Society, vol. 49, 1972, 499-500.
Bucks, Daniel A.W., et al., "Bioavailability of Topically Administered Steroids: A 'Mass Balance' Technique," Journal of Investigative Dermatology, vol. 91, No. 1, Jul. 1988, pp. 29-33.
Carbowax 1000MSDS; http://www.sciencelab.com/xMSDS-Polyethylene_glycol_1000-9926622. Accessed Dec. 13, 2008, 6 pages.
Cheshire, et al., Disorders of Sweating, www.medscape.com, Semin Neurol 23(4):399-406, 2003.
Coetzee, "Acceptability and Feasibility of Micralax applicators and of methyl cellulose gel placebo for large-scale clinical trials of vaginal microbicides," Nicol.AIDS 2001, vol. 15, No. 14, pp. 1837-1842.
D.W.A. Sharp Dictionary of Chemistry, Penguin Books, 1983, 3 pages.
Dalby, "Determination of Drug Solubility in Aerosol Propellants," Pharmaceutical Research, vol. 8, No. 9, 1991, pp. 1206-1209.
Denatonium Benzoate http://www.newdruginfo.com/pharmaceopeia/usp28/v28230/usp28nf23s0_m22790.htm Accessed Dec. 9, 2008.
Emulsifiers with HLB values. http://www.theherbarie.com/files/resources-center/formulating/Emulsifiers_HLB_Values.pdf accessed Aug. 5, 2009 (3 pps).
Ethanol, Accessed http://www.sigmaaldrich.com/catalog/ProductDetail.do?N4=E7023SIAL&N5=SEARCH_CONCAT_PNOBRAND_KEY&F=SPEC Dec. 9, 2008, 2 pages.
European Patent Application No. 06831721, Official Action, dated Feb. 3, 2009, 9 pages.

Flick, Cosmetic and Toiletry Formulations, vol. 5, 2nd Edition, Copyright 1996.
Fontana, Anthony, J., "Water Activity: Why It Is Important for Food Safety," International Conference on Food Safety, Nov. 16-18, 1998, 9 pages.
Galligan, John et al., "Adhesive Polyurethane Liners for Anterior Restorations," J. Dent. Res., Jul.-Aug. 1968, pp. 629-632.
Gill, A.M, et al., "Adverse Drug Reactions in a Paediatric Intensitve Care Unit," Acta Paediatr 84:438-441, 1995.
Glaser, et al., Hyperhidrosis: A Comprehensive and Practical Approach to Patient Management, Expert Rev. Dermatol. 1(6), 773-775 (2006).
Gschnait, F., et al., "Topical Indomethacin Protects from UVB and UVA Irriadiation," Arch. Dermatol. Res. 276:131-132, 1984.
Hall, Karla, "Diaper Area Hemanglomas: A Unique Set of Concerns," http://members.tripod.com/~Michelle_G/diaper.html, Dec. 1, 2008, 8 pages.
Hashim, et al. "Tinea versicolor and visceral leishmaniasis," Int J Dermatol., Apr. 1994; 33(4), pp. 258-259 (abstract only).
Hepburn, NC., "Cutaneous leishmaniasis," Clin Exp Dermatol, Jul. 2000; 25(5), pp. 363-370 (abstract only).
Hill, Randall M. (Ed.) Silicone Surfactants, Table of Contents and Chapter 7, "Silicone Surfactants: Applicants in the Personal Care Industry," by David T. Floyd, 1999 (30 Pages).
Innocenzi, Daniele et al., "An Open-Label Tolerability and Effacy Study of an Aluminum Sesquichlorhydrate Topical Foam in Axillary and Palmar Primary Hyperhidrosis," Dermatologic Therapy, vol. 21, S27-S30, 2008.
International Search Report and Written Opinion, International Application No. PCT/IB2006/003628, Foamix Ltd., dated Dec. 7, 2007, 15 pages.
International Search Report and Written Opinion, International Application No. PCT/US2007/004459, Foamix Ltd., dated Dec. 9, 2008, 2 pages.
International Search Report for International Application No. PCT/IB2006/003974, dated Feb. 25, 2008 (3 pages).
International Search Report, International Patent Application No. PCT/IB2007/003463, Foamix, Ltd., dated Jul. 18, 2008, 3 pages.
International Search Report, International Patent Application No. PCT/IB2007/003759, Foamix Ltd., dated Jul. 8, 2008 (3 pages).
Kalkan, et al., The Measurement of Sweat Intensity Using a New Technique, Tr. J. of Medical Sciences 28, 515-517 (1998).
Kathon™ CG (product information sheet by Rohm and Haas, Jun. 2006).
Kinnunen, Contact Dermatitis Sep. 1989; 21(3): 154-8.
Koerber, S., "Humectants and Water Activity," Water Activity News, 2000, ISSN No. 1083-3943.
Licking Vaginal Dryness without a Prescription. Accessed http://www.estronaut.com/a/vag_dryness.htm on Dec. 14, 2008.
Material Safety Data Sheet, Progesterone, Apr. 26, 2006, 5 pages.
Material Safety Data Sheet, Science Lab.com, Polyethylene Glycol 1000, MSDS, Nov. 6, 2008, 6 pages.
Merriam-Webster Online Dictionaary, 2008, "Mousse," Merriam-Webster Online, Dec. 8, 2008 http://www.merriam-webster.com/dictionary/mousse.
Metronidazole. www.usp.org/pdf/EN/veterinary/metronidazole.pdf. accessed Sep. 10, 2009, 4 pages.
Morgan, Timothy M., et al., "Enhanced Skin Permeation of Sex Hormones with Novel Topical Spray Vehicles," Journal of Pharmaceutical Sciences, vol. 87, No. 10, Oct. 1998, pp. 1213-1218.
OM Cinnamate. http://www.makingcosmetics.com/sunscreens/OM-Cinnamate-p102.html accessed Sep. 26, 2009.
Pendergrass, "The shape and dimensions of the human vagina as seen in three-dimensional vinyl polysiloxane casts," Gynecol Obstet. Invest. 1996:42(3):178-82 (abstract).
Progesterone MSDS. http://www.usp.org.pdf.EN/referenceStandards/msds/1568007.pdf on Dec. 14, 2002, 5 pages.
Savin, et al., "Tinea versicolor treated with terbinafine 1% solution," Int J. Dermatol, Nov. 1999; 38(11), pp. 863-865.
Schmidt A., "*Malassezia furfur*: a fungus belonging to the physiological skin flora and its relevance in skin disorders," Curtis., Jan. 1997; 59(1), pp. 21-24 (abstract).
Scott as Published in Pharmaceutical Dosage Forms; Disperse Systems, vol. 3, Copyright 1998.

(56) References Cited

OTHER PUBLICATIONS

Shear, et al., "Pharmacoeconomic analysis of topical treatments for tinea infections," Pharmacoeconomics. Mar. 1995; 7(3); pp. 251-267 (abstract only).
Sigma Aldrich, "HLB-Numbers in Lithography Nanopatterning," http://www.sigmaaldrich.com/materials-science/micro-and-nanoelectronics/lithography-nanopatterning/hlb-numbers.html, accessed: Feb. 2, 2009, pp. 1-3.
Sigma-Aldrich, Material Safety Data Sheet, Hydroxyethyl Cellulose, Mar. 3, 2004, 5 pages.
Skin Biology, CP Serum—Copper-Peptide Serum for Skin Regeneration and Reducing Wrinkles, Skin Biology, http://web.archive.org/web/20030810230608/http://www.skinbio.com/cpserum.html, Dec. 1, 2008, 21 pages.
Squire. J, "A randomised, single-blind, single-centre clinical trial to evaluate comparative clinical efficacy of shampoos containing ciclopirox olamine (1.5%) and salicylic acid (3%), or ketoconazole (2%, Nizoral) for the treatment of dandruff/seborrhoeic dermatitis," Dermatolog Treat. Jun. 2002;13(2):51-60 (abstract only).
Tan et al., "Effect of Carbopol and Polyvinylpyrrolidone on the Mechanical, Rheological, and Release Properties of Bioadhesive Polyethylene Glycol Gels," AAPS PharmSciTech, 2000; 1(3) article 24 (2000), 10 pages.
Torres-Rodriguez, JM., "New topical antifungal drugs," Arch Med Res. 1993 Winter; 24(4), pp. 371-375 (abstract).
Toxicology and Carcinogenesis Studies of t-Butyl Alcohol (CAS No. 75-65-0) in F344/N Rats and B6C3F1 Mice (Drinking Water Studies), http://ntp.niehs.nih.gob/?objectid-=0709F73D-A849-80CA-5FB784E866B576D1. Accessed Dec. 9, 2008.
Edirisinghe, et al., "Effect of fatty acids on endothelium-dependent relaxation in the rabbit aorta", Clin Sci (Lond). Aug. 2006; 111(2): 145-51.
Encyclopedia of Pharmaceutical Technology, Second Edition, vol. 3, Copyright 2002.
Hakan, et al., "The protective effect of fish oil enema in acetic acid and ethanol induced colitis," The Turkish Journal of Gasroenterology, 2000, vol. 11, No. 2, pp. 155-161.
http://ibabydoc.com/online/diseaseeczema.asp., Atopic Dermatitis, Copyright 2000.
http://web.archive.org/web/20000106225413/http://pharmacy.wilkes.edu/kibbeweb/lab7.html, Characteristics of Surfactants and Emulsions, Jan. 29, 2010, 5 pages.
http://www.agworkshop.com/p3.asp, AG&Co. Essential oil workshop, accessed Jan. 31, 2010.
Kanamoto, et al., "Pharmacokinetics of two rectal dosage forms of ketoprofen in patients after anal surgery," J Pharmacobiodyn., Mar. 1988; 11(3):141-5.
Leung, et al., "Bioadhesive Drug Delivery in Water-Soluble Polymers," American Chemical Society, Chapter 23, 1991, pp. 350-366.
Tarumoto, et al., Studies on toxicity of hydrocortisone 17-butyrate 21-propionate-1. Acute toxicity of hydrocortisone 17-butyrate 21-propionate and its analogues in mice, rats and dogs (author's trans), J Toxicol Sci., Jul. 1981; 6 Suppl: 1-16.
U.S. Appl. No. 60/789,186, filed Apr. 4, 2006, Tamarkin.
U.S. Appl. No. 60/815,948, filed Jun. 23, 2006, Tamarkin.
U.S. Appl. No. 60/818,634, filed Jul. 5, 2006, Friedman.
U.S. Appl. No. 60/843,140, filed Sep. 8, 2006, Tamarkin.
U.S. Appl. No. 61/248,144, filed Oct. 2, 2009, Tamarkin.
U.S. Appl. No. 61/322,148, filed Apr. 8, 2010, Tamarkin.
U.S. Appl. No. 61/363,577, filed Jul. 12, 2010, Eini.
"Burn patients need vitamin D supplements." *Decision News Media*, Jan. 23, 2004, http://www.nutraingredients.com/Research/Burn-patients-need-vitamin-D-supplements, Accessed: May 5, 2010.
"HLB Systems", http://pharmcal.tripod.com/ch17.htm, Accessed Sep. 17, 2010, pp. 1-3.
"Minocycline" accessed on Oct. 21, 2011 at en.wikipedia.org/wiki/Minocycline, 7 pages.
"Reaction Rate" Accessed at en.wikipedia.org/wiki/Reaction_rate on Dec. 18, 2011, 6 pages.

'Niram Chemicals' [online]. Niram Chemicals, [retrieved on Jul. 17, 2012]. Retrieved from the Internet: <URL: http://www.indiamart.com/niramchemicals/chemicals.html>, 7 pages.
'Surfactant' [online]. Wikipedia, 2010, [retrieved on Oct. 24, 2010]. Retrieved from the Internet: <URL: http://en.wikipedia.org/wiki/Surfactant>, 7 pages.
Adachi, Shuji. "Storage and Oxidative Stability of O/W/ Nano-emulsions." Foods Food Ingredients. J. Jpn. vol. 209, No. 11. 2004. 1 page.
Anton, N. et al. "Water-in-Oil Nano-Emulsion Formation by the phase inversion Temperature Method: A Novel and General Concept, a New Template for Nanoencapsulation," *Proceedings of the 33rd Annual Meeting and Exposition of the Controlled Release Society*, Jul. 2006, Vienna, Austria, 2 pages.
Arct et al., "Common Cosmetic Hydrophilic Ingredients as Penetration Modifiers of Flavonoids", International Journal of Cosmetic Science, 24(6):357-366 (2002)—Abstract, 1 page.
Augsburger, Larry L. et al. "Bubble Size Analysis of High Consistency Aerosol Foams and Its Relationship to Foam Rheology. Effects of Container Emptying, Propellent Type, and Time." Journal of Pharmaceutical Sciences. vol. 57, No. 4. Apr. 1968. pp. 624-631.
Austria, et al., "Stability of Vitamin C Derivatives in Solution and Topical Formulations", Journal of Pharmaceutical and Biomedical Analysis, 15:795-801 (1997).
Barry and Badal, "Stability of minocycline, doxycycline, and tetracycline stored in agar plates and microdilution trays," *Current Microbiology*, 1978, 1:33-36.
Bernstein, et al., Effects of the Immunomodulating Agent R837 on Acute and Latent Herpes Simplex Virus Type 2 Invections, Antimicrobial Agents and Chemotherapy, 33(9):1511-1515 (1989).
Blute, "Phase behavior of alkyl glycerol ether surfactants", Physical Chemistry Tenside Sur. Det., 35(3):207-212 (1998).
Brenes, et al., "Stability of Copigmented Anthocyanins and Asorbics Acid in a Grape Juice Model System", J. Agric Food Chem, 53(1):49-56 (2005)—Abstrace, 1 page.
Bronopol. Revtrieved online on Jun. 4, 2011. <URL:http://chemicalland21.com/specialtychem/perchem/BRONOPOL.html>. Jul. 17, 2006. 4 pages.
Buck, et al., "Treatment of Vaginal Intraephithelial Neoplasia (Primarily Low Grade) with Imiquimod 5% Cream", Journal of Lower Genetial Tract Disease, 7(3):290-293 (2003).
Bunker,et al., "Alterations in Scalp Blood Flow after the Epicutaneous Application of 3% Minoxidil and 0.1% Hexyl Nicotinate in Alopecia", Presented as a poster at the meeting of the British Society for Investigavie Dermatology, York, Sep. 1986 (2 pages).
Burton, et al., "Hypertrichosis Due to Minoxidil", British Journal of Dermatology, 101:593-595 (1979).
Campos, et al., "Ascorbic Acid and Its Derivatives in Cosmetic Formulations", Cosmetics and Toiletries, 115(6):59-62 (2000)—Abstract, 1 page.
Carelli, et al., "Effect of Vehicles on Yohimbine Permeation Across Excised Hairless Mouse Skin", Pharm Acta Helv, 73(3):127-134 (1998)—Abstract, 1 page.
Chebil, et al., "Soulbility of Flavonoids in Organic Solvents", J. Chem. Eng. Data, 52(5):1552-1556 (2007)—Abstract, 1 page.
Chiang, et al., "Bioavailability Assessment of Topical Delivery Systems: In Vitro Delivery of Minoxidil from Prototypical Semi-Solid Formulations", Int. J. Pharm, 49(2):109-114 (1989)—Abstract, 1 page.
Chinnian, et al., "Photostability Profiles of Minoxidil Solutions", PDA J. Pharm Sci Technol., 50(2):94-98 (1996)—Abstract, 1 page.
Chollet, et al., "Development of a Topically Active Imiquimod Formulation", Pharmaceutical Development and Technology, 4(1):35-43 (1999).
Chollet, et al., "The Effect of Temperatures on the Solubility of Immiquimod in Isostearic Acid", Abstract 3031, Pharmaceutical Research, vol. 14, No. 11 Supplemental (November), p. S475 (1997), 2 pages.
Colloidal Silica. Retrieved online on Jun. 4, 2011. <URL:http://www.grace.com/engineeredmaterials/materialsciences/colloidalsilica/default.aspx>. Copyright 2011. 4 pages.
Croda 2. Croda Cetomacrogol 1000 Product Information Sheet. 2011 (no month given). 1 page.

(56) References Cited

OTHER PUBLICATIONS

Croda. Aracel 165 Product Summary. 2011 (no month given). 1 page.
Dawber, et al., "Hypertrichosis in Females Applying Minoxidil Topical Solution and in Normal Controls", JEADV, 17:271-275 (2003).
Dentinger, et al., "Stability of Nifedipine in an Extemporaneously Compounded Oral Solution", American Journal of Health-System Pharmacy, 60(10):1019-1022 (2003)—Abstract, 1 page.
Disorder. (2007). In the American Heritage Dictionary of the English Language. Retrieved from http://www.credoreference.com/entry/hmdictenglang/disorder. 1 page.
Draelos, Z. D. "Antiperspirants and the Hyperhidrosis Patients." Dermatologic Therapy. 2001. vol. 14. pp. 220-224.
Edens, et al., "Storage Stability and Safey of Active Vitamin C in a New Dual-Chamber Dispenser", Journal of Applied Cosmetology, 17(4):136-143 (1999)—Abstract, 1 page.
Edwards, "Imiquimod in Clinical Practice", J. Am Acad Dermatol., 43(1, Pt 2):S12-S17 (2000)—Abstract, 1 page.
Esposito, E. et al. "Nanosystems for Skin Hydration: A Comparative Study." International Journal of Cosmetic Science. 29. 2007. pp. 39-47.
Ethylene Oxide Derivatives: An Essence of Every Industry. A definition of Emulsifier. Http://www.emulsifiers.in/ethylene_oxide_derivatives2.htm. Accessed Jul. 12, 2011. 3 pages.
Farahmand, et al., "Formulation and Evaluation of a Vitamin C Multiple Emulsion", Pharmaceutical Development and Technology, 11(2):255-261 (2006)—Abstract, 1 page.
Final Office Action for U.S. Appl. No. 11/430,437, Tamarkin et al., dated Dec. 16, 2008, 24 pages.
Gallarate, et al., "On the Stability of Ascorbic Acid in Emulsified Systems for Topical and Cosmetic Use", International Journal of Pharmaceutics, 188:233-241 (1999).
Gelbard et al. "Primary Pediatric Hyperhidrosis: A Review of Current Treatment Options." Pediatric Dermatology. 2008. 25 (6). pp. 591-598.
Gladkikh, "Ascorbic Acid and Methods of Increasing its Stability in Drugs", Translated from Khimiko-Farmatsevticheskii Zhurnal, 4(12):37-42 (1970)—1 page.
Graves, S. et al. "Structure of Concentrated Nanoemulsions." The Journal of Chemical Physics . . . 122 America Institute of Physics. Published Apr. 1, 2005. 6 pages.
Groveman, et al., "Lack of Efficacy of Polysorbate 60 in the Treatment of Male Pattern Baldness", Arch Intern Med, 145:1454-1458 (1985).
Hallstar. Retrieved online on Jun. 4, 2011. <URL:http://www.hallstar.com/pis.php?product=1H022>. 1 page.
Hargreaves, "Chemical Formulation, An Overview of Surfactant-Based Preparations Used in Everyday Life", *The Royal Society of Chemistry*, pp. 114-115 (2003).
Harrison, et al., "Effects of cytokines and R-837, a cytokine inducer, on UV-irradiation augmented recurrent genital herpes in guinea pigs", Antivial Res., 15(4):315-322 (1991).
Harrison, et al., "Modification of Immunological Responses and Clinical Disease During Topical R-837 Treatment of Genital HSV-2 Infection", Antiviral Research, 10:209-224 (1988).
Harrison, et al., "Pharmacokinetics and Safety of Iminquimod 5% Cream in the Treatment of Actinic Keratoses of the Face, Scalp, or Hands and Arms", Arch. Dermatol. Res., 296(1):6-11 (2004)—Abstract, 1 page.
Harrison, et al., "Posttherapy Suppression of Genital Herpes Simplex Virus (HSV) Recurrences and Enhancement of HSV-Specific T-Cell Memory by Imiquimod in Guinea Pigs", Antimicrobial Agents and Chemotherapy, 38(9):2059-2064 (1994).
Heart Failure, The Merck Manual, 2008 <<http://www.merck.com/mmhe/sec03/ch025/ch025a.html>> 12 pages.
Hormones. Http://www.greenwillowtree.com/Page.bok?file=libido.html. Jan. 2001.
Hubbe, Martin. Mini-Encyclopedia of Papermaking Wet-End Chemistry: Additives and Ingredients, their Composition, Functions, Strategies for Use. Retrieved online on Jun. 4, 2011. <URL://http://www4.ncsu.edu/~hubbe/CSIL.htm>. Feb. 1, 2001. 2 pages.
Hydroxyethylcellulose. Http://terpconnect.umd.edu/-choi/MSDS/Sigma-Aldrich/HYDROXYETHYL%20CELLULOSE, 5 pages, Jan. 14, 2004.
ICI Americas Inc. "The HLB System: A Time-Saving Guide to Emulsifier Selection." Mar. 1980. pp. 1-22.
Ikuta, et al., "Scanning Electron Microscopic Observation of Oil/Wax/Water/Surfacant System", Journal of SCCJ, 34(4):280-291 (2004)—Abstract, 1 page.
Indomethacin. Retrieved online on Jun. 3, 2011. <URL:http://it03.net/com/oxymatrine/down/1249534834.pdf>. Aug. 15, 2009. 3 pages.
Izquierdo, P. et al. "Formation and Stability of Nano-Emulsions Prepared Using the Phase Inversion Temperature Method." University of Barcelona. Sep. 17, 2001. 1 page.
Jan. "Troubled Times: Detergent Foam." http://zetatalk.com/health/theall7c.htm. Accessed Feb. 9, 2012. 2 pages.
Joseph, "Understanding foams & foaming," University of Minnesota (1997), at http://www.aem.umn.edu/people/faculty/joseph/archive/docs/understandingfoams.pdf, pp. 1-8.
Kang,et al., "Enhancement of the Stability and Skin Penetration of Vitamin C by Polyphenol", Immune Netw., 4(4):250-254 (2004)—Abstract, 1 page.
Karasu, T.B. et al., "Treatment of Patients with Major Depressive Disorder, Second Edition," pp. 1-78, 2000.
Kim, "Stability of Minoxidil in Aqueous Solution", Yakhak Hoechi, 30(5):228-231 (1986)—Abstract, 1 page.
Kleber, M.D., H.D. et al., "Treatment of Patients with Substance Use Disorders, Second Edition," pp. 1-276, 2006.
Kreuter, J. "Nanoparticles and microparticles for drug and vaccine delivery," J. Anat. (1996) 189, pp. 503-505.
Kumar, J. et ak., "Application of Broad Spectrum Antiseptic Povidone Iodine as Powerful Action: A Review," Journal of Pharmaceutical Science and Technology vol. 1(2), 2009, 48-58.
Kwak et al. "Study of Complete Transparent Nano-Emulsions which Contain Oils." IFSCC Conference 2003, Seoul, Korea, Sep. 22-24, 2003. 3 pages.
Lautenschlager, Dr. Hans. "A Closer Look on Natural Agents: Facts and Future Aspects." Kosmetic Konzept. Kosmetische Praxis. 2006 (no month given). (5), 8-10. 3 pages.
Lebwohl et al. "Treatment of Psoriasis. Part 1. Topical Therapy and Phototherapy." *J. Am. Acad. Dermatol.* 45:487-498. Oct. 2001.
Lebwohl et al., "A randomized, double-blind, placebo-controlled study of clobestasol propionate 0.05% foam in the treatment of nonscalp psoriasis," *International Journal of Dermatology*, 2002, 41(5): 269-274.
Lee, et al., "The Stabilization of L-Ascorbic Acid in Aqueous Solution and Water-in-Oil-in-Water Double Emulsion by Controlling pH and Electrolyte Concentration", J. Cosmet. Sci., 55:1-12 (Jan./Feb. 2004).
Li, et al., "Solubility Behavior of Imiquimod in Alkanoic Acids", Abstract 3029, Pharmaceutical Research, vol. 14, No. 11 Supplemental (November), p. S475 (1997), 2 pages.
Lippacher, A. et al. "Liquid and Semisolid SLN Dispersions for Topical Application" Rheological Characterization. European Journal of Pharmaceutics and Biopharmaceutics. 58. 2004. pp. 561-567.
Lupo, "Antioxidants and Vitamins in Cosmetics", Clinics in Dermatology, 19:467-473 (2001).
Martindale. 33 ed. London, Bath Press, 2002. pp. 1073 and 1473.
Merck index, 10th edition, Merck & Co., Inc.: Rahway, NJ, 1983, pp. 39 (entry 242 for allantoin).
Merck index, 14th edition, O'Neill, ed., 2006, entry for p-amino benzoic acid.
Merck index, 14th edition, O'Neill, ed., 2006, entry for zinc oxide.
Merck Index, An Encyclopedia of Chemicals, Drugs, and Biologicals. 13th Edition. O'Neil et al eds. Entries 1058, 2350, 6143, and 8803. 2001. 7 pages.
Merck Manual Home Edition. "Excessive Sweating: Sweating Disorders." Accessed Apr. 14, 2011 at www.merckmanuals.com/home/print/sec18/ch206/ch206c.html. 2 pages.
Merriam Webster Online Dictionary [online] retrieved from http://www.merriam-webster.com/cgi-bin/dictionary?book=dictionary&va=derivative on Jul. 5, 2008; 1 page.

(56) References Cited

OTHER PUBLICATIONS

Messenger, et al., "Minoxidil: Mechanisms of Action on Hair Growth", British Journal of Dermatology, 150:186-194 (2004).
Metz, et al., "A Phase I Study of Topical Tempol for the Prevention of Alopecia Induced by Whole Brain Radiotherapy", Clinical Cancer Research, 10:6411-6417 (2004).
Meucci, et al., "Ascorbic Acid Stability in Aqueous Solutions", Acta Vitaminol Enzymol, 7(3-4):147-153 (1985)—Abstract, 1 page.
MMP Inc. International Development and Manufacturing, "Formulating specialities," http://mmpinc.com, 3 pages. Feb. 2, 2010.
Molan, Peter Clark, "World Wide Wounds," Dec. 2001, 13 pages.
Neutrogena. Http://www.cosmetoscope.com/2010/04/neutrogena-clinical-with-johnson-johnsons-cytomimic-techology/. Published Apr. 28, 2010. Accessed Sep. 11, 2010, 5 pages.
Nietz, "Molecular orientation at surfaces of solids," J. Phys. Chem., 1928, 32(2): 255-269.
No Author Listed. "Opitmization of Nano-Emulsions Production by Microfluidization." European Food Research and Technology. vol. 225, No. 5-6. Sep. 2007. Abstract. 1 page.
Office Action for U.S. Appl. No. 11/430,437, Tamarkin et al., dated May 9, 2008, 27 pages.
Office Action received from the U.S. Patent Office, U.S. Appl. No. 11/430,599, dated Jul. 28, 2008 (59 pages).
Oil. Dictionary of Chemistry. Editor: DWA Sharp. Copyright 1990.
Olsen, et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, 57:767-774 (2007).
Padhi et al., "Phospho-olicines as positive-electrode materials for rechargeable lithium batteries," J. Electrochemical Soc., 1997, 144(4): 1188-1194.
Pakpayat, et al., "Formulation of Ascorbic Acid Microemulstions with Alkyl Polyglycosides", European Journal of Pharmaceutics and Biopharmaceutics, 72:444-452 (2009).
Paula. http://ww.cosmeticscop.com/cosmetic-ingredient-dictionary/definition/259/c12-15-alkyl-benzoate.aspx. Printed Oct. 24, 2010. 1 page.
Prescription Information for Aldara, Mar. 2007 (29 pages).
Prevent. (2007). In the American Heritage Dictionary of the English Language. Retrieved from http://www.credoreference.com/entry/hmdictenglang/prevent. 1 page.
Psoriasis, http://www.quickcare.org/skin/causes-of0psoriasis.html. Accessed Sep. 9, 2010—3 pages.
Purcell, Hal C. "Natural Jojoba Oil Versus Dryness and Free Radicals." Cosmetics and Toiletries Manufacture Worldwide. 1988. 4 pages.
Raschke, et al., "Topical Activity of Ascorbic Acid: From In Vitro Optimization to In Vivo Efficacy", Skin Pharmacology and Physiology, 17(4):200-206 (2004)—Abstract, 1 page.
Ravet et al., "Electroactivity of natural and synthetic triphylite," J. of Power Sources, 2001, 97-98: 503-507.
Raymond, Iodine as an Aerial Disinfectant, Journal of Hygiene, vol. 44, No. 5 (May 1946), pp. 359-361.
Receptacle. Merriam Webster. Http://www.merriam-webster.com/dictionary/receptacle. Accessed Jul. 12, 2011. 1 page.
Richwald, "Imiquimod", Drugs Today, 35(7):497 (1999)—Abstract, 1 page.
Rieger and Rhein. "Emulsifier Selection/HLB." Surfactants in Cosmetics. 1997 (no month given). 1 page.
Rosacea, http://clinuvel.com/skin-conditions/common-skin-conditions/rosacea#h0-6-prevention. Accessed Sep. 9, 2010, 5 pages.
Schulze, M.D., Harry "Iodine and Sodium Hypochlorite as Wound Disinfectants," The British Medical Journal, pp. 921-922, 1915.
Scientific Discussion for the approval of Aldara, EMEA 2005 (10 pages).
Seborrheic Dermatitis, http://www.cumc.columbia.edu/student/health/pdf/R-S/Seborrhea%20Dermatitis.pdf. Access Sep. 9, 2010, 2 pages.
Sheu, et al., "Effect of Tocopheryl Polyethylene Glycol Succinate on the Percutaneous Penetration of Minoxidil from Water/Ethanol/Polyethylene Glycol 400 Solutions", Drug Dev. Ind. Pharm., 32(5):595-607 (2006)—Abstract, 1 page.
Shim, et al., "Transdermal Delivery of Mixnoxidil with Block Copolymer Nanoparticles", J. Control Release, 97(3):477-484 (2004)—Abstract, 1 page.
Shrestha et al., Forming properties of monoglycerol fatty acid esters in nonpolar oil systems, Langmuir, 2006, 22: 8337-8345.
Silicone. Definition. Retrieved Apr. 19, 2011 from http://www.oxforddictionaries.com/definition/silicone?view=uk. 1 page.
Simovic, S. et al., "The influence of Processing Variables on Performance of O/W Emulsion Gels Based on Polymeric Emulsifier (Pemulen OTR-2NF)," International Journal of Cosmetic Science, vol. 2(2): abstract only. Dec. 24, 2001, 1 page.
Skin Deep Cosmetics. PPG-40-PEG-60 Lanolin Oil http://www.cosmeticsdatabase.com/ingredient/722972/PPG-40-PEG-60_Lanolin_Oil/?ingred06=722972. 3pages.
Smith, Anne. "Sore Nipples." Breastfeeding Mom's Sore Nipples: Breastfeeding Basics. http://breastfeedingbasics.com/articles/sore-nipples. Accessed Feb. 8, 2012. 9 pages.
Sonneville-Aubrun, O. et al. "Nanoemulsions: A New Vehicle for Skincare Products." Advances in Colloid and Interface Science. 108-109.. 2004. pp. 145-149.
Sreenivasa, et al., "Preparation and Evaluation of Minoxidil Gels for Topical Application in Alopecia", Indian Journal of Pharmaceutical Sciences, 68(4):432-436 (2006), 11 pages.
Stehle et al., Uptake of minoxidil from a new foam formulation devoid of propylene glycol to hamster ear hair follicles, J. Invest. Dermatol., 2005, 124(4), A101.
Sugisaka, et al., "The Physiochemical Properties of Imiquimod, the First Imidazoquinoline Immune Response Modifier", Abstract 3030, Pharmaceutical Research, vol. 14, No. 11 Supplemental (November), p. S475 (1997), 2 pages.
Surfactant. Chemistry Glossary. Http://chemistry.about.com/od/chemistryglossary/g/surfactant.htm, 2012, 1 page.
Sweetman, Sean C. Martindale: The Complete Drug Reference. 33rd Edition. London. Pharmaceutical Press. Jun. 21, 2002. pp. 1073 and 1473. 5 pages.
Tadros, Tharwat F. "Surfactants in Nano-Emulsions." Applied Surfactants: Principles and Applications. Wiley-VCH Verlag GmbH & Co. Weinheim. ISBN: 3-527-30629-3. 2005. pp. 285-308.
Tanhehco, "Potassium Channel Modulators as Anti-Inflammatory Agents", Expert Opinion on Therapeutic Patents, 11(7):1137-1145 (2001)—Abstract, 3 pages.
Tata, et al., "Penetration of Minoxidil from Ethanol Propylene Glycol Solutions: Effect of Application Volume on Occlusion", Journal of Pharmaceutical Sciences, 84(6):688-691 (1995).
Tata, et al., "Relative Influence of Ethanol and Propylene Glycol Cosolvents on Deposition of Minoxidil into the Skin", Journal of Pharmaceutical Sciences, 83(10):1508-1510 (1994).
Third Party Submission for U.S. Appl. No. 12/014,088, Feb. 4, 2009, 4 pages.
Trofatter, "imiquimod in clinical Practice", European Journal of Dermatology, 8(7 Supp.):17-19 (1998)—Abstract, 1 page.
Tsai, et al., "Drug and Vehicle Deposition from Topical Applications: Use of In Vitro Mass Balance Technique with Minosidil Solutions", J. Pharm. Sci., 81(8):736-743 (1992)—Abstract, 1 page.
Tsai, et al., "Effect of Minoxidil Concentration on the Deposition of Drug and Vehicle into the Skin", International Journal of Pharmaceutics, 96(1-3):111-117 (1993)—Abstract, 1 page.
Tsai, et al., "Influence of Application Time and Formulation Reapplication on the Delivery of Minoxidil through Hairless Mouse Skin as Measured in Franz Diffusion Cells", Skin Pharmacol., 7:270-277 (1994).
Tyring, "Immune-Response Modifiers: A New Paradigm in the Treatment of Human Papillomavirus", Current Therapeutic Research, 61(9):584-596 (2000)—Abstract, 1 page.
Tzen, Jason T.C. et al. "Surface Structure and Properties of Plant Seed Oil Bodies." Department of Botany and Plant Sciences, University of California, Riverside, California 92521. Apr. 15, 1992. 9 pages.

(56) References Cited

OTHER PUBLICATIONS

Uner, M. et al. "Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel." Pharmazie. 60. 2005. 5 pages.
Veron, et al., "Stability of Minoxidil Topical Formulations", Ciencia Pharmaceutica, 2(6):411-414 (1992), Abstract, 1 page.
Wermuth, C.G. "Similarity in drugs: reflections on analogue design," Drug Discovery Today, vol. 11, Nos. 7/8, Apr. 2006, pp. 348-354.
Williams, "Scale up of an olive/water cream containing 40% diethylene glycol momoethyl ether", Dev. Ind. Pharm., 26(1):71-77 (2000).
Yamada and Chung, "Crystal Chemistry of the Olivine-Type Li(Mn$_y$Fe$_{1-y}$)PO$_4$ and (Mn$_y$Fe$_{1-y}$)PO$_4$ as Possible 4 V Cathode Materials for Lithium Batteries," *J. Electrochemical Soc.*, 2001, 148(8): A960-967.
"Coal tars and coal-tar pitches," *Report on Carcinogens, Twelfth Edition*, 2011, 3 pages.
Adisen et al. "Topical tetracycline in the treatment of acne vulgaris," *J Drugs Dermatol.*, 2008, 7:953-5.
Baskaran et al., "Poloxamer-188 improves capillary blood flow and tissue viability in a cutaneous burn wound," *J. Surg. Res.*, 2001, 101(1):56-61.
Bell-Syer et al. "A systematic review of oral treatments for fungal infections of the skin of the feet," *J. Dermatolog. Treat.*, 2001, 12:69-74.
Boehm et al. 1994, "Synthesis of high specific activity [.sup.3 H]-9-cis-retinoic acid and its application for identifying retinoids with unusual binding properties," *J. Med. Chem.*, 37:408-414.
Carapeti et al., "Topical diltiazem and bethanechol decrease anal sphincter pressure and heal anal fissures without side effects," *Dis Colon Rectum*, 2000, 43(10):1359-62.
Cook and Mortensen, "Nifedipine for treatment of anal fissures," *Dis Colon Rectum*, 2000, 43(3):430-1.
Dumortier et al., "A review of poloxamer 407 pharmaceutical and pharmacological characteristics," *Pharmaceutical Res.*, 2006, 23(12):2709-2728.
Ebadi et al., "Healing effect of topical nifedipine on skin wounds of diabetic rats," *DARU*, 2003, 11(1):19-22.
Effendy and Maibach. "Surfactants and Experimental Irritant Contact Dermatitis." *Contact Dermatol.*, 1995, 33:217-225.
Elias and Ghadially, "The aged epidermal permeability barrier," *Clinical Geriatric Medicine*, Feb. 2002, pp. 103-120.
Fantin et al., "Critical influence of resistance to streptogramin B-type antibiotics on activity of RP 59500 (Quinupristin-dalfopristin) in experimental endocarditis due to *Staphylococcus aureus*," *Antimicrob Agents and Chemothery*, 1999, 39:400-405.
Fluhr et al., "Glycerol accelerates recovery of barrier function in vivo," *Acta Derm. Venereol,*. 1999, 79:418-21.
Garti et al. "Sucrose Esters microemulsions," *J. Molec. Liquids*, 1999, 80:253-296.
Hammer et al. "Anti-Microbial Activity of Essential Oils and other Plant extracts," *J. Applied Microbiology*, 1999, 86:985-990.
Hwang et al. "Isolation and identification of mosquito repellents in *Artemisia vulgaris,*" *J. Chem. Ecol.*, 11: 1297-1306, 1985.
Knight et al., "Topical diltiazem ointment in the treatment of chronic anal fissure," *Br. J. Surg.*, 2001, 88(4):553-6.
Kucharekova et al., "Effect of a lipid-rich emollient containing ceramide 3 in experimentally induced skin barrier dysfunction," *Contact Dermatitis*, Jun. 2002, pp. 331-338.
Leive et al, "Tetracyclines of various hydrophobicities as a probe for permeability of *Escherichia coli* outer membrane," *Antimicrobial Agents and Chemotherapy*, 1984, 25:539-544.
Luepke and Kemper, "The HET-CAM Test: An Alternative to the Draize Eye Test," *FD Chem. Toxic.*, 1986, 24:495-196.
Osborne and Henke, "Skin Penetration Enhancers Cited in the Technical Literature," *Pharm. Technology*, Nov. 1997, pp. 58-86.
Padi. "Minocycline prevents the development of neuropathic pain, but not acute pain: possible anti-inflammatory and antioxidant mechanisms," *Eur J. Pharmacol*, 2008, 601:79-87.

Palamaras and Kyriakis, "Calcium antagonists in dermatology: a review of the evidence and research-based studies," *Derm. Online Journal*, 2005, 11(2):8.
Passi et al., Lipophilic antioxidants in human sebum and aging, *Free Radical Research*, 2002, pp. 471-477.
Perrotti et al., "Topical Nifedipine With Lidocaine Ointment vs. Active Control for Treatment of Chronic Anal Fissure," *Dis Colon Rectum*, 2002, 45(11):1468-1475.
Repa et al. "All-trans-retinol is a ligand for the retinoic acid receptors," *Proc. Natl. Acad Sci, USA*, 90: 7293-7297, 1993.
Ruledge, "Some corrections to the record on insect repellents and attractants," *J. Am. Mosquito Control Assoc*, 1988, 4(4): 414-425.
Sakai et al., "Characterization of the physical properties of the stratum corneum by a new tactile sensor," *Skin Research and Technology*, Aug. 2000, pp. 128-134.
Schaefer, "Silicone Surfactants," *Tenside, Surfactants, Deterg.*, 1990, 27(3): 154-158.
Simoni et al., "Retinoic acid and analogs as potent inducers of differentiation and apoptosis. New promising chemopreventive and chemotherapeutic agents in oncology," *Pure Appl Chem.*, 2001, 73(9):1437-1444.
Smith, "Hydroxy acids and skin again," *Soap Cosmetics Chemical Specialties*, 1993, pp. 54-59.
Solans et al. "Overview of basic aspects of microemulsions," Industrial Applications of Microemulsions, Solans et al Eds, New York, 1997, 66:1-17.
Squillante et al., "Codiffusion of propylene glycol and dimethyl isosorbide in hairless mouse skin," *European J. Pharm. Biopharm.*, 1998, 46(3):265-71.
Todd et al. "Volatile Silicone Fluids for Cosmetics," *91 Cosmetics and Toiletries*, 1976, 27-32.
Torma et al., "Biologic activities of retinoic acid and 3, 4-dehydroretinoic acid in human keratinoacytes are similar and correlate with receptor affinities and transactivation properties," *J. Invest. Dermatology*, 1994, 102: 49-54.
USP23/NF 18 The United States Pharmacopeia: The National Formulary, US Pharmacopoeia, 1995, p. 10-14.
Van Slyke, "On the measurement of buffer values and on the relationship of buffer value to the dissociation constant of the buffer and the concentration and reaction of the buffer solution," *J. Biol. Chem.*, 1922, 52:525-570.
Van Cutsem et al., "The antiinflammatory efects of ketoconazole," *J. Am. Acad. Dermatol.*,1991, 25(2 pt 1):257-261.
Wang and Chen, "Preparation and surface active properties of biodegradable dextrin derivative surfactants," *Colloids and Surfaces A: Physicochemical and Engineering Aspects*, 2006, 281(1-3):190-193.
Weindl et al., "Hyaluronic acid in the treatment and prevention of skin diseases: molecular biological, pharmaceutical and clinical aspects," *Skin Pharmacology and Physiology*, 2004, 17: 207-213.
Xynos et al., "Effect of nifedipine on rectoanal motility," *Dis Colon Rectum*, 1996, 39(2):212-216.
Yamada et al., "Candesartan, an angiotensin II receptor antagonist, suppresses pancreatic inflammation and fibrosis in rats," *J. Pharmacol. Exp. Ther.*, 2003, 307(1)17-23.
Paragraph E.3.1 of regulation (EC) No. 2003 (See Directive 67/548/ EEC OJ 196, 16.8, 1967, p. 1.
Tzen et al., Lipids, proteins and structure of seed oil bodies from diverse species; *Plant Physiol.*, 1993, 101:267-276.
Brown et al. "Structural dependence of flavonoid interactions with Cu2+ inos: implications for their antioxidant properties," *Biochem. J.*, 1998, 330:1173-1178.
Cloez-Tayarani. et al., "Differential effect of serotonin on cytokine production in lipopolysaccharide-stimulated human peripheral blood mononuclear cells: involvement of 5-hydroxytryptamine2A receptors," *Int. Immunol.*, 2003, 15:233-40.
"Mineral oil USP," Chemical Abstracts Service Registry No. 8012-95-1, 2011, 7 pages.
"Tea tree oil," Chemical Abstract No. 68647-73-4, 2012, 2 pages.
Lin et al., "Ferulic acid stabilizes a solution of vitamins c and e and doubles its protoprotection of skin," *J Invest Dermatol*, 2005, 125:826-32.

(56) References Cited

OTHER PUBLICATIONS

"Arquad HTL8-MS,"AkzoNobel Functional Applications, retrieved on Mar. 18, 2013, Retrieved from the Internet: <URL: http://sc.akzonobel.com/en/fa/Pages/product-detail.aspx?prodID=8764>, 1 page.
"Can tuberous sclerosis be prevented?," Sharecare, 2002, retrieved on Aug. 29, 2013, <URL: http://www.sharecare.com/health/autosomal-dominant-genetic-disorders/can-tuberous-sclerosis-be-prevented;jsessionid=850579B60520A907DE75930E061E60E6>, 2 pages.
"Crohn's Disease," *Merch Manual Home Edition*, retrieved on Jan. 16, 2013, <http://www.merckmanuals.com/home/digestive_disorders/inflammatory_bowel_diseases_ibd/crohn_disease.html?qt=crohn's disease&alt=sh>, 3 pages.
"Dacarbazine," *Chemical Book*, 2010, retrieved on Oct. 18, 2013, <URL: http://www.chemicalbook.com/ChemicalProductProperty_EN_CB7710656.htm>, 2 pages.
"Drug Index (Professional)—Dacarbazine," *BC Cancer Agency*, Jun. 2004, retrieved on Oct. 18, 2013, <URL:http://www.bccancer.bc.ca/HPI/DrugDatabase/DrugIndexPro/Dacarbazine.htm>, 6 pages.
"Fully refined paraffin waxes (FRP Wax)," *Industrial Raw Materials LLC*, Feb. 21, 2008, retrieved on Aug. 22, 2013, <http://irmwax.com/Wax/Paraffin/fully_refined.asp> 1 page.
"Gas Gangrene," Merch Manual Home Edition, 2008, retrieved on Jan. 16, 2013, <http://www.merckmanuals.com/home/infections/bacterial_infections/gas_gangrene.html?qt=gasgangrene&alt=sh>1 page.
"Human Immunodeficiency Virus Infection," Merch Manual Home Edition, 2008, retrieved on Jan. 16, 2013, <http://www.merckmanuals.com/home/infections/human_immunodeficiency_virus_hiv_infection/human_immunodeficiency_virus_infection.html?qt=human immunodeficiency virus infection&alt=sh>, 11 pages.
"Minocycline (DB01017)," DrugBank, Feb 8, 2013, retrieved on Aug. 15, 2013, <http://www.drugbank.ca/drugs/DB01017>, 10 pages.
"New Nanomaterials to deliver anticancer drugs to cells developed," *Science Daily*, Jun. 2007, retrieved on Oct. 14, 2013, <URL: http://www.sciencedaily.com/releases/2007/06/070607112931.htm>, 3 pages.
"Product Data Sheet for Meclocycline," *bioaustralis fine chemicals*, Jun. 28, 2013, 1 page.
"Shear," Vocabulary.com, retrieved on Aug. 23, 2013, <URL: https://www.vocabulary.com/dictionary/shear>, 3 pages.
"Sheer," Vocabulary.com, retrieved on Aug. 23, 2013, <URL: https://www.vocabulary.com/dictionary/sheer>, 3 pages.
"View of NCT01171326 on Dec. 7, 2010," ClinicalTrials.gov_archive, Dec. 7, 2010, retrieved on Sep. 9, 2013, <http://clinicaltrials.gov/archive/NCT01171326/2010_12_07>, 4 pages.
"View of NCT01362010 on Jun. 9, 2011," ClinicalTrials.gov_archive, Jun. 9, 2011, retrieved on Sep. 9, 2013, <http://clinicaltrials.gov/archive/NCT01362010/2011_06_09>, 3 pages.
"What is TSC?," *Tuberous Sclerosis Alliance*, Jan. 1, 2005, retrieved on Feb. 6, 2014, <URL: http://www.tsalliance.org.pages.aspx?content=2>, 3 pages.
Abrams et al., "Ciclopirox gel treatment of scalp seborrheic dermatitis," Hydroxy-Piridones as Antifungal Agents with Special Emphasis on Onychomycosis, 1999, Chapter 8, 45-50.
Blaney and Cook, "Topical use of tetracycline in the treatment of acne," Arch Dermatol, Jul. 1976, 112:971-973.
Chevrant-Breton, et al., "Etude du Traitement Capillaire <<Bioscalin>> dans les Alopecies Diffuses de la Femme", Gazette Medicale, 93(17):75-79 (1986) [English abstract only].
Cunha, "Minocycline versus Doxycycline in the treatment of Lyme Neuroborreliosis," Clin. Infect. Diseases, 2000, 30: 237-238.
Durian et al., "Scaling behavior in shaving cream," The Americal Physical Society, Dec. 1991, 44(12):R7902-7905.
Google search strategy for minocycline solubility, retrieved on Aug. 15, 2013, <http://www.googl.com/search?rls=com.microsoft%3Aen-us%3AIE-SearchBox&q-melocycline+solubility>, 1 page.
Harry, "Skin Penetration," The British Journal of Dermatology and Syphillis, 1941, 53:65-82.
Lee et al., "Historical review of melanoma treatment and outcomes," Clinics in Dermatology, 2013, 31: 141-147.

Livingstone and Hubel, "Segregation of form, color, movement, and depth: Anatomy, physiology, and perception," Science, May 1988, 240:740-749.
*Molins PLC v. Textron Inc.*, 48 F.3d 1172, 33 USPQ2d 1823 (Fed. Cir. 1995), 19 pages.
Natural Skincare Authority, "Disodium EDTA: Cosmetic Toxin Data," 2011, retrieved on Nov. 17, 2013, http://www.natural-skincare-authority.com/DISODIUM-EDTA.html, 4 pages.
Neves et al., "Rheological Properties of Vaginal Hydrophilic Polymer Gels," Current Drug Delivery, 2009, 6:83-92.
Prud'homme et al., Foams: theory, measurements and applications, Marcel Dekker, Inc., 1996, 327-328.
Purdy et al., "Transfusion-transmitted malaria: unpreventable by current donor exclusion guidelines?" Transfusion, Mar. 2004, 44:464.
Reregistration Eligibility Decision for Pyrethrins, EPA, Jun. 7, 2006, 108 pages.
Schmolka, "A review of block polymer surfactants," *Journal of the American Oil Chemists Society*, Mar. 1977, 54: 110-116.
Schott, "Rheology," *Remington's Pharmaceutical Sciences*, 17th Edition, 1985, 330-345.
Sciarra, "Aerosol Technology," Kirk-Othmer Encyclopedia of Chemical Technology, Jul. 2012, 20 pages.
Scully et al., "Cancers of the oral mucosa treatment and management," Medscape Drugs, Diseases and Procedures, Apr. 20, 2012, retrieved on Oct. 12, 2013, <http://emedicine.medscape.com/article/1075729-treatment>, 10 pages.
Sehgal, " Ciclopirox: a new topical pyrodonium antimycotic agent: A double-blind study in superficial dermatomycoses," British Journal of Dermatology, 1976, 95:83-88.
Softemul-165: Product Data Sheet, Mohini Organics PVT LTD, retrieved Apr. 10, 2014, http://www.mohiniorganics.com/Softemull65.html#, 1 page.
*Sun Pharmaceutical Industried Ltd. v. Eli Lilly and Co.*, 611 F.3d 1381, 95 USPQ2d 1797 (Fed. Cir. 2010),7 pages.
Tavss et al., "Anionic detergent-induced skin irritation and anionic detergent-induced pH rise of bovine serum albumin," J. Soc. Cosmet. Chem., Jul./Aug. 1988, 39:267-272.
Tirmula et al., "Abstract: D28.00011: Enhanced order in thinfilms of Pluronic (A-B-A) and Brij (A-B) Block copolymers blended with poly (acrylic acid)," Session D28: Block Copolymer Thin Films, Mar. 13, 2006, 1 page, Abstract.
"Alcohol," Wikipedia, the free encyclopeida, retrieved on May 17, 2014, http://en.wikipedia.org/wiki/Alcohol, 17 pages.
Cole and Gazewood, "Diagnosis and Treatment of Impetigo," *Am Fam Physician*, Mar. 15, 2007, 75(6):859-864.
Oranje et al., "Topical retapamulin ointment, 1%, versus sodium fusidate ointment, 2%, for impetigo: a randomized, observer-blinded, noninferiority study," *Dermatology*, 2007, 215(4):331-340.
Clobetasol Propionate Cream and Ointment, Apr. 2006, retrieved Jul. 3, 2014, http://dailymed.nlm.nih.gov/dailymed/archives/fdaDrugInfo.cfm?archiveid=994, 7 pages.
Gels, UNC, The Pharmaceutics and Compounding Laboratory, retrieved on Aug. 25, 2014, http://pharmlabs.unc.edu/labs/gels/agents/htm, 4 pages.
Griffin, "Calculation of HLB Values of Non-Ionic Surfactants," Journal of the Society of Cosmetic Chemists, May 14, 1954, 249-256.
Klucel Hydroxypropylcellulose; Chemical and Physical Properties, Hercules Limited, copyright 1986, retrieved on Aug. 25, 2014, http://legacy.library.ucsf.edu/tid/cnf81a99/pdf, 35 pages.
Le Vine et al., "Components of the Goeckerman Regimen," Journal of Investigative Dermatology, 1979, 73:170-173.
Omega-9 Fatty Acids (Oleic Acid), Orthomolecular.org, Dec. 2004, retrieved on Aug. 15, 2014, http://orthomolecular.org/nutrients/omega9.html. 1 page.
Polystyrene, Wikipedia the free encyclopedia, retrieved Apr. 21, 2014, http://web.archive.org/web/20060312210423/http://en.wikipedia.org/wiki/Polystyrene, 4 pages.
Vera et al., "Scattering optics of Foam," Applied Optics, Aug. 20, 2001, 40(24):4210-4214.
Al-Mughrabi et al., "Effectiveness of Essential Oils and Their Combinations with Aluminum Starch Octenylsuccinate on Potato Storage Pathogens," TEOP, 2013, 16(1):23-31.

(56) References Cited

OTHER PUBLICATIONS

Beauty Banter, "Interesting list of comedogenic ingredients!!!!!!!!!!!!" QVC blog, Interesting list of comedogenic ingredients, 2014, 1-14.
Chemical Characteristics, The Olive Oil Source, © 1998-2015, retrieved on Jun. 12, 2015, http://www.oliveoilsource.com/page/chemical-characteristics, 10 pages.
CODEX Standard for Olive Oils and Olive Pomace Oils CODEX Stan 33-1981, Adopted in 1981, recently amended 2013, 8 pages.
Communication of a Notice of Opposition in European Application No. 03772600.7, dated Jan. 13, 2015, 36 pages.
Cremophor A Grades, BASF The Chemical Company, Jan. 2008, 6 pages.
Devos and Miller, "Antisense Oligonucleotides: Treating neurodegeneration at the Level of RNA," Neurotherapeutics, 2013, 10:486-497.
Ellis et al., "The Treatment of Psoriasis with Liquor Carbonis Detergens," J. Invest Dermatology, 1948, 10:455-459.
Luviquat Polymer Grades, BASF The Chemical Company, May 2012, 32 pages.
Mailer, "Chemistry and quality of olive oil," NSW Dept. of Primary Industries, Aug. 2006, Primefact 227, 1-4.
Material Safety Data Sheet, Luvitol EHO, Caelo, Nov. 28, 2013, 4 pages.
Material Safety Data Sheet, Liquor carbonis detergens, Caelo, Nov. 28, 2013, 5 pages.
Material Safety Data Sheet, Mineral Oil, Macron Fine Chemicals, Oct. 24, 2011, 6 pages.
Oh et al., "Antimicrobial activity of ethanol, glycerol monolaurate or lactic acid against Listeria moncylogenes," Int. J. Food Microbiology, 1993, 20:239-246.
Permethrin (Insecticide), Wildpro, retrieved on Jun. 4, 2015, http://widlpro.twycrosszoo.org/S/00Chem/ChComplex/perm.htm, 5 pages.
Refina, "Viscosity Guide for Paints, Petroleum & Food Products," accessed Mar. 4, 2015, http://www.refina.co.uk/webpdfs/info_docs/Viscosity_guide_chart.pdf, 2 pages.
Rohstoffinformationen, Hoffmann Mineral, 2008, 8 pages (with English translation).
Thorgeirsdottir et al., "Antimicrobial activity of monocaprin: a monoglyceride with potential use as a denture disinfectant," Acta Odontologica Scandinavica, Feb. 2006, 64:21-26 (Abstract only).
United States Standards for Grades of Olive Oil and Olive-Pomace Oil, United States Dept. of Agriculture, Oct. 25, 2010, 21 pages.
WebMD, "Psoriasis Health Center," 2014, retrieved Apr. 13, 2015, http://www.webmd.com/skin-problems-and-treatments/psoriasis/psoriasis-symptoms, 3 pages.
WebMD, "Understanding Rosacea—the Basics," 2014, retrieved Apr. 13, 2015, http://www.webmd.com/skin-problems-and-treatments/understanding-rosacea-basics, 5 pages.
Williams et al., "Acne vulgaris," Lancet, 2012, 379:361-372.
Ziolkowsky, "Moderne Aerosolschaume in der Kosmetik (Modern Aerosol Foams in Chemical and Marketing Aspects),", Seifen-Ole-Fette-Wachse, Aug. 1986, 112(13): 427-429 (with English translation).
Haw, "The HLB System: A Time Saving Guide to Surfactant Selection," Presentation to the Midwest Chapter of the Society of Cosmetic Chemists, Mar. 9, 2004, 39 pages.
Allantoin, Römpp Online, retrieved on Sep. 23, 2015, https://roempp.thieme.de/roempp4.0/do/data/RD-O 1-01552, 5 pages.
Coconut Oil, Wikipedia, the free encyclopedia, retrieved on Jul. 3, 2015, https://en.wikipedia.org/wiki/Coconut_oil, 8 pages.
Communication of a Notice of Opposition in European Application No. 03772600.7, dated Sep. 24, 2015, 30 pages.
Communication of a Notice of Opposition in European Application No. 03772600.7, dated Sep. 23, 2015, 42 pages.
Diethyltoluamid, Wikipedia, the free encyclopedia, retrieved on Sep. 11, 2015, https://de.wikipedia.org/wiki/Diethyltoluamid, 12 pages.
Dimethylphthalate, Wikipedia, the free encyclopedia, retrieved on Sep. 11, 2015, http://de.wikipedia.org/wiki/Dimethylphthalat, 8 pages.

Everything but the Olive, (the Olive Oil Source 1998-2016). http://www.oliveoilsource.com/pageAchemical-characteristics).
Healy, "Gelled Emollient Systems for Controlled Fragrance Release and Enhanced Product Performance," Cosmetics and toiletries, 2002, 117(2): 47-54.
Lamisil, Lamisil.http://www.fda.gov/downloads/Drugs/DrugSafety/PostmarketDrugSafetyInformationforPatientsandProviders/ucm052213.pdf, Published: Apr. 2001.
Leunapon-F, Leuna-Tenside, Screenshot, retrieved on Sep. 18, 2015, http://www.leuna-tenside.de/2006_7_14_3143/2006_8_7 5750/2006_8_7 241/cas-68439-49-6, 1 page.
Mead, "Electrostatic Mechanisms Underlie Neomycin Block of the Cardiac Ryanodine Receptor Channel (RyR2)," Biophysical Journal, 2004, (87): 3814-3825.
Rowe et al., "Glyceryl Monooleate," Handbook of Pharmaceutical Excipients, 2011, pp. 1-5, retrieved on Dec. 19, 2011, http://www.medicinescomplete.com/mc/excipients/current/1001938996.htm?q=glyceryl%20monooleate&t=search&ss=text&p=1# hit.
Rowe et al., "Octyldodecanol," Handbook of Pharmaceutical Excipients, 2011, pp. 1-4, retrieved on Dec. 19, 2011, URL:http://www.medicinescomplete.com/mc/excipients/current/1001942450.htm?q=octyldodecanol&t=search&ss=text&p=1# hit.
Rowe et al., "Sucrose Palmitate," Handbook of Pharmaceutical Excipients, 2011, pp. 1-5, retrieved on Dec. 19, 2011, URL:http://www.medicinescomplete.com/mc/excipients/current/EXP-TD-c46-mn0001.htm?q=sucrose%20stearate&t=search&ss=text&p=1# hit.
Rowe et al., "Sucrose Stearate," Handbook of Pharmaceutical Excipients, 2011, pp. 1-4, retrieved on Dec. 19, 2011, URL:http://www.medicinescomplete.com/mc/excipients/current/EXP-TD-c11-mnOOO1-mnOOO1.htm?q=sucrose%20stearate&t=search&ss=text&p=3# hit.
RSES (Oil in Refrigerator Systems, Service Application Manual, 2009).
Security Datasheet, Luvitol EHO, Cetearyloctanoat, Nov. 27, 2013, 10 pages.
Sigma-Aldrich. http://www.sigmaaldrich.com/catalog/product/sial/p1754?lang=en® ion=. Published:Mar. 5, 2014.
Suppositories?, CareCure, http://sci.rutgers.edu/forum/showthread.php?4176-Suppositories. Published: Apr. 16, 2002.
Triethanolamine, haute.de, retrieved on Sep. 14, 2015, http://www.haut.de/service/inci/anzeige&id=16384&query=Triethanolamine&funktio . . . , 3 pages.
Valenta, "Effects of Penetration Enhancers on the In-vitro Percutaneous Absorption of Progesterone," J. Phann Pharrnacol., 1997, 49: 955-959.
Wenninger et al., "International Cosmetic Ingredient Dictionary and Handbook," The Cosmetic, Toiletry, and Fragrance Association, Washington, DC., 1997, vol. 1, 4 pages.
Williams et al., "Urea analogues in propylene glycol as penetration enhancers in human skin," International Journal of Pharmaceutics, 1989, 36, 43-50.
Wu et al., "Interaction of Fatty Acid Monolayers with Cobalt Nanoparticles," Nano Letters, 2004, 4(2): 383-386.
Kaur et al., "Formulation Development of Self Nanoemulsifying Drug Delivery System (SNEDDS) of Celecoxib for Improvement of Oral Bioavailability," Pharmacophore, 2013, 4(4):120-133.
Material Safety Data Sheet, Butane, Gas Innovations, Sep. 7, 2007, 3 pages.
Material Safety Data Sheet, Carbon Dioxide, Airgas, Feb. 11, 2016, 11 pages.
Material Safety Data Sheet, Dimethyl Ether, Airgas, May 14, 2015, 12 pages.
Material Safety Data Sheet, N-Butane, Airgas, May 7, 2015, 13 pages.
Material Safety Data Sheet, Nitrous Oxide, Airgas, Feb. 11, 2016, 11 pages.
Material Safety Data Sheet, Propane, Airgas, Oct. 20, 2015, 12 pages.
Sanders et al., "Stabilization of Aerosol Emulsions and Foams," J. Soc. Cosmet. Chem., 1970, 21:377-391.
Albrecht et al., "Topical minocycline foam for moderate to severe acne vulgaris: Phase 2 randomized double-blind, vehicle-controlled study results," J. Am. Acad. Dermatol., 2016, 74(6):1251-1252.

(56) References Cited

OTHER PUBLICATIONS

Chapter 1 Meaning of HLB Advantages and Limitations 1980; 4 pages.
Material Safety Data Sheet, Squalane, TCI America, 5 pages, https://www.spectrumchemical.com/MSDS/TC1-H0096.pdf. Published: Oct. 6, 2014.
Sorbitan Esters, [online] retrieved on Jul. 1, 2016 from: http://www.drugfuture.com/chemdata/sorbitan-esters.html 2 pages.
Sreenivasan et al., "Studies on Castor Oil. I. Fatty Acid Composition of Castor Oil," Journal of the American Oil Chemists Society. 1956, 33:61-66.
Abdullah, G.Z. et al. (Jan. 2013) "Carbopol 934, 940 and Ultrez 10 as viscosity modifiers of palm olein esters based nano-scaled emulsion containing ibuprofen" *Pak J Pharm Sci*, 26(1):75-83.
Craig, D.Q.M. et al. (Jul. 1994) "An investigation into the structure and properties of Carbopol 934 gels using dielectric spectroscopy and oscillatory rheometry" *J Controlled Rel*, 30(3):213-223 (Abstract).
European Patent Application No. 03772600.7 (Patent No. 1556009): Interlocutory Decision in Opposition Proceedings, dated Feb. 3, 2017, 54 pages.
European Patent Application No. 03772600.7 (Patent No. 1556009): Minutes of Oral Proceedings, dated Feb. 3, 2017, 6 pages.
Foamix Pharmaceuticals Ltd. (May 1, 2017) "Foamix Pharmaceuticals Announces Plans for Additional Phase 3 Trial for FMX101 in Moderate to Severe Acne," Press Release [online]. Retrieved from: http://www.foamix.co.il/news.asp?nodeID=564&itemID=204, on Jun. 12, 2017, 5 pages.
Frankel, A.J. et al. (2010) "Coal Tar 2% Foam in Combination with a Superpotent Corticosteroid Foam for Plaque Psoriasis. Case Report and Clinical Implications" *J Clin Aesthet Dermatol*, 3(10):42-45.
Ghica, M.V. et al. (2011) "Design and optimization of some collagen-minocycline based hydrogels potentially applicable for the treatment of cutaneous wound infections" *Pharmazie*, 66:853-861.
Kanicky, J.R. and D.O. Shah (2002) "Effect of Degree, Type, and Position of Unsaturation on the $pK_a$, of Long-Chain Fatty Acids" *J Colloid and Interface Science*, 256:201-207.
Kircik, L.H. and S. Kumar (Aug. 2010) "Scalp Psoriasis" *J Drugs Dermatol*, 9(8 Suppl):s101-s137.
Milton, D.T. et al. (2006) "A Phase I/II Study of Weekly High-Dose Erlotinib in Previously Treated Patients With Nonsmall Cell Lung Cancer" *Cancer*, 107:1034-1041.
Musial, W. and A. Kubis (2004) "Carbopols as factors buffering triethanolamine interacting with artificial skin sebum" *Polim Med*, 34(4):17-30 (Abstract).
Pharmaceutical Benefits Advisory Committee (PBAC) of Australia. PBAC *Public Summary Document -Nov. 2014 Meeting*(5 pages).
Penreco, "Intelligent Gel Technology Product Specifications," Rev. 06/16 (2 pages).
Promius™ Pharma LLC (2012) Scytera™ (coal tar) Foam, 2%. Product Information Sheet, 1 page.
Sigma Aldrich, "Surfactants Classified by HLB Numbers" 2017 [online]. Retrieved from the Internet: www.sigmaaldrich.com/materials-science/material-science-products.html?TablePage=22686648, on Jul. 8, 2017 (3 pages).
Solodyn® (Minocycline HCl, USP) Prescribing Information; revised Jun. 2016, 2 pages.
Sung, J.H. et al. (2010) "Gel characterisation and in vivo evaluation of minocycline-loaded wound dressing with enhanced wound healing using polyvinyl alcohol and chitosan" *Intl J Pharmaceut*, 392:232-240.
Tamarkin, D. (2013) "Foam: A Unique Delivery Vehicle for Topically Applied Formulations" in: *Formulating Topical Applications—a Practical Guide*. Dayan N, Ed., Carol Stream, IL: CT Books, Chapter 9, pp. 233-260.
Tjulandin, S. et al. (2013) "Phase I, dose-finding study of AZD8931, an inhibitor of EGRF (erbB1), HER2 (erbB2) and HER3 (erbB3) signaling, in patients with advanced solid tumors" *Invest New Drugs*, 32(11:145-153.
Water Jel Technologies, "Material Safety Data Sheet for Neomycin Antibiotic Ointment," Dec. 1, 2004, 7 pages.
WebMD (2017) "User Reviews & Ratings—Scytera topical" [online]. Retrieved Mar. 1, 2017; retrieved from the Internet: http://www.webmd.com/drugs/drugreview-151502-Scytera+topical.aspx?drugid=151502&drugname=Scyterai+topical&sortby=3 (2 pages).
Wrightson, W.R. et al. (1998) "Analysis of minocycline by high-performance liquid chromatography in tissue and serum" *J Chromatography B*, 706:358-361.
Zeichner, J.A. (2010) "Use of Topical Coal Tar Foam for the Treatment of Psoriasis in Difficult-to-treat Areas" *J Clin Aesthet Dermatol*, 3(9):37-40.
Aslam et al. (2015) "Emerging drugs for the treatment of acne" *Expert Opin Emerging Drugs*, 20:91-101.
Beuchat (Feb. 1983) "Influence of Water Activity on Growth, Metabolic Activities and Survival of Yeasts and Molds" *J Food Prot*, 46(2):135-141.
Brisaert, M. et al. (1996) "Investigation on the chemical stability of erythromycin in solutions using an optimization system" *Pharm World Sci*, 18(5):182-186.
Canavan et al. (2016) "Optimizing Non-Antibiotic Treatments for Patients with Acne: A Review" *Dermatol Ther*, 6:555-578.
Fontana (Apr. 1999) "Pharmaceutical Applications for Water Activity" Pharmaceutical Online [online]. Retrieved from https://www.pharmaceuticalonline.com/doc/pharmaceutical-applications-for-water-activit- . . . , on Jan. 17, 2018 (4 pages).
Sarpotdar, P.P. et al. (Jan. 1986) "Effect of Polyethylene Glycol 400 on the Penetration of Drugs Through Human Cadaver Skin in Vitro" *J Pharma Sci*, 75(1):26-28.

\* cited by examiner

FOAMABLE COMPOSITION COMBINING A POLAR SOLVENT AND A HYDROPHOBIC CARRIER

CROSS REFERENCE TO RELATED APPLICATIONS

This application claims the benefit under 35 U.S.C. § 119(e) of U.S. Provisional Patent Application No. 60/700,702, filed on Jul. 19, 2005, entitled "Foamable Composition Combining a Polar Solvent and a Hydrophobic Carrier," which is herein incorporated by reference in its entirety.

This application is a continuation-in-part application of co-pending U.S. application Ser. No. 11/124,676, filed on May 9, 2005, entitled "Vasoactive Kit and Compositions and Uses Thereof," which is a continuation-in-part application of co-pending International Patent Application No. IB03/005527, designating the United States and filed on Oct. 24, 2003, which claims the benefit of priority under 35 U.S.C. § 119(e) to U.S. Patent Application Ser. No. 60/429, 546, filed on Nov. 29, 2002, both entitled "Cosmetic and Pharmaceutical Foam," and which claims the benefit of priority under 35 U.S.C. § 119(a) to Israeli Patent Application No. 152486, filed Oct. 25, 2002, all of which are hereby incorporated in their entirety by reference.

This application is also a continuation-in-part application of co-pending U.S. patent application Ser. No. 10/911,367, filed on Aug. 4, 2004, which claims the benefit of priority under 35 U.S.C. § 119(e) to U.S. Patent Application Ser. No. 60/492,385, filed on Aug. 4, 2003, both entitled "Foam Carrier Containing Amphiphilic Copolymer Gelling Agent" and both hereby incorporated in their entirety by reference.

This application is also a continuation-in-part application of co-pending U.S. patent application Ser. No. 10/835,505, filed on Apr. 28, 2004, which claims the benefit of priority under 35 U.S.C. § 119(e) to U.S. Patent Application Ser. No. 60/530,015, filed on Dec. 16, 2003, and U.S. Patent Application Ser. No. 60/492,385, filed on Aug. 4, 2003, all entitled "Oleaginous Pharmaceutical and Cosmetic Foam" and all hereby incorporated in their entirety by reference.

This application is also a continuation-in-part application of co-pending U.S. patent application Ser. No. 10/922,358, filed Aug. 20, 2004, entitled "Penetrating Pharmaceutical Foam," which claims the benefit of priority under 35 U.S.C. § 119(e) to U.S. Patent Application Ser. No. 60/497, 648, filed on Aug. 25, 2003, both of which are incorporated by reference.

BACKGROUND OF THE INVENTION

This invention relates to foamable pharmaceutical and cosmetic compositions.

Foams and, in particular, foam emulsions are complicated systems which do not form under all circumstances. Changes in foam emulsion composition, such as by the addition of active ingredients may destabilize the foam. There is therefore a need for a foam composition which provides desirable properties to the skin and can remain stable whilst accommodating a variety of active ingredients.

U.S. Pat. No. 6,126,920 ("the '920 patent") discloses treatment of various skin diseases, and in particular, scalp psoriasis, using a foamable pharmaceutical composition containing a corticosteroid active substance, an aliphatic alcohol, water, a fatty alcohol, a surface-active agent, a propellant and a buffering agent. The foamable composition contains 40-90% w/w composition of an aliphatic alcohol. The '920 patent is typical of many compositions that use aliphatic alcohols in the foam composition. The alcohol promotes fast drying and thereby attempts to address the sticky feeling left by many topical formulations after application; however, alcohols, and in particular the methyl, ethyl and isopropyl alcohols preferred in the '920 patent, are defatting agents and may cause skin to become dry and cracked. U.S. Pat. Application Pub. No. US2004/0151671 provides pharmaceutical compositions in a pressurized container, comprising a quick breaking alcoholic foaming agent. U.S. Pat. No. 5,783,202 provides a pediculicidal mousse composition containing a pediculicidal agent containing (a) from about 0.1 to about 10% w/w of a pediculicidal agent (b) about 70 to about 97% w/w of a foaming agent, which is preferably a quick breaking alcoholic foaming agent; and (c) from about 3 to about 20% w/w of an aerosol propellant. U.S. Pat. No. 6,730,288 teaches a pharmaceutical foam composition including (a) an active ingredient; (b) an occlusive agent; (c) an aqueous solvent; and (d) an organic cosolvent; wherein the active ingredient is insoluble in water and insoluble in both water and the occlusive agent; and wherein there is enough occlusive agent to form an occlusive layer on the skin.

A few dermatological foam products are available on the market.

Olux™ Foam, produced by Connetics, Inc., contains clobetasol propionate. Each gram of Olux™ Foam contains 0.5 mg clobetasol propionate, USP, in a thermolabile foam, which consists of ethanol (60%), purified water, propylene glycol, cetyl alcohol, stearyl alcohol, polysorbate 60, citric acid, and potassium citrate. It is dispensed from an aluminum can pressurized with a hydrocarbon propellant (propane/butane). Luxiq™ corticosteroid foam medication contains 1.2 mg betamethasone valerate per gram, in a vehicle, comprising ethanol (60.4%), purified water, propylene glycol, cetyl alcohol, stearyl alcohol, polysorbate 60, citric acid, and potassium citrate, and pressurized with a hydrocarbon propellant. Alcohol is known to impair the integrity of the skin barrier, dry the skin and cause skin irritation. The incidence skin irritation (burning, itching and stinging) as detailed the package inserts of the above mentioned products is very high (54%), probably due to the high alcohol content. Moreover, the respective incidence of skin irritation caused by the vehicle of these foams is 75%.

Thus, while alcohol is useful in solubilizing an active agent and enabling effective dermal penetration of an active agent is desirable, the development of a safe foam vehicle, which will overcome the evident skin drying and irritation caused by alcohol, is warranted.

Furthermore, foam compositions that possess a lesser degree of thermal sensitivity, thus being more useful for the treatment of large skin areas are desired.

SUMMARY OF THE INVENTION

The present invention relates to a foamable vehicle or cosmetic or pharmaceutical composition comprising:
(1) an organic carrier, at a concentration of about 10% to about 70% by weight, wherein said organic carrier concurrently comprises:
 (i) at least one hydrophobic organic carrier and
 (ii) at least one polar solvent
(2) at least one surface-active agent;
(3) water; and
(4) at least one liquefied or compressed gas propellant at a concentration of about 3% to about 25% by weight of the total composition.

The present invention further relates to said composition comprising an active agent.

In some embodiments, the foamable cosmetic or pharmaceutical composition is non-flammable, wherein said gas propellant contains hydrofluorocarbon.

The present invention further provides a method of treating, alleviating or preventing a disorder of mammalian subject, comprising administering a therapeutically effective amount of the above-mentioned compositions to an afflicted target site.

The present invention further provides use of a therapeutically effective amount of the above-mentioned compositions in the manufacture of a medicament.

The present invention further provides a therapeutically effective amount of the above-mentioned compositions for use in the manufacture of a medicament.

DETAILED DESCRIPTION OF THE INVENTION

The present invention provides a safe and effective foamable cosmetic or pharmaceutical vehicle or composition. The vehicle or composition contains a polar solvent, which can optionally be a short-chain alcohol, which possesses (as such) skin drying and skin irritation properties; however, the composition also contains a hydrophobic carrier, which counteracts these undesirable effects and overcomes these drawbacks.

In one or more embodiments, the foamable cosmetic or pharmaceutical vehicle includes:
(1) an organic carrier, at a concentration of about 10% to about 70% by weight, wherein said organic carrier concurrently comprises:
  (i) at least one hydrophobic organic carrier and
  (ii) at least one polar solvent
(2) at least one surface-active agent;
(3) water; and
(4) at least one liquefied or compressed gas propellant at a concentration of about 3% to about 25% by weight of the total composition.

In one or more embodiments the foamable cosmetic or pharmaceutical vehicle includes:
(1) an organic carrier, at a concentration of about 10% to about 70% by weight, wherein said organic carrier concurrently comprises
  (i) at least one hydrophobic organic carrier, and
  (ii) at least one polar solvent;
(2) about 0.1% to about 5% by weight of at least one surface-active agent;
(3) Water; and
(4) at least one liquefied or compressed gas propellant at a concentration of about 3% to about 25% by weight of the total composition.

In one or more embodiments a foamable cosmetic or pharmaceutical vehicle is provided wherein the ratio of the hydrophobic organic carrier and the polar solvent are selected to provide a selected pharmacological or safety property;

In one or more embodiments a foamable cosmetic or pharmaceutical vehicle is provided also incorporating a polymeric agent.

In one or more embodiments the polymeric agent is selected from a bioadhesive agent, a gelling agent, a film forming agent and a phase change agent and can be from about 0.01% to about 5% by weight In one or more embodiments, a pharmaceutical or cosmetic foamable product is provided, wherein a pharmaceutical or a cosmetic active agent is incorporated in a foamable vehicle, which contains a polar solvent and a hydrophobic organic carrier.

Thus, in one or more embodiments, the pharmaceutical or cosmetic foamable product comprises:
(1) an effective concentration of at least one pharmaceutical or cosmetic active agent;
(2) an organic carrier, at a concentration of about 10% to about 70% by weight, wherein said organic carrier concurrently comprises
  (i) at least one hydrophobic organic carrier
  (ii) at least one polar solvent;
(3) about 0.1% to about 5% by weight of at least one surface-active agent; and
(4) at least one liquefied or compressed gas propellant at a concentration of about 3% to about 25% by weight of the total composition.

In one or more embodiments of the pharmaceutical or cosmetic foamable product is non-flammable.

Water and optional ingredients are added to complete the total mass to 100%.

All % values are provided on a weight (w/w) basis.

Polar Solvent

A "polar solvent" is an organic solvent, typically soluble in both water and oil. Certain polar solvents posses the beneficial property of a humectant, being a substance, which helps retain moisture, for example propylene glycol and glycerin.

In one or more embodiments, the polar solvent is a humectant.

According to one or more embodiments, the polar solvent comprises a short chain alcohol. Short chain alcohols, having up to 5 carbon atoms in their carbon chain skeleton and one hydroxyl group, such as ethanol, propanol, isopropanol, butanol, isobutanol, t-butanol and pentanol. In one or more embodiments the concentration of the short chain alcohols is from about 5% to about 70%, preferably from about 10% to about 60%.

In one or more embodiments, the polar solvent is a polyol. Polyols are organic substances that contain at least two hydroxy groups in their molecular structure.

In one or more embodiments, the polar solvent contains an diol (a compound that contains two hydroxy groups in its molecular structure), such as propylene glycol (e.g., 1,2-propylene glycol and 1,3-propylene glycol), butanediol (e.g., 1,4-butanediol), butanediol (e.g., 1,3-butanediol and 1,4-butenediol), butynediol, pentanediol (e.g., 1,5-pentanediol), hexanediol (e.g., 1,6-hexanediol), octanediol (e.g., 1,8-octanediol), neopentyl glycol, 2-methyl-1,3-propanediol, diethylene glycol, triethylene glycol, tetraethylene glycol, dipropylene glycol and dibutylene glycol.

In one or more embodiments, the polar solvent contains a triol (a compound that contains three hydroxy groups in its molecular structure), such as glycerin and 1,2,6-Hexanetriol.

Other non-limiting examples of polar solvents include pyrrolidones, (such as N-methyl-2-pyrrolidone and 1-methyl-2-pyrrolidinone), dimethyl isosorbide, 1,2,6-hexapetriol, dimethyl sulfoxide (DMSO), ethyl proxitol, dimethylacetamide (DMAc) and alpha hydroxy acids, such as lactic acid and glycolic acid.

According to still other embodiments, the polar solvent is a polyethylene glycol (PEG) or PEG derivative that is liquid at ambient temperature, including PEG200 (MW (molecular weight) about 190-210 kD), PEG300 (MW about 285-315 kD), PEG400 (MW about 380-420 kD), PEG600 (MW about 570-630 kD) and higher MW PEGs such as PEG 4000, PEG 6000 and PEG 10000 and mixtures thereof.

Polar solvents are known to enhance the penetration of active agent into the skin and through the skin, and therefore, their inclusion in the composition of the present invention is desirable, despite their undesirable skin drying and irritation potential. There is at one level a commonality between the different polar solvents and their penetration enhancement properties. However, lower molecular weight alcohols can sometimes be more potent as a solvent, for example by extracting lipids from the skin layers more effectively, which characteristic can adversely affect the skin structure and cause dryness and irritation. Therefore the selection of the hydrophobic carrier to counteract these negative effects may be of more importance when using the lower molecular weight alcohols.

Hydrophobic Solvent

A "hydrophobic organic carrier" as used herein refers to a material having solubility in distilled water at ambient temperature of less than about 1 gm per 100 mL, more preferable less than about 0.5 gm per 100 mL, and most preferably less than about 0.1 gm per 100 mL.

The identification of a hydrophobic organic carrier or "hydrophobic solvent", as used throughout this specification synonymously, is not intended to characterize the solubilization capabilities of the solvent for any specific active agent or any other component of the foamable composition. Rather, such information is provided to aid in the identification of materials suitable for use as a hydrophobic carrier in the foamable compositions described herein.

In one or more embodiments, the hydrophobic organic carrier is a high-melting point hydrocarbon, such as, petrolatum.

In one or more other embodiments the use of high melting point hydrocarbons, such as petrolatum in concentrations of more than 10%, are not desirable since they have a waxy feeling when applied to the skin; yet, in certain additional embodiments, when an extensive refatting effect is required, then petrolatum in concentrations of more than 10%, for example between about 10% and about 50% is included in the composition of the present invention.

According to one or more embodiments, hydrophobic solvents are liquid oils originating from vegetable, marine or animal sources. Suitable liquid oil includes saturated, unsaturated or polyunsaturated oils. By way of example, the unsaturated oil may be olive oil, corn oil, soybean oil, canola oil, cottonseed oil, coconut oil, sesame oil, sunflower oil, borage seed oil, syzigium aromaticum oil, hempseed oil, herring oil, cod-liver oil, salmon oil, flaxseed oil, wheat germ oil, evening primrose oils or mixtures thereof, in any proportion.

Suitable hydrophobic solvents also include polyunsaturated oils containing poly-unsaturated fatty acids. In one or more embodiments, the unsaturated fatty acids are selected from the group of omega-3 and omega-6 fatty acids. Examples of such polyunsaturated fatty acids are linoleic and linolenic acid, gamma-linoleic acid (GLA), eicosapentaenoic acid (EPA) and docosahexaenoic acid (DHA). Such unsaturated fatty acids are known for their skin-conditioning effect, which contribute to the therapeutic benefit of the present foamable composition. Thus, the hydrophobic solvent can include at least 6% of an oil selected from omega-3 oil, omega-6 oil, and mixtures thereof.

In the context of the present invention, oils that possess therapeutically beneficial properties are termed as "therapeutically active oil."

Another class of hydrophobic solvents is the essential oils, which are also considered therapeutically active oils, and which contain active biologically occurring molecules and, upon topical application, exert a therapeutic effect. Non-limiting examples of essential oils include rosehip oil, which contain retinoids and is known to reduce acne and post-acne scars, and tea tree oil, which possess antibacterial, antifungal and antiviral properties. Other examples of essential oils are oils of anise, basil, bergemont, camphor, cardamom, carrot, canola, cassia, catnip, cedarwood, citronella, clove, cypress, eucalyptus, frankincense, garlic, ginger, grapefruit, hyssop, jasmine, jojova, lavender, lavandin, lemon, lime, mandarin, marjoram, myrrh, neroli, nutmeg, orange, peppermint, petitgrain, rosemary, sage, spearmint, star anise, tangerine, thyme vanilla, verbena and white clover.

Another class of therapeutically active oils includes liquid hydrophobic plant-derived oils, which are known to possess therapeutic benefits when applied topically.

Silicone oils also may be used and are desirable due to their known skin protective and occlusive properties. Suitable silicone oils include non-volatile silicones, such as polyalkyl siloxanes, polyaryl siloxanes, polyalkylaryl siloxanes and polyether siloxane copolymers, polydimethylsiloxanes (dimethicones) and poly(dimethylsiloxane)-(diphenylsiloxane) copolymers. Silicone oils are also considered therapeutically active oil, due to their barrier retaining and protective properties.

A further class of hydrophobic carriers includes hydrophobic liquids, selected from the family of organic liquids described as "emollients." Emollients possess a softening or soothing effect, especially when applied to body areas, such as the skin and mucosal surfaces. Examples of suitable emollients include isopropyl myristate, isopropyl palmitate, isopropyl isostearate, diisopropyl adipate, diisopropyl dimerate, maleated soybean oil, octyl palmitate, cetyl lactate, cetyl ricinoleate, tocopheryl acetate, cetyl acetate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, isononyl isononanoate, isotridecyl isononanoate, myristyl myristate, octyl dodecanol, sucrose esters of fatty acids and octyl hydroxystearate.

The foamable composition of the present invention can be an emulsion, or microemulsion, including an aqueous phase and an organic carrier phase.

One non-limiting benefit of combining a polar solvent and a hydrophobic carrier is apparent in the resulting conservation of skin barrier properties.

Another non-limiting benefit of combining a polar solvent and a hydrophobic carrier is further apparent in the reduction of skin irritation.

Another non-limiting benefit of the vehicle or composition of the present invention is to provide increased penetration of the active or beneficial agent whilst replenishing the skin for example by moisturizing or adding fats or oils.

The ratio between the polar solvent and the hydrophobic carrier is determined according to the desirable pharmacologic and safety properties of the product. Typically, the polar solvent to hydrophobic carrier ranges between about 1:4 and about 4:1, for example, about 1:4, about 1:2, about 3:4, about 1:1, about 5:4, about 4:2, about 2:1, about 3:1 and about 4:1. When high solubilization and/or enhanced dermal or transdermal delivery of a drug is desirable, the polar solvent to hydrophobic carrier is selected within the range of about 1:1 and about 4:1, for example, about 1:1, about 5:4. about 6:4, about 7:4, about 2:1, about 3:1 and about 4:1 Yet, in other case, when the need of enhanced skin protection and skin barrier build-up is more pronounced, the polar solvent to hydrophobic carrier is selected within the range of about 2:8 and about 1:1, for example, about 1:4, about 1:2, about 3:4 and about 1:1.

The following table, Table 1 exemplifies, in a non-limiting manner, pairs of polar solvent and the hydrophobic carrier, as provided in the present invention. The examples of the previous paragraph are incorporated herein by reference.

| Exemplary Polar Solvent | Exemplary Hydrophobic Carrier | Polar Solvent/ Hydrophobic Carrier Ratio | Comment |
| --- | --- | --- | --- |
| A short chain alcohol, selected from ethanol, propanol, isopropanol, butanol | A hydrophobic carrier, selected from mineral oil, petrolatum, isopropyl myristate, isopropyl palmytate, a triglyceride and silicone oil | Between about 1:4 and about 4:1. | To provide enhanced delivery of an active agent, while conserving skin barrier To provide enhanced skin barrier build-up, which facilitates the recovery of damaged skin. |
| A short chain alcohol, selected from ethanol, propanol, isopropanol, butanol | Ester of fatty acid | Between about 1:4 and about 4:1. | To provide enhanced delivery of an active agent, while conserving skin barrier To provide enhanced skin barrier build-up, which facilitates the recovery of damaged skin. |
| A short chain alcohol, selected from ethanol, propanol, isopropanol, butanol | Combination of at least one triglyceride and at least one ester of a fatty acid | Between about 1:4 and about 4:1. | To provide enhanced delivery of an active agent, while conserving skin barrier To provide enhanced skin barrier build-up, which facilitates the recovery of damaged skin. |
| A polyethylene glycol PEG | A hydrophobic carrier, selected from mineral oil, petrolatum, isopropyl myristate, isopropyl palmytate, a triglyceride and silicone oil | Between about 1:1 and about 4:1 | To provide enhanced delivery of an active agent, while conserving skin barrier |
| Dimethyl isosorbide | A hydrophobic carrier, selected from mineral oil, petrolatum, isopropyl myristate, isopropyl palmytate, a triglyceride and silicone oil | Between about 1:1 and about 4:1 | To provide enhanced delivery of an active agent, while conserving skin barrier To provide enhanced skin barrier build-up, which facilitates the recovery of damaged skin. |
| Dimethyl isosorbide | A triglyceride | Between about 4:1 and about 1:4, | To provide increased solubility of a drug, enhanced delivery and skin barrier build-up |
| Dimethyl isosorbide | Capric-caprylic triglyceride | Between about 1:4 and about 1:1 | To provide increased solubility of a drug, enhanced delivery and skin barrier build-up |
| Dimethyl isosorbide | Ester of fatty acid | Between about 1:4 and about 1:1 | To provide increased solubility of a drug, enhanced delivery and skin barrier build-up |
| Dimethyl isosorbide | Combination of at least one triglyceride and at least one ester of a fatty acid | Between about 1:4 and about 1:1 | To provide increased solubility of a drug, enhanced delivery and skin barrier build-up |
| A diol selected from the group of propylene glycol, butanediol, hexanediol, octanediol, propanediol, diethylene glycol, triethylene glycol, tetraethylene glycol, dipropylene glycol and dibutylene glycol. | A hydrophobic carrier, selected from mineral oil, petrolatum, isopropyl myristate, isopropyl palmytate, a triglyceride and silicone oil | Between about 4:1 and about 1:4 | To provide enhanced skin barrier build-up |

-continued

| Exemplary Polar Solvent | Exemplary Hydrophobic Carrier | Polar Solvent/ Hydrophobic Carrier Ratio | Comment |
|---|---|---|---|
| A triol (a compound that contains three hydroxy groups in its molecular structure), such as glycerin and 1,2,6-Hexanetriol. | A hydrophobic carrier, selected from mineral oil, petrolatum, isopropyl myristate, isopropyl palmytate, a triglyceride | Between about 4:1 and about 1:4 | To provide enhanced skin barrier build-up |
| An alpha hydroxy acids, such as lactic acid and glycolic acid | A hydrophobic carrier, selected from mineral oil, petrolatum, isopropyl myristate, isopropyl palmytate, a triglyceride | Between about 4:1 and about 1:4 | To provide enhanced skin barrier build-up |
| DMSO | A hydrophobic carrier, selected from mineral oil, petrolatum, isopropyl myristate, isopropyl palmytate, a triglyceride | Between about 4:1 and about 1:4, | To provide enhanced skin barrier build-up |
| A pyrrolidone, such as N-methyl-2-pyrrolidone and 1-methyl-2-pyrrolidinone | A hydrophobic carrier, selected from mineral oil, petrolatum, isopropyl myristate, isopropyl palmytate, a triglyceride | Between about 4:1 and about 1:4 | To provide enhanced skin barrier build-up |
| A combination of at least two polar solvents | A hydrophobic carrier, selected from mineral oil, petrolatum, isopropyl myristate, isopropyl palmytate, a triglyceride and silicone oil | Between about 1:4 and about 4:1. | To provide enhanced delivery of an active agent, while conserving skin barrier To provide enhanced skin barrier build-up, which facilitates the recovery of damaged skin. |
| A combination of at least two polar solvents | Ester of fatty acid | Between about 1:4 and about 1:1 | To provide increased solubility of a drug, enhanced delivery and skin barrier build-up |
| A combination of at least two polar solvents | Combination of at least one triglyceride and at least one ester of a fatty acid | Between about 1:4 and about 1:1 | To provide increased solubility of a drug, enhanced delivery and skin barrier build-up |

In one or more embodiments, the polar solvent consists of a single polar solvent. Yet, in additional embodiments, the polar solvent consists of a combination of two or more polar solvents.

In one or more embodiments, the hydrophobic carrier consists of a single polar solvent. Yet, in additional embodiments, the hydrophobic carrier consists of a combination of two or more hydrophobic carriers.

In order to derive a composition which is readily foamable upon release from a pressurized container, additional components are required, as provided hereinbelow.

Surface Active Agent

Surface-active agents (also termed "surfactants") include any agent linking oil and water in the composition, in the form of emulsion. A surfactant's hydrophilic/lipophilic balance (HLB) describes the emulsifier's affinity toward water or oil. The HLB scale ranges from 1 (totally lipophilic) to 20 (totally hydrophilic), with 10 representing an equal balance of both characteristics. Lipophilic emulsifiers form water-in-oil (w/o) emulsions; hydrophilic surfactants form oil-in-water (o/w) emulsions. The HLB of a blend of two emulsifiers equals the weight fraction of emulsifier A times its HLB value plus the weight fraction of emulsifier B times its HLB value (weighted average). The surface-active agent according to the present invention has an HLB value, suitable for stabilizing an emulsion comprising the aqueous phase and the organic carrier of the composition.

According to one or more embodiments of the present invention, the surface-active agent has a hydrophilic lipophilic balance (HLB) between about 9 and about 14, which is the required HLB (the HLB required to stabilize an O/W emulsion of a given oil) of most oils and hydrophobic solvents. Thus, in one or more embodiments, the composition contains a single surface active agent having an HLB value between about 9 and about 14 (e.g., about 9, about 10, about 11, about 12, about 13 and about 14), and in one or more embodiments, the composition contains more than one surface active agent and the weighted average of their HLB values is between about 9 and about 14 (e.g. about 9, about 10, about 11, about 12, about 13 and about 14). Yet, in other embodiments, when a water-in-oil emulsion is desirable, the composition contains one or more surface-active agents, having an HLB value between about 2 and about 9 (e.g., about 2, about 3, about 4, about 5, about 6, about 7, about 8 and about 9).

The surface-active agent is selected from anionic, cationic, nonionic, zwitterionic, amphoteric and ampholytic surfactants, as well as mixtures of these surfactants. Such surfactants are well known to those skilled in the therapeutic and cosmetic formulation art. Non-limiting examples of possible surfactants include polysorbates, such as polyoxyethylene (20) sorbitan monostearate (Tween 60) and poly (oxyethylene) (20) sorbitan monooleate (Tween 80); poly (oxyethylene) (POE) fatty acid esters, such as Myrj 45, Myrj 49, Myrj 52 and Myrj 59; poly(oxyethylene) alkylyl ethers, such as poly(oxyethylene) cetyl ether, poly(oxyethylene) palmityl ether, polyethylene oxide hexadecyl ether, polyethylene glycol cetyl ether, brij 38, brij 52, brij 56 and brij W1; sucrose esters, partial esters of sorbitol and its anhydrides, such as sorbitan monolaurate and sorbitan monolaurate; mono or diglycerides, isoceteth-20, sodium methyl cocoyl taurate, sodium methyl oleoyl taurate, sodium lauryl sulfate, triethanolamine lauryl sulfate and betaines.

In one or more embodiments of the present invention, the surface-active agent includes a non-ionic surfactant. Ionic surfactants are known to be irritants. Therefore, non-ionic surfactants are preferred in applications including sensitive tissue such as found in most mucosal tissues, especially when they are infected or inflamed. We have surprisingly found that non-ionic surfactants alone provide foams of excellent quality, i.e. a score of "E" according to the grading scale discussed herein below.

In one or more embodiments, the surface-active agent includes a mixture of a non-ionic surfactant and an ionic surfactant in a ratio in the range of about 100:1 to about 6:1. In one or more embodiments, the non-ionic to ionic surfactant ratio is greater than about 6:1, or greater than about 8:1; or greater than about 14:1, or greater than about 16:1, or greater than about 20:1.

In one or more embodiments of the present invention, a combination of a non-ionic surfactant and an ionic surfactant (such as sodium lauryl sulphate and cocamidopropylbetaine) is employed, at a ratio of between 1:1 and 20:1, for example, about 1:1, about 4:1, about 8:1, about 12:1, about 16:1 and about 20:1 or at a ratio of 4:1 to 10:1, for example, about 4:1, about 6:1, about 8:1 and about 10:1. The resultant foam has a low specific gravity, e.g., less than 0.1 g/ml.

Thus, in an exemplary embodiment, a combination of an non-ionic surfactant having HLB of less than about 9 and an non-ionic surfactant having HLB of equal or more than about 9 is employed, at a ratio of between about 1:8 and about 8:1, or at a ratio of about 4:1 to about 1:4, wherein the HLB of the combination of emulsifiers is between about 9 and about 14.

In one or more embodiments of the present invention, the surface-active agent includes mono-, di- and trimesters of sucrose with fatty acids (sucrose esters), prepared from sucrose and esters of fatty acids or by extraction from sucro-glycerides. Suitable sucrose esters include those having high monoester content, which have higher HLB values.

The total surface-active agent is in the range of about 0.1 to about 5% of the composition, and is occasionally less than about 2% or less than about 1%.

Polymeric Agent

In one or more embodiments, the foamable composition contains a polymeric agent. The polymeric agent serves to stabilize the foam composition and to control drug residence in the target organ. Exemplary polymeric agents are classified below in a non-limiting manner. In certain cases, a given polymer can belong to more than one of the classes provided below.

In one or more embodiments, the composition of the present invention includes a gelling agent. A gelling agent controls the residence of a therapeutic composition in the target site of treatment by increasing the viscosity of the composition, thereby limiting the rate of its clearance from the site. Many gelling agents are known in the art to possess mucoadhesive properties.

The gelling agent can be a natural gelling agent, a synthetic gelling agent and an inorganic gelling agent. Exemplary gelling agents that can be used in accordance with one or more embodiments of the present invention include, for example, naturally-occurring polymeric materials, such as locust bean gum, sodium alginate, sodium caseinate, egg albumin, gelatin agar, carrageenin gum, sodium alginate, xanthan gum, quince seed extract, tragacanth gum, guar gum, starch, chemically modified starches and the like, semi-synthetic polymeric materials such as cellulose ethers (e.g. hydroxyethyl cellulose, hydroxypropyl cellulose, methyl cellulose, carboxymethyl cellulose, methylhydroxyethylcellulose, methylhydroxypropylcellulose, hydroxypropylmethyl cellulose, hydroxyethylcarboxymethylcellulose, carboxymethylcellulose and carboxymethylhydroxyethylcellulose), guar gum, hydroxypropyl guar gum, soluble starch, cationic celluloses, cationic guars, and the like, and synthetic polymeric materials, such as carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers and the like. Mixtures of the above compounds are also contemplated.

Further exemplary gelling agents include the acrylic acid/ethyl acrylate copolymers and the carboxyvinyl polymers. Non-limiting examples include Carbopol® 934, Carbopol® 940, Carbopol® 950, Carbopol® 980, Carbopol® 951 and Carbopol® 981.

Yet, in other embodiments, the gelling agent includes inorganic gelling agents, such as silicone dioxide (fumed silica).

Mucoadhesive/bioadhesion has been defined as the attachment of synthetic or biological macromolecules to a biological tissue. Mucoadhesive agents are a class of polymeric biomaterials that exhibit the basic characteristic of a hydrogel, i.e. swell by absorbing water and interacting by means of adhesion with the mucous that covers epithelia. Compositions of the present invention may contain a mucoadhesive macromolecule or polymer in an amount sufficient to confer bioadhesive properties. The bioadhesive macromolecule enhances the delivery of biologically active agents on or through the target surface. The mucoadhesive macromolecule may be selected from acidic synthetic polymers, preferably having an acidic group per four repeating or monomeric subunit moieties, such as poly(acrylic)- and/or poly(methacrylic) acid (e.g., Carbopol®, Carbomer®), poly(methylvinyl ether/maleic anhydride) copolymer, and their mixtures and copolymers; acidic synthetically modified natural polymers, such as carboxymethylcellulose (CMC); neutral synthetically modified natural polymers, such as (hydroxypropyl)methylcellulose; basic amine-bearing polymers such as chitosan; acidic polymers obtainable from natural sources, such as alginic acid, hyaluronic acid, pectin, gum tragacanth, and karaya gum; and neutral synthetic polymers, such as polyvinyl alcohol or their mixtures. An additional group of mucoadhesive polymers includes natural and chemically modified cyclodextrin, especially hydroxypropyl-β-cyclodextrin. Such polymers may be present as free acids, bases, or salts, usually in a final concentration of about 0.01% to about 0.5% by weight. Many mucoadhesive agents are known in the art to also possess gelling properties.

In one or more embodiments, the polymeric agent contains a film-forming component. The film-forming component may include a water-insoluble alkyl cellulose or hydroxyalkyl cellulose. Exemplary alkyl cellulose or hydroxyalkyl cellulose polymers include ethyl cellulose, propyl cellulose, butyl cellulose, cellulose acetate, hydroxypropyl cellulose, hydroxybutyl cellulose, and ethylhydroxyethyl cellulose, alone or in combination. In addition, a plasticizer or a cross-linking agent may be used to modify the polymer's characteristics. For example, esters such as dibutyl or diethyl phthalate, amides such as diethyldiphenyl urea, vegetable oils, fatty acids and alcohols such as oleic and myristyl acid may be used in combination with the cellulose derivative.

In one or more embodiments, the polymeric agent includes a phase change polymer, which alters the composition behavior from fluid-like prior to administration to solid-like upon contact with the target mucosal surface. Such phase change results from external stimuli, such as changes in temperature or pH and exposure to specific ions (e.g., $Ca^{2+}$). Non-limiting examples of phase change polymers include poly(N-isopropylamide) and Poloxamer 407®.

The polymeric agent is present in an amount in the range of about 0.01% to about 5.0% by weight of the foam composition. In one or more embodiments, it is typically less than about 1 wt % of the foamable composition.

Preferably, a therapeutically effective foam adjuvant is included in the foamable compositions of the present invention to increase the foaming capacity of surfactants and/or to stabilize the foam. In one or more embodiments of the present invention, the foam adjuvant agent includes fatty alcohols having 15 or more carbons in their carbon chain, such as cetyl alcohol and stearyl alcohol (or mixtures thereof). Other examples of fatty alcohols are arachidyl alcohol (C20), behenyl alcohol (C22), 1-triacontanol (C30), as well as alcohols with longer carbon chains (up to C50). Fatty alcohols, derived from beeswax and including a mixture of alcohols, a majority of which has at least 20 carbon atoms in their carbon chain, are especially well suited as foam adjuvant agents. The amount of the fatty alcohol required to support the foam system is inversely related to the length of its carbon chains. Foam adjuvants, as defined herein are also useful in facilitating improved spreadability and absorption of the composition.

In one or more embodiments of the present invention, the foam adjuvant agent includes fatty acids having 16 or more carbons in their carbon chain, such as hexadecanoic acid (C16) stearic acid (C18), arachidic acid (C20), behenic acid (C22), octacosanoic acid (C28), as well as fatty acids with longer carbon chains (up to C50), or mixtures thereof. As for fatty alcohols, the amount of fatty acids required to support the foam system is inversely related to the length of its carbon chain.

In one or more embodiments, a combination of a fatty acid and a fatty ester is employed.

Optionally, the carbon atom chain of the fatty alcohol or the fatty acid may have a double bond. A further class of foam adjuvant agent includes a branched fatty alcohol or fatty acid. The carbon chain of the fatty acid or fatty alcohol also can be substituted with a hydroxyl group, such as 12-hydroxy stearic acid.

A property of the fatty alcohols and fatty acids used in context of the composition of the present invention is related to their therapeutic properties per se. Long chain saturated and mono unsaturated fatty alcohols, e.g., stearyl alcohol, erucyl alcohol, arachidyl alcohol and behenyl alcohol (docosanol) have been reported to possess antiviral, antiinfective, antiproliferative and antiinflammatory properties (see, U.S. Pat. No. 4,874,794). Longer chain fatty alcohols, e.g., tetracosanol, hexacosanol, heptacosanol, octacosanol, triacontanol, etc., are also known for their metabolism modifying properties and tissue energizing properties. Long chain fatty acids have also been reported to possess anti-infective characteristics.

In one or more embodiments, the active agent is encapsulated in particles, microparticles, nanoparticles, microcapsules, spheres, microspheres, nanocapsules, nanospheres, liposomes, niosomes, polymer matrix, nanocrystals or microsponges.

The composition of the present invention may further optionally include a variety of formulation excipients, which are added in order to fine-tune the consistency of the formulation, protect the formulation components from degradation and oxidation and modify their consistency. Such excipients may be selected, for example, from stabilizing agents, antioxidants, humectants, preservatives, colorant and odorant agents and other formulation components, used in the art of formulation.

Aerosol propellants are used to generate and administer the foamable composition as a foam. The total composition including propellant, foamable compositions and optional ingredients is referred to as the foamable carrier. The propellant makes up about 3% to about 25% (w/w) of the foamable carrier or composition. Examples of suitable propellants include volatile hydrocarbons such as butane, propane, isobutane or mixtures thereof, and fluorocarbon gases.

Non-Flammable Stable Foam Compositions

Alcohol and organic solvents render foams inflammable. It has been surprisingly discovered that fluorohydrocarbon propellants, other than chloro-fluoro carbons (CMCs), which are non-ozone-depleting propellants, are particularly useful in the production of a non-flammable foamable composition. A test according to European Standard prEN 14851, titled "Aerosol containers-Aerosol foam flammability test" revealed that compositions containing an organic carrier that contains a hydrophobic organic carrier and/or a polar solvent, which are detected as inflammable when a hydrocarbon propellant is used, become non-flammable, while the propellant is an HFC propellant.

Such propellants include, but are not limited to, hydrofluorocarbon (HFC) propellants, which contain no chlorine atoms, and as such, fall completely outside concerns about stratospheric ozone destruction by chlorofluorocarbons or other chlorinated hydrocarbons. Exemplary non-flammable propellants according to this aspect of the invention include propellants made by DuPont under the registered trademark Dymel, such as 1,1,1,2 tetrafluoroethane (Dymel 134), and 1,1,1,2,3,3,3 heptafluoropropane (Dymel 227). HFCs possess Ozone Depletion Potential of 0.00 and thus, they are allowed for use as propellant in aerosol products.

Notably, the stability of foamable emulsions including HFC as the propellant is improved in comparison with the same composition made with a hydrocarbon propellant.

Active Agents

It is to be understood that the active agents useful herein can in some instances provide more than one benefit or operate via more than one mode of action. Therefore, classifications herein are made for the sake of convenience and are not intended to limit the active agent to that particular application or applications listed.

The composition of the present invention comprises an active agent that provides therapeutic or cosmetic activity.

Non-limiting examples of active agents include an anti-infective, an antibiotic, an antibacterial agent, an antifungal agent, an antiviral agent, an antiparasitic agent, a steroidal anti-inflammatory agent, a nonsteroidal anti-inflammatory agent, an immunosuppressive agent, an immunomodulator, an immunoregulating agent, a hormonal agent, a steroid, a vasoactive agent, a vasoconstrictor, a vasodilator, vitamin A, a vitamin A derivative, a retinoid, vitamin B, a vitamin B derivative, vitamin C, a vitamin C derivative, vitamin D, a vitamin D derivative, vitamin E, a vitamin E derivative, vitamin F, a vitamin F derivative, vitamin K, a vitamin K derivative, a wound healing agent, a burn healing agent, a disinfectant, an anesthetic, an antiallergic agent, an alpha hydroxyl acid, lactic acid, glycolic acid, a beta-hydroxy acid, a protein, a peptide, a neuropeptide, an allergen, an immunogenic substance, a haptene, an oxidizing agent, an antioxidant, a dicarboxylic acid, azelaic acid, sebacic acid, adipic acid, fumaric acid, an insecticide, an antiproliferative agent, an anticancer agent, a photodynamic therapy agent, an anti-wrinkle agent, a radical scavenger, a metal oxide (e.g., titanium dioxide, zinc oxide, zirconium oxide, iron oxide), silicone oxide, talc, an anti-acne agent, a skin whitening agent, a self tanning agent, an anti-cellulite agent, a skin protective agent, a masking agent, an anti-wart agent, a refatting agent, a lubricating agent and mixtures thereof at any proportion. The concentration of the active agent can be adapted to exert a therapeutic effect on a disease when applied to an afflicted area. Various different therapeutic effects of the herbs and their extracts are, for example, illustrated in the above-mentioned references.

In one or more embodiments the active agent may be an extract or tincture of one or more beneficial agents that have beneficial properties, for example, when applied to the skin, a body surface, a body cavity or a mucosal surface. The extract can be, for example, alcoholic, hydroalcoholic, propylene glycol, glycerine, dry, press, cold, hot, liquid carbon dioxide, oil or other process known in the art. The extract or tincture may comprise of substances of animal, plant, (such as herb, fruit, vegetable) mineral or other origin. Nonlimiting examples are proteins, polypeptides, sugars, hyularonic acid, and coal tar. Herbal extracts may be from any known therapeutic herb, as listed for example in Herbal Medicines, London: Pharmaceutical Press Electronic Version 2006 or in the American Herbal Association electronic publication Herbal gram or in German Commission E., such as, angelica, calendula, celery, coltsfoot, comfrey, dandelion, jamaica dogwood, kava, marshmallow, prickly ash, northern prickly ash, southern senna, valerian, agrimony, aloe vera, alfalfa, artichoke, avens, bayberry, bloodroot, blue flag, bogbean, boldo, boneset, broom, buchu, burdock, burnet, calamus, calendula, cascara, centaury, cereus, chamomile, german chamomile, roman chamomile, cinnamon, clivers, cohosh, black, cohosh, blue, cola, corn silk, couchgrass, cowslip, damiana, devil's claw, drosera, echinacea, elder, elecampane, euphorbia, eyebright, figwort, frangula, fucus, fumitory, garlic, golden seal, gravel root, ground ivy, guaiacum, hawthorn, holy thistle, hops, horehound black, horehound white, horse chestnut hydrangea, ispaghula, juniper, lady's lipper, liferoot, lime flower, liquorice, lobelia, maté, meadowsweet, mistletoe, motherwort, myrrh, nettle, parsley, parsley piert, passionflower, pennyroyal, pilewort, plantain, pleurisy root, pokeroot, poplar, pulsatilla, queen's delight, raspberry, red clover, rosemary, sage, sarsaparilla, sassafras, scullcap, senega, shepherd's purse, skunk cabbage, slippery elm, squill, St. john's wort, stone root, tansy, thyme, uva-ursi, vervain, wild carrot, wild lettuce, willow, witch hazel, yarrow and yellow dock.

When the extract is dissolved in a polar solvent, such as a short chain alcohol (e.g., ethanol and isopropyl alcohol), propylene glycol and glycerin, then the polar solvent of the extract can also comprise part or all of the "polar solvent" component of the foamable composition, as specified throughout this specification and likewise the polar solvent of the foamable composition can also comprise as part or all of the "polar solvent" component of the extract.

In one or more embodiments, the active agent is an anti-infective agent, selected from an antibiotic agent, an antibacterial agent, an anti-fungal agent, an anti-viral agent and an anti-parasite agent.

The antibacterial drug can be active against gram positive and gram-negative bacteria, protozoa, aerobic bacteria and unaerobic ones.

In one or more embodiments, the antibiotic agent is selected from the classes consisting of beta-lactam antibiotics, synthetic and semi-synthetic penicillins, aminoglycosides, ansa-type antibiotics, anthraquinones, antibiotic azoles, antibiotic glycopeptides, macrolides, antibiotic nucleosides, antibiotic peptides, antibiotic polyenes, antibiotic polyethers, quinolones, fluoroquinolones, antibiotic steroids, cyclosporines, sulfonamides, tetracycline, chloramphenicol, dicarboxylic acids, such as azelaic acid, salicylates, antibiotic metals, oxidizing agents, substances that release free radicals and/or active oxygen, cationic antimicrobial agents, quaternary ammonium compounds, biguanides, triguanides, bisbiguanides and analogs and polymers thereof and naturally occurring antibiotic compounds.

Additional antibacterial agents, which are non-specific, include strong oxidants and free radical liberating compounds, such as hydrogen peroxide, bleaching agents (e.g., sodium, calcium or magnesium hydochloride and the like), iodine, chlorohexidine and benzoyl peroxide.

The antifungal agent can be an azole compound. Exemplary azole compounds include azoles selected from the group consisting of azoles, diazoles, triazoles, miconazole, ketoconazole, clotrimazole, econazole, mebendazole, bifonazole, butoconazole, fenticonazole, isoconazole, oxiconazole, sertaconazole, sulconazole, thiabendazole, tiaconazole, fluconazole, itraconazole, ravuconazole and posaconazole.

Additional exemplary antifungal agents include griseofulvin, ciclopirox, amorolfine, terbinafine, Amphotericin B, potassium iodide, flucytosine (5FC) and any combination thereof at a therapeutically effective concentration.

In one or more embodiments, the active agent is an anti-viral agent. Any known antiviral agent, in a therapeutically effective concentration, can be incorporated in the foam composition of the present invention. Exemplary antiviral agents include, but not limited to, acyclovir, famciclovir, gancyclovir, valganciclovir and abacavir.

In another embodiment according to the present invention, the active agent is an anti-inflammatory or anti-allergic agent. Anti-inflammatory agents can be selected from the group of corticosteroids, non-steroidal anti-inflammatory drugs (NSAIDs), anti-histamines, immunosuppressant agents, immunomodulators; and any combination thereof at a therapeutically effective concentration.

Non-limiting examples of corticosteroids include hydrocortisone, hydrocortisone acetate, desonide, betamethasone valerate, clobetasone-17-butyrate, fluocinonide, fluocinolone acetonide, alcometasone dipropionate, mometasone furoate, prednicarbate, triamcinolone acetonide, betamethasone-17-benzoate, methylprednisolone aceponate, betamethasone dipropionate, halcinonide, triamcinolone acetonide, halobetasol and clobetasol-17-propionate.

A second class of anti-inflammatory agents, which is useful in the foam of the present invention, includes the nonsteroidal anti-inflammatory agents (NSAIDs). The variety of compounds encompassed by this group is well known to those skilled in the art. Specific non-steroidal anti-inflammatory agents useful in the composition invention include, but are not limited to, oxicams, such as piroxicam, isoxicam, tenoxicam, sudoxicam; salicylates, such as salicylic acid, ethyl salicylate, methyl salicylate, aspirin, disalcid, benorylate, trilisate, safapryn, solprin, diflunisal, and fendosal; scetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and pyrazoles, such as phenylbutazone, oxyphenbutazone, feprazone, azapropazone, and trimethazone.

Any further steroidal and nonsteroidal compounds, having the capacity to prevent, alleviate the symptoms of, treat or cure inflammation processes, are generally included, as possible anti-inflammatory agents, according to the present invention.

Antiallergic active agents include antihistamine compounds, including, in a non limiting manner, thylenediamines, such as pyrilamine (mepyramine), antazoline and methapyrilene; tripelennamine phenothiazines, such as promethazine, methdilazine and trimeprazine; ethanolamines, such as diphenhydramine, bromodiphenhydramine, carbinoxamine, clemastine, dimenhydrinate, diphenylpyraline, doxylamine and phenyltoxamine; piperazines, such as cyclizine, buclizine, chlorcyclizine, hydroxyzine, meclizine and thiethylperazine; alkylamines, such as brompheniramine, pyrrobutamin, desbrompheniramine, tripolidine, dexchlorpherniramine, chlorpheniramine; dimethindene and pheniramine; and piperidines, such as cyproheptadine and azatadine. These active agents, as well as additional antihistamines can also be incorporated in the composition of the present invention.

The composition of the present invention may also comprise an anti-inflammatory or antiallergic agent, wherein said agent reduces the occurrence of pro-inflammatory cytokines or inhibits the effect of pro-inflammatory cytokines.

Immunosuppressant agents, immunoregulating agents and immunomodulators are chemically or biologically derived agents that modify the immune response or the functioning of the immune system (as by the stimulation of antibody formation or the inhibition of white blood cell activity). Immunosuppressant agents and immunomodulators include, among other options, cyclic peptides, such as cyclosporine, tacrolimus, tresperimus, pimecrolimus, sirolimus (rapamycin), verolimus, laflunimus, laquinimod and imiquimod.

In one or more embodiments, the active agent is a topical anesthetic. Examples of topical anesthetic drugs include, but not limited to, benzocaine, lidocaine, bupivacaine, chlorprocaine, dibucaine, etidocaine, mepivacaine, tetracaine, dyclonine, hexylcaine, procaine, cocaine, ketamine, pramoxine, and phenol. Mixtures of such anesthetic agents may be synergistically beneficial.

In one or more embodiments, the active agent is a "keratolytically active agent." The term "keratolytically active agent" refers herein to a compound which loosens and removes the stratum corneum of the skin, or alters the structure of the keratin layers of the skin.

Suitable keratolytically active agents include phenol and substituted phenolic compounds. Such compounds are known to dissolve and loosen the intracellular matrix of the hyperkeratinized tissue. Dihydroxy benzene and derivatives thereof have been recognized as potent keratolytic agents. Resorcinol (m-dihydroxybenzene) and derivatives thereof are used in anti-acne preparations. Hydroquinone (p-dihydroxybenzene), besides its anti-pigmentation properties, is also keratolytic.

Vitamin A and its derivatives, such as retinoic acid, isoretinoic acid, retinol and retinal are another preferred class of keratolytically active agents.

Another group of keratolytically active agents include alpha-hydroxy acids, such as lactic acid and glycolic acid and their respective salts and derivatives; and beta-hydroxy acids, such as Salicylic acid (o-hydroxybenzoic acid) and its salts and pharmaceutically acceptable derivatives, which typically possess anti-inflammatory, as well as keratolytic, activity. Yet, another class of preferred keratolytically active agents includes urea and its derivatives.

In one or more embodiments, the active agent is a retinoid. Retinoids include, for example, retinol, retinal, all-trans retinoic acid and derivatives, isomers and analogs thereof. Etretinate, actiretin, isotretinoin, adapalene and tazarotene are further examples of said retinoid isomers and analogs.

In one or more embodiments, the active agent is an insecticide or an insect repellent agent.

In one or more embodiments, the active agent is an anti cancer agent.

In one or more embodiments, the active agent is a photodynamic therapy (PDT) agent. By way of example, such PDT agents can be modified porphyrins, chlorins, bacteriochlorins, phthalocyanines, naphthalocyanines, pheophorbides, purpurins, m-THPC, mono-L-aspartyl chlorin e6, bacteriochlorins, phthalocyanines, benzoporphyrin derivatives, as well as photosensitizer precursors, such as aminolevulinic acid (ALA).

In one or more embodiments, the active agent is an agent useful in the treatment of burns, wounds, cuts and ulcers. The foam compositions of the present invention may comprise a combination of anti-infective agents (against bacteria, fungi and/or viruses), anti-inflammatory agents (steroidal and/or NSAIDs) and pain relieving components.

The foam compositions of the present invention, with or without further active ingredients, are suitable for the further application as "cosmeceutical" preparation (cosmetic products with therapeutic benefit), to treat "cosmetic" skin disorders, such as aging skin, wrinkles, hyperpigmentation (melasma, chloasma, freckles, etc.), scaly skin and other skin undesirable properties.

Any cosmetically active agent is considered an active agent in the context of the present invention. The CTFA Cosmetic Ingredient Handbook describes a wide variety of non-limiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, astringents, etc. (e.g., clove oil, menthol, camphor, eucalyptus oil, eugenol, menthyl lactate, witch hazel distillate), anti-acne agents, anti-caking agents, antifoaming agents, anti-microbial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, and vitamins and derivatives thereof.

In one or more embodiments, the active agent is an agent useful in the treatment of acne, wrinkles and scars. Examples of useful anti-acne actives include resorcinol, sulfur, salicylic acid and salicylates, alpha-hydroxy acids, nonsteroidal anti-inflammatory agents, benzoyl peroxide, retinoic acid, isoretinoic acid and other retinoid compounds, adapalene, tazarotene, azelaic acid and azelaic acid derivatives, antibiotic agents, such as erythromycin and clyndamycin, zinc salts and complexes, and combinations thereof, in a therapeutically effective concentration. Exemplary anti-wrinkle/anti-atrophy active agents suitable for use in the compositions of the present invention include sulfur-containing D and L amino acids and their derivatives and salts, particularly the N-acetyl derivatives; thiols; hydroxy acids (e.g., alpha-hydroxy acids such as lactic acid and glycolic acid and their derivatives and salts; or beta-hydroxy acids such as salicylic acid and salicylic acid salts and derivatives), urea, hyaluronic acid, phytic acid, lipoic acid; lysophosphatidic acid, skin peel agents (e.g., phenol, resorcinol and the like), vitamin B3 compounds (e.g., niacinamide, nicotinic acid and nicotinic acid salts and esters, including non-vasodilating esters of nicotinic acid (such as tocopheryl nicotinate), nicotinyl amino acids, nicotinyl alcohol esters of carboxylic acids, nicotinic acid N-oxide and niacinamide N-oxide), vitamin B5 and retinoids (e.g., retinol, retinal, retinoic acid, retinyl acetate, retinyl palmitate, retinyl ascorbate). In the case of dry, scaly skin (xerosis) and ichthyosis such agents can alleviate the symptoms by temporary relief of itching associated with these conditions.

In one or more embodiments, the active agent is an anti-oxidant or a radical scavenger. Anti-oxidants/radical scavengers such as ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5, 7,8-tetramethylchroman-2-carboxylic acid, gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts may be used.

It is further pointed out that polyunsaturated fatty acids, containing omega-3 and omega-6 fatty acids (e.g., linoleic and linolenic acid, gamma-linoleic acid (GLA), eicosapentaenoic acid (EPA) and docosahexaenoic acid (DHA)) are beneficial in the treatment of psoriasis and other skin inflammation conditions. Likewise, emollients and silicone oils exert moisture-retaining and skin protective effects on the skin. Thus, in a preferred embodiment, a skin protective foam is provided, wherein the hydrophobic carrier comprises in full or in part, an organic liquid selected from the group consisting of emollients, silicone oil and oils rich in unsaturated fatty acids.

In one or more embodiments, the active agent is a self-tanning active Agent, such as dihydroxyacetone.

According to another embodiment, the active agent comprises solid matter or particulate matter, i.e., material that is not soluble in the liquid carrier composition of the foamable composition. For definition purposes, solid matter shall mean material that is not soluble in the foamable composition more than 10% of the concentration intended to be included in said foamable composition. By way of example, the following classes of solid matter substances are presented: metallic oxides, such as titanium dioxide, zinc oxide, zirconium oxide, iron oxide; silicon containing materials such as silicone oxide and talc; carbon, for example in the form of amorphous carbon or graphite; insoluble oxidizing agents, such as benzoyl peroxide, calcium and magnesium hypochlorite; metallic Silver; cosmetic scrub materials, including, for example meals of strawberry seeds, raspberry seeds, apricot seeds, sweet almond, cranberry seeds; and pigments.

According to certain embodiments, the active agent is selected from the group of solvent, surface active agent, foam adjuvant and gelling agent, which are, on a case-by-case basis, known to possess a therapeutic benefit.

In one or more embodiments at least one or at least two active agents are included in the composition.

Composition and Foam Physical Characteristics and Advantages

A pharmaceutical or cosmetic composition manufactured using the foamable carrier of the present invention is very easy to use. When applied onto the afflicted body surface of mammals, i.e., humans or animals, it is in a foam state, allowing free application without spillage. Upon further application of a mechanical force, e.g., by rubbing the composition onto the body surface, it freely spreads on the surface and is rapidly absorbed.

The foamable composition can be in the state of (1) solutions; (2) a readily dispersable suspension; or (3) an emulsion. It is stable, having an acceptable shelf life of a year, or at least two years at ambient temperature, as revealed in accelerated stability tests. Polar solvents, hydrophobic carriers and propellants, which are a mixture of low molecular weight hydrocarbons, tend to impair the stability of emulsions and to interfere with the formation of a stable foam upon release from a pressurized container. It has been observed, however, that the foamable compositions according to the present invention are surprisingly stable. Following accelerated stability studies, they demonstrate desirable texture; they form fine bubble structures that do not break immediately upon contact with a surface, spread easily on the treated area and absorb quickly.

The composition should also be free flowing, to allow it to flow through the aperture of the container, e.g., and aerosol container, and create an acceptable foam. Compositions containing semi-solid hydrophobic solvents, e.g., white petrolatum, as the main ingredients of the oil phase of the emulsion, exhibit high viscosity and poor flowability and are inappropriate candidates for a foamable composition.

Foam quality can be graded as follows:

Grade E (excellent): very rich and creamy in appearance, does not show any bubble structure or shows a very fine (small) bubble structure; does not rapidly become dull; upon spreading on the skin, the foam retains the creaminess property and does not appear watery.

Grade G (good): rich and creamy in appearance, very small bubble size, "dulls" more rapidly than an excellent foam, retains creaminess upon spreading on the skin, and does not become watery.

Grade FG (fairly good): a moderate amount of creaminess noticeable, bubble structure is noticeable; upon spreading on the skin the product dulls rapidly and becomes somewhat lower in apparent viscosity.

Grade F (fair): very little creaminess noticeable, larger bubble structure than a "fairly good" foam, upon spreading on the skin it becomes thin in appearance and watery.

Grade P (poor): no creaminess noticeable, large bubble structure, and when spread on the skin it becomes very thin and watery in appearance.

Grade VP (very poor): dry foam, large very dull bubbles, difficult to spread on the skin.

Topically administrable foams are typically of quality grade E or G, when released from the aerosol container. Smaller bubbles are indicative of more stable foam, which does not collapse spontaneously immediately upon discharge from the container. The finer foam structure looks and feels smoother, thus increasing its usability and appeal.

As a further aspect of the foam is breakability. The breakable foam is thermally stable, yet breaks under sheer force. Sheer-force breakability of the foam is clearly advantageous over thermally induced breakability. Thermally sensitive foams immediately collapse upon exposure to skin temperature and, therefore, cannot be applied on the hand and afterwards delivered to the afflicted area.

The foam of the present invention has several advantages, when compared with hydroalcoholic foam compositions, such as described in U.S. Pat. Nos. 6,126,920 and 5,783,202:

(1) Breakability. The foam of the present invention is thermally stable. Unlike hydroalcoholic foam compositions of the prior art, the foam of the present invention is not "quick breaking", i.e., it does not readily collapse upon exposure to body temperature environment. Sheer-force breakability of the foam is clearly advantageous over thermally induced breakability, since it allows comfortable application and well directed administration to the target area.

(2) Skin drying and skin barrier function. Polar solvents known to dry the skin and impair the integrity of the skin barrier. By contrast, combining a polar solvent and a hydrophobic carrier, as described herein, unwanted skin barrier damage is reduced, as demonstrated in tran-epidermal water loss measurements.

(3) Irritability. Due to the improvement in skin barrier function, skin irritability is corrected.

In terms of usability, the foamable composition is most advantageous, as revealed by clinical trials:

(i) Ease of Application.

When foam is released it expands and allows easy spreading on the target area. This advantage is particularly meaningful in regards to the treatment of large skin surfaces.

Upon application, the foam readily spreads and absorbs into the skin.

(ii) The Foam is Drip-Free

The foam is not liquid and therefore does not leak when applied.

This allows precise application, without the product being spread on clothes or other parts of the body.

Another property of the foam is specific gravity, as measured upon release from the aerosol can. Typically, foams have specific gravity of less than 0.12 g/mL; or less than 0.12 g/mL; or less than 0.08 g/mL, depending on their composition and on the propellant concentration.

For the purpose of the specification the external limits of the various ranges given are approximate as will be appreciated by those skilled in the art. Therefore, for the purpose of interpreting the outer limits of the range the limits shall be deemed to include up to a 20% leeway outside the range, preferably a 10% leeway.

Fields of Applications

According to one or more embodiments of the present invention, the foamable carrier and the foamable pharmaceutical or cosmetic composition of the present invention are intended for administration to an animal or a human subject. In one or more embodiments, the composition is intended to treat the skin, a body surface, a body cavity or a mucosal surface, e.g., the mucosa of the nose, mouth, eye, ear, respiratory system, vagina or rectum.

By including an appropriate active agent in the compositions of the present invention, the composition are useful in treating a patient having any one of a variety of dermatological disorders, which include inflammation as one or their etiological factors (also termed "dermatoses"), such as classified in a non-limiting exemplary manner according to the following groups:

Dermatitis including contact dermatitis, atopic dermatitis, seborrheic dermatitis, nummular dermatitis, chronic dermatitis of the hands and feet, generalized exfoliative dermatitis, stasis dermatitis; lichen simplex chronicus; diaper rash;

Bacterial infections including cellulitis, acute lymphangitis, lymphadenitis, erysipelas, cutaneous abscesses, necrotizing subcutaneous infections, staphylococcal scalded skin syndrome, folliculitis, furuncles, hidradenitis suppurativa, carbuncles, paronychial infections, and erythrasma;

Fungal Infections including dermatophyte infections, yeast Infections; parasitic Infections including scabies, pediculosis, creeping eruption;

Viral Infections;

Disorders of hair follicles and sebaceous glands including acne, rosacea, perioral dermatitis, hypertrichosis (hirsutism), alopecia, including male pattern baldness, alopecia areata, alopecia universalis and alopecia totalis; pseudofolliculitis barbae, keratinous cyst;

Scaling papular diseases including psoriasis, pityriasis rosea, lichen planus, pityriasis rubra pilaris;

Benign tumors including moles, dysplastic nevi, skin tags, lipomas, angiomas, pyogenic granuloma, seborrheic keratoses, dermatofibroma, keratoacanthoma, keloid;

Malignant tumors including basal cell carcinoma, squamous cell carcinoma, malignant melanoma, paget's disease of the nipples, kaposi's sarcoma;

Reactions to sunlight, including sunburn, chronic effects of sunlight, photosensitivity;

Bullous diseases including pemphigus, bullous pemphigoid, dermatitis herpetiformis, linear immunoglobulin A disease;

Pigmentation disorders including hypopigmentation such as vitiligo, albinism and postinflammatory hypopigmentation and hyperpigmentation such as melasma (chloasma), drug-induced hyperpigmentation, postinflammatory hyperpigmentation;

Disorders of cornification including ichthyosis, keratosis pilaris, calluses and corns, actinic keratosis;

Pressure sores, open wounds, chronic wounds, open ulcers and burns;

Disorders of sweating; and

Inflammatory reactions including drug eruptions, toxic epidermal necrolysis, erythema multiforme, erythema nodosum, and granuloma annulare.

The same advantage is expected when the composition is topically applied to a body cavity or mucosal surfaces, including, but not limited to the cranial cavity, the thoratic cavity, the abdominal cavity, the venteral cavity, the vagina, the rectum and penile cavities, the urinary tract, the nasal cavity, the mouth, the eye, the ear the peritoneum, the large and small bowel, the caecum, bladder, and stomach, the cavity between the uterus and the fallopian tubes, the ovaries and other body areas, which may accept topically-applied products. The composition of the present invention is suitable to treat conditions of a body cavity and a mucosal membrane, such as post-surgical adhesions, chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum.

According to one or more embodiments of the present invention, the compositions are also useful in the therapy of non-dermatological disorders by providing transdermal or trans-mucosal delivery of an active agent that is effective against non-dermatological disorders.

In one or more embodiments, the disorder is a health abnormality that responds to treatment with a hormone. A typical example of such abnormality is sexual dysfunction in men and women whereby androgen therapy is successfully used to restore sexual function. Other non-limiting examples of disorders/medical indications that are in the scope of treatment with a hormone according to the present invention are androgen deficiency, estrogen deficiency, growth disorders, hypogonadism, cancer, vasomotor symptoms, menopausal disorders, vulvar and vaginal atrophy, urethritis, hypoestrogenism, osteoarthritis, osteoporosis, uterine bleeding, Hirsutism, Virilization, ovarian tumors, hypothalamic pituitary unit diseases, testicular tumors, prostate cancer, hypopituitarism, Klinefelter's syndrome, testicular feminisation, orchitectomy, vasomotor symptoms (such as "hot flashes") associated with the menopause, metabolic abnormalities and mood disturbances.

The following examples further exemplify the, foamable carrier, the pharmaceutical and cosmetic compositions of the present invention, methods for preparing the same, and therapeutic uses of the compositions. The examples are for the purposes of illustration only and are not intended to be limiting of the invention. Many variations may be carried out by one of ordinary skill in the art and are contemplated within the full scope of the present invention.

A general procedure for preparing foamable compositions is set out in WO 2004/037225 which is incorporated herein by reference. Moreover, with respect to using one or more polar solvents, the polor solvent is added to the aqueous phase mixture in the course of preparation.

Example 1—Foamable Carrier, Containing Polar Solvent (Dimethyl Isosorbide) and Hydrophobic Carrier (Caprylic/Capric Triglyceride)

|  | Foam A % w/w | Foam B % w/w | Foam C % w/w |
|---|---|---|---|
| Caprylic/capric triglyceride (Hydrophobic carrier) | 30.0 | 19.0 | 40.0 |
| Dimethyl isosorbide (Polar solvent) | 20.0 | 20.0 | 20.0 |
| Glyceryl oleate (Surfactant) | 1.0 | 2.0 | 1.0 |
| PPG-15 stearyl ether (Surfactant) | 5.0 | 15.0 | 5.0 |
| Lecithin (Surfactant) | 20.0 | 20.0 | 10.0 |
| Sorbitan stearate (Surfactant) | — | — | 5.0 |
| Sucrose stearate (Surfactant) | 5.0 | 5.0 | — |
| PVP K-90 (Polymeric agent) | 0.5 | 0.5 | 0.5 |
| Preservative | 0.5 | 0.5 | 0.5 |
| Propane/ButaneX agent) | 8.00 | 8.00 | 8.00 |
| Purified water | to 100.00 | to 100.00 | to 100.00 |
| Foam properties | | | |
| Foam quality | Excellent | Excellent | Excellent |
| Density | 0.06 | 0.08 | 0.06 |
| Formulation type | Dispersion | | |
| Homogeneity | Homogenious upon mild shaking | Homogenious upon mild shaking | Homogenious upon mild shaking |

Example 2—Foamable Carrier, Containing Polar Solvent (Dimethyl Isosorbide and Propylene Glycol) and Hydrophobic Carrier (Caprylic/Capric Triglyceride and Isopropyl Myristate)

|  | Foam D % w/w | Foam E % w/w | Foam F % w/w |
|---|---|---|---|
| Caprylic/capric triglyceride (Hydrophobic carrier) | 5.00 | 5.00 | 5.00 |
| Isopropyl myristate (Hydrophobic carrier) | 5.00 | 5.00 | 5.00 |
| Dimethyl isosorbide (Polar solvent) | 55.50 | 62.00 | 59.00 |
| Propylene glycol (Polar solvent) | 2.50 | — | — |
| Glyceryl monostearate (Surfactant) | — | 1.00 | 1.00 |
| Sorbitan monostearate (Surfactant) | 8.00 | 5.00 | 8.00 |
| Sucrose stearate (Surfactant) | 5.00 | 5.00 | 8.00 |
| Hydroxypropylcellulose (Polymeric agent) | — | 0.50 | — |
| Cetostearyl alcohol (Foam adjuvant) | 8.00 | 8.00 | — |
| Stearyl alcohol (Foam adjuvant) | — | — | 5.00 |
| Oleyl alcohol (Foam adjuvant) | 2.50 | — | — |
| Preservative | 0.5 | 0.5 | 0.5 |
| Propane/Butane (Propellant) | 8.00 | 8.00 | 8.00 |
| Purified water | to 100.00 | to 100.00 | to 100.00 |
| Foam properties | | | |
| Foam quality | Excellent | Excellent | Good |
| Density | 0.13 | 0.23 | 0.21 |
| Formulation type | Solution | Solution | Solution |
| Homogeneity | Homogeneous upon mild shaking | Homogeneous upon mild shaking | Homogeneous upon mild shaking |

Example 3—Foamable Carrier, in the Form of Emulsion, Containing Polar Solvent (Diethyl Isosorbide) and Hydrophobic Carrier (Caprylic/Capric Triglyceride)

| | Foam G % w/w |
|---|---|
| Caprylic/capric triglyceride (Hydrophobic carrier) | 30.00 |
| Dimethyl isosorbide (Polar solvent) | 20.00 |
| Glyceryl monostearate (Surfactant) | 2.00 |
| PPG-15 stearyl ether | 3.00 |
| Sorbitan stearate (Surfactant) | 2.00 |
| Xanthan gum (Polymeric agent) | 0.15 |
| Hydroxypropyl methylcellulose (Polymeric agent) | 0.15 |
| Stearyl alcohol (Foam adjuvant) | 1.00 |
| Preservative | 0.5 |
| Propane/Butane (Propellant) | 8.00 |
| Purified water | to 100.00 |
| Foam properties | |
| Foam quality | Excellent |
| Density | 0.12 |
| Formulation type | Emulsion |
| Emulsion stability (centrifuge) | Stable |

Example 4—Foamable Carrier, in the Form of Emulsion, Containing Polar Solvent (Ethanol) and Hydrophobic Carrier (Caprylic/Capric Triglyceride)

| | Foam H % w/w | Foam I % w/w |
|---|---|---|
| Mineral oil (Hydrophobic carrier) | 4.62 | 4.32 |
| Isopropyl myristate (Hydrophobic carrier) | 4.62 | 4.32 |
| Ethanol (Polar solvent) | 15.00 | 20.00 |
| Glyceryl monostearate (Surfactant) | 0.39 | 0.36 |
| Polysorbate 80 (Surfactant) | 0.77 | 0.72 |
| PEG-40 stearate (Surfactant) | 2.31 | 2.16 |
| Xanthan gum (Polymeric agent) | 0.23 | 0.22 |
| Hydroxypropyl methylcellulose (Polymeric agent) | 0.23 | 0.22 |
| Stearyl alcohol (Foam adjuvant) | 0.77 | 0.72 |
| Preservative | 0.50 | 0.50 |
| Propane/Butane (Propellant) | 8.00 | 8.00 |
| Purified water | to 100.00 | to 100.00 |
| Foam properties | | |
| Foam quality | Excellent | Excellent |
| Density | 0.04 | 0.04 |
| Formulation type | Emulsion | Emulsion |
| Emulsion stability (centrifuge) | Stable | Stable |

Example 5—Non-Flammable Foamable Carriers

| | Foam J % w/w |
|---|---|
| Caprylic/capric triglyceride (Hydrophobic carrier) | 5.00 |
| Isopropyl myristate (Hydrophobic carrier) | 5.00 |
| Dimethyl isosorbide (Polar solvent) | 59.00 |
| Propylene glycol (Polar solvent) | — |
| Glyceryl monostearate (Surfactant) | 1.00 |
| Sorbitan monostearate (Surfactant) | 8.00 |
| Sucrose stearate (Surfactant) | 8.00 |
| Hydroxypropylcellulose (Polymeric agent) | — |
| Cetostearyl alcohol (Foam adjuvant) | — |
| Stearyl alcohol (Foam adjuvant) | 5.00 |
| Oleyl alcohol (Foam adjuvant) | — |

-continued

| | Foam J % w/w |
|---|---|
| Preservative | 0.5 |
| 1,1,1,2 tetrafluorethane (Dymel 134) | 8.00 |
| Purified water | to 100.00 |

| | Foam K % w/w |
|---|---|
| Mineral oil (Hydrophobic carrier) | 4.32 |
| Isopropyl myristate (Hydrophobic carrier) | 4.32 |
| Ethanol (Polar solvent) | 20.00 |
| Glyceryl monostearate (Surfactant) | 0.36 |
| Polysorbate 80 (Surfactant) | 0.72 |
| PEG-40 stearate (Surfactant) | 2.16 |
| Xanthan gum (Polymeric agent) | 0.22 |
| Hydroxypropyl methylcellulose (Polymeric agent) | 0.22 |
| Stearyl alcohol (Foam adjuvant) | 0.72 |
| Preservative | 0.50 |
| 1,1,1,2 tetrafluorethane (Dymel 134) | 8.00 |
| Purified water | to 100.00 |

Example 6—Inflammability Test

The following compositions were tested for inflammability according to European Standard prEN 14851: (1) Foam F; (2) Foam I; (3) Foam J; and (4) Foam K.

Procedure: Approximately 5 g of foam, mousse gel or paste is sprayed from the aerosol container on to a watchglass. An ignition source (a lighter) was placed at the base of the watchglass and any ignition and sustained combustion of the foam, mousse, gel or paste was observed. The test was carried out in a draught-free environment capable of ventilation, with the temperature controlled at 20° C.±5° C. and relative humidity in the range of 30% to 80%. According to the standard, appearance of a stable flame which is at least 4 cm high and which is maintained for at least 2 seconds defines a product as "inflammable".

Results:

Foam F and Foam I were found "inflammable".

Foam J and Foam K were found "non-flammable".

Example 7

Exemplary concentrations of active agents in foamable compositions are set out in Table 2. Each active agent is added into, for example, any of the carriers listed in any of Examples 1 to 5 above in a therapeutically effective concentration and amount. The methodology of addition is well known to those of the art. The composition is adjusted in each case so that it is made up to 100% w/w appropriate by purified water.

TABLE 2

Exemplary Concentrations of Examples of Active Agents

| Class | Concentration | Exemplary Use |
|---|---|---|
| Hydrocortisone acetate | 1% | Steroid responsive inflammation and psoriasis or atopic dermatitis |
| Betamethasone valerate | 0.1% | |
| Clobetasol proprionate | 0.05% | |
| Acyclovir | 5% | Viral infection, herpes |

TABLE 2-continued

Exemplary Concentrations of Examples of Active Agents

| Class | Concentration | Exemplary Use |
|---|---|---|
| Ciclopirox | 1% | Fungal infection, seborrhea, dandruff, |
| Clindomycin | 2% | Bacterial infection, acne, rosacea, |
| Azelaic acid | 15% | Acne, rosacea, pigmentation disorder and various dermatoses |
| Metronidazol | 0.25%–2% | Rosacea, bacterial infections and parasite infestations |
| Diclofenac | 1% | Osteoarthritus, joint pain |
| Tachrolimus | 0.2% | Atopic dermatitis, eczema and inflammation |

The above examples represent different drug classes and it is to be understood that other drugs belonging to each of the classes represented above may be included and used in the compositions of the present invention in a safe and effective amount.

What is claimed is:

1. A foamable pharmaceutical vehicle or composition, comprising:
   (1) a liquid organic carrier, at a concentration of 10% to 70% by weight of the composition, wherein said organic carrier concurrently comprises:
      (i) at least one hydrophobic organic carrier comprising a triglyceride, and
      (ii) at least one polar solvent comprising dimethyl isosorbide,
   (2) a surface-active agent selected from the group consisting of at least one non-ionic surface-active agent, and a mixture of a non-ionic surface-active agent and an ionic surface-active agent, wherein the ratio of non-ionic surface-active agent to ionic surface-active agent is greater than 14:1;
   (3) water;
   (4) at least one liquefied or compressed gas propellant at a concentration of 3% to 25% by weight of the total composition; and
   (5) a polymeric agent selected from the group consisting of a locust bean gum, sodium caseinate, an egg albumin, a gelatin agar, a carrageenin gum, sodium alginate, a xanthan gum, a quince seed extract, a tragacanth gum, a guar gum, a starch, a chemically modified starch, a cellulose ether, an alkyl cellulose, a hydroxyalkyl cellulose, a hydroxyethyl cellulose, a hydroxypropyl cellulose, a methyl cellulose, a carboxymethyl cellulose, a methylhydroxyethylcellulose, a methylhydroxypropylcellulose, a hydroxypropylmethyl cellulose, a hydroxyethylcarboxymethylcellulose, a carboxymethylhydroxyethylcellulose, a hydroxypropyl guar gum, a soluble starch, a carboxyvinyl polymer, a polyvinylpyrrolidone, a polyvinyl alcohol, a polyacrylic acid polymer, a polymethacrylic acid polymer, a polyvinyl acetate polymer, a polyvinyl chloride polymer, a polyvinylidene chloride polymer, an acrylic acid/ethyl acrylate copolymer, a carboxyvinyl polymer, a silicone dioxide, a poly(acrylic)acid, a poly(methylvinyl ether/maleic anhydride) copolymer, a chitosan, an alginic acid, a hyaluronic acid, a pectin, a karaya gum, a cyclodextrin, a chemically modified cyclodextrin, hydroxypropyl-β-cyclodextrin, a poly(N-isopropylamide), a poloxamer, and mixtures of any two or more thereof; and wherein the composition is provided in an aerosol container and upon release expands to form a breakable foam that collapses upon application of shear force.

2. The composition of claim 1, wherein the surface active agent is 0.1% to 5% by weight of the composition.

3. The composition of claim 1 or 2, wherein the ratio of the hydrophobic organic carrier and the polar solvent are selected to provide a selected pharmacological or safety property.

4. The composition of claim 1, wherein the polymeric agent is 0.01% to 5% by weight of the composition.

5. The composition of claim 1, wherein the polymeric agent is 0.01% to 1% by weight of the composition.

6. The composition of claim 1, further comprising 0.1% to 5% by weight of the composition of a therapeutically active foam adjuvant selected from the group consisting of a fatty alcohol having 15 or more carbons in their carbon chain; a fatty acid having 16 or more carbons in their carbon chain; fatty alcohols derived from beeswax and including a mixture of alcohols, a majority of which has at least 20 carbon atoms in their carbon chain; a fatty alcohol having an double bond; a fatty acid having an double bond; a branched fatty alcohol; a branched fatty acid; a fatty acid substituted with a hydroxyl group; cetyl alcohol; stearyl alcohol; arachidyl alcohol; behenyl alcohol; 1-triacontanol; hexadecanoic acid; stearic acid; arachidic acid; behenic acid; octacosanoic acid; 12-hydroxy stearic acid; and a mixture of any two or more thereof.

7. The composition of claim 1, wherein the polar solvent is soluble in both water and oil.

8. The composition of claim 1, wherein the hydrophobic organic carrier is a liquid at ambient temperature, and has a solubility in distilled water at ambient temperature selected from:
   (i) less than 1 gm per 100 mL;
   (ii) less than 0.5 gm per 100 mL; and
   (iii) less than 0.1 gm per 100 mL.

9. The composition of claim 1, wherein the foamable composition is an emulsion or a micro emulsion selected from the group consisting of an oil-in-water emulsion and a water-in-oil emulsion.

10. The composition of claim 1, wherein upon release from the container, a foam having a density range selected from (1) between 0.02 gr/mL and 0.1 gr/mL; and (2) between 0.04 gr/mL and 0.23 gr/mL is produced.

11. The composition of claim 1, wherein the triglyceride is capric-caprylic triglyceride.

12. The composition of claim 1, further comprising an active agent.

13. The composition of claim 12, wherein the active agent is selected from the group consisting of an anti-infective agent, an antibiotic agent, an antibacterial agent, an antifungal agent, an antiviral agent, an antiparasitic agent, a steroidal anti-inflamatory agent, a nonsteroidal anti-inflammatory agent, an immunosuppressive agent, an immunomodulator, an immunoregulating agent, a hormonal agent, a steroid, a vasoactive agent, a vasoconstructor, a vasodilator, vitamin A, a vitamin A derivative, a retinoid, vitamin B, a vitamin B derivative, vitamin C, a vitamin C derivative, vitamin D, a vitamin D derivative, vitamin E, a vitamin E derivative, vitamin F, a vitamin F derivative, vitamin K, a vitamin K derivative, a wound healing agent, a burn healing agent, an antiallergic agent, a dicarboxylic acid, azelaic acid, sebacic acid, adipic acid, fumaric acid, a retinoid, and a mixture of any two or more thereof at any proportion.

14. The composition of claim 1, further comprising an active agent, selected from the group consisting of a nonsteroidal anti-inflammatory drug, an immunosuppressive agent, an immunomodulator, an immunoregulating agent, a hormonal agent, a steroid, a steroidal anti-inflammatory agent, vitamin A, a vitamin A derivative, vitamin D, a vitamin D derivative, and a mixture of any two or more thereof.

15. The composition of claim 12, wherein the active agent comprises an extract or tincture comprising one or more beneficial agents selected from the group consisting of a hyularonic acid, a herbal extract, coal tar, and a mixture of any two or more thereof.

16. The composition of claim 12, wherein the active agent comprises one or more herbal extracts.

17. The composition of claim 16, wherein the herbal extract is selected from the group consisting of angelica, calendula, celery, coltsfoot, comfrey, dandelion, jamaica dogwood, kava, marshmallow, prickly ash, northern prickly ash, southern senna, valerian, agrimony, aloe vera, alfalfa, artichoke, avens, bayberry, bloodroot, blue flag, bogbean, boldo, boneset, broom, buchu, burdock, burnet, calamus, calendula, cascara, centaury, cereus, chamomile, german chamomile, roman chamomile, cinnamon, divers, cohosh, black, cohosh, blue, cola, corn silk, couchgrass, cowslip, damiana, devil's claw, drosera, echinacea, elder, elecampane, euphorbia, eyebright, figwort, frangula, fucus, fumitory, garlic, golden seal, gravel root, ground ivy, guaiacum, hawthorn, holy thistle, hops, horehound black, horehound white, horse chestnut hydrangea, ispaghula, juniper, lady's lipper, liferoot, lime flower, liquorice, lobelia, mate, meadowsweet, mistletoe, motherwort, myrrh, nettle, parsley, parsley piert, passionflower, pennyroyal, pilewort, plantain, pleurisy root, pokeroot, poplar, pulsatilla, queen's delight, raspberry, red clover, rosemary, sage, sarsaparilla, sassafras, scullcap, senega, shepherd's purse, skunk cabbage, slippery elm, squill, St. john's wort, stone root, tansy, thyme, uva-ursi, vervain, wild carrot, wild lettuce, willow, witch hazel, yarrow, yellow dock, and a mixture of any two or more thereof.

18. The composition of claim 16, wherein the herbal extract comprises a polar solvent.

19. The composition of claim 12, wherein the active agent is selected from the group consisting of a therapeutically effective amount of a solvent, a surface active agent, a foam adjuvant, a gelling agent, and a mixture of any two or more thereof.

20. A method of treating or alleviating a disorder selected from the group consisting of acne, an infection, an inflammation, psoriasis, and rosacea, comprising:
   administering topically to a surface having the disorder, a foamed composition obtained from a canister comprising a foamable composition comprising:
   (1) a liquid organic carrier, at a concentration of 10% to 70% by weight of the foamable composition, wherein said organic carrier concurrently comprises:
      i. at least one hydrophobic organic carrier comprising a triglyceride, and
      ii. at least one polar solvent comprising dimethyl isosorbide;
   (2) 0.1% to 5% by weight of the foamable composition of a surface-active agent selected from the group consisting of at least one non-ionic surface-active agent, and a mixture of a non-ionic surface-active agent and an ionic surface-active agent, wherein the ratio of non-ionic surface-active agent to ionic surface-active agent is greater than 14:1;
   (3) water;
   (4) at least one liquefied or compressed gas propellant at a concentration of 3% to 25% by weight of the total composition;
   (5) a polymeric agent selected from the group consisting of a locust bean gum, sodium caseinate, an egg albumin, a gelatin agar, a carrageenin gum, sodium alginate, a xanthan gum, a quince seed extract, a tragacanth gum, a guar gum, a starch, a chemically modified starch, a cellulose ether, an alkyl cellulose, a hydroxyalkyl cellulose, a hydroxyethyl cellulose, a hydroxypropyl cellulose, a methyl cellulose, a carboxymethyl cellulose, a methylhydroxyethylcellulose, a methylhydroxypropylcellulose, a hydroxypropylmethyl cellulose, a hydroxyethylcarboxymethylcellulose, a carboxymethylhydroxyethylcellulose, a hydroxypropyl guar gum, a soluble starch, a carboxyvinyl polymer, a polyvinylpyrolidone, a polyvinyl alcohol, a polyacrylic acid polymer, a polymethacrylic acid polymer, a polyvinyl acetate polymer, a polyvinyl chloride polymer, a polyvinylidene chloride polymer, an acrylic acid/ethyl acrylate copolymer, a carboxyvinyl polymer, a silicone dioxide, a poly(acrylic)acid, a poly(methylvinyl ether/maleic anhydride) copolymer, a chitosan, an alginic acid, a hyaluronic acid, a pectin, a karaya gum, a cyclodextrin, a chemically modified cyclodextrin, hydroxypropyl-$\beta$-cyclodextrin, a poly(N-isopropylamide), a poloxamer, and mixtures of any two or more thereof; and
   (6) an active agent; and
   wherein the composition is provided in an aerosol container and upon release expands to form a breakable foam that collapses upon application of shear force.

21. The method of claim 20, wherein the composition further includes 0.1% to 5% by weight of the foamable composition of a therapeutically active foam adjuvant is selected from the group consisting of a fatty alcohol having 15 or more carbons in their carbon chain; a fatty acid having 16 or more carbons in their carbon chain; fatty alcohols derived from beeswax and including a mixture of alcohols, a majority of which has at least 20 carbon atoms in their carbon chain; a fatty alcohol having an double bond; a fatty acid having an double bond; a branched fatty alcohol; a branched fatty acid; a fatty acid substituted with a hydroxyl group; cetyl alcohol; stearyl alcohol; arachidyl alcohol; behenyl alcohol; 1-triacontanol; hexadecanoic acid; stearic acid; arachidic acid; behenic acid; octacosanoic acid; 12-hydroxy stearic acid; and a mixture of any two or more thereof.

22. The method of claim 20, wherein the concentration of the polymeric agent is 0.01% to 5% by weight of the foamable composition.

23. The method of claim 20, wherein the surface active agent HLB or the weighted average of the HLB values in the composition is about 9 to about 14.

24. The method of claim 20, wherein the active agent is selected from the group consisting of an anti-infective agent, an antibiotic agent, an antibacterial agent, an antifungal agent, an antiviral agent, an antiparasitic agent, a steroid anti-inflammatory agent, a nonsteroidal anti-inflammatory drug, an immunosuppressive agent, an immunomodulator, an immunoregulating agent, a hormonal agent, a steroid, a vasoactive agent, a vasoconstrictor, a vasodilator, vitamin A, a vitamin A derivative, a retinoid, vitamin B, a vitamin B derivative, vitamin C, a vitamin C derivative, vitamin D, a vitamin D derivative, vitamin E, a vitamin E derivative, vitamin F, a vitamin F derivative, vitamin K, a vitamin K derivative, a wound healing agent, a burn healing agent, an antiallergic agent, a dicarboxylic acid, azelaic acid, sebacic acid, adipic acid, fumaric acid, and a mixture of any two or more thereof at any proportion.

25. The method of claim 20, wherein the foamable composition further comprises at least one active agent selected from the group consisting of a non-steroidal anti-inflammatory drug, an immunosuppressive agent, an immunomodulator, an immunoregulating agent, a hormonal agent, a steroid, a steroidal anti-inflammatory agent, vitamin A, a vitamin A derivative, vitamin D, a vitamin D derivative, and a mixture of any two or more thereof.

26. The method of claim 20, wherein the active agent comprises an extract or tincture comprising one or more beneficial agents selected from the group consisting of a hyularonic acid, a herbal extract, coal tar, and a mixture of any two or more thereof.

27. The method of claim 20, wherein the active agent comprises one or more herbal extracts.

28. The method of claim 27, wherein the herbal extract is selected from the group consisting of angelica, calendula, celery, coltsfoot, comfrey, dandelion, jamaica dogwood, kava, marshmallow, prickly ash, northern prickly ash, southern senna, valerian, agrimony, aloe vera, alfalfa, artichoke, avens, bayberry, bloodroot, blue flag, bogbean, boldo, boneset, broom, buchu, burdock, burnet, calamus, calendula, cascara, centaury, cereus, chamomile, german chamomile, roman chamomile, cinnamon, divers, cohosh, black, cohosh, blue, cola, corn silk, couchgrass, cowslip, damiana, devil's claw, drosera, echinacea, elder, elecampane, euphorbia, eyebright, figwort, frangula, fucus, fumitory, garlic, golden seal, gravel root, ground ivy, guaiacum, hawthorn, holy thistle, hops, horehound black, horehound white, horse chestnut hydrangea, ispaghula, juniper, lady's lipper, liferoot, lime flower, liquorice, lobelia, mate, meadowsweet, mistletoe, motherwort, myrrh, nettle, parsley, parsley piert, passionflower, pennyroyal, pilewort, plantain, pleurisy root, pokeroot, poplar, pulsatilla, queen's delight, raspberry, red clover, rosemary, sage, sarsaparilla, sassafras, scullcap, senega, shepherd's purse, skunk cabbage, slippery elm, squill, St. john's wort, stone root, tansy, thyme, uva-ursi, vervain, wild carrot, wild lettuce, willow, witch hazel, yarrow, yellow dock, and a mixture of any two or more thereof.

29. The method of claim 27, wherein the herbal extract comprises a polar solvent.

30. A non-flammable foamable pharmaceutical composition comprising:
   (1) a liquid organic carrier, at a concentration of 10% to 70% by weight of the pharmaceutical composition, wherein said organic carrier contains at least one member selected from the group consisting of:
      (i) at least one hydrophobic organic carrier comprising a triglyceride, and
      (ii) at least one polar solvent comprising dimethyl isosorbide and a diol;
   (2) a surface-active agent selected from the group consisting of at least one non-ionic surface-active agent, and a mixture of a non-ionic surface-active agent and an ionic surface-active agent, wherein the ratio of non-ionic surface-active agent to ionic surface-active agent is greater than 14:1;
   (3) water;
   (4) at least one hydrofluorocarbon propellant at a concentration of 3% to 25% by weight of the total composition; and
   (5) a polymeric agent selected from the group consisting of a locust bean gum, sodium caseinate, an egg albumin, a gelatin agar, a carrageenin gum, sodium alginate, a xanthan gum, a quince seed extract, a tragacanth gum, a guar gum, a starch, a chemically modified starch, a cellulose ether, an alkyl cellulose, a hydroxyalkyl cellulose, a hydroxyethyl cellulose, a hydroxypropyl cellulose, a methyl cellulose, a carboxymethyl cellulose, a methylhydroxyethylcellulose, a methylhydroxypropylcellulose, a hydroxypropylmethyl cellulose, a hydroxyethylcarboxymethylcellulose, a carboxymethylhydroxyethylcellulose, a hydroxypropyl guar gum, a soluble starch, a carboxyvinyl polymer, a polyvinylpyrrolidone, a polyvinyl alcohol, a polyacrylic acid polymer, a polymethacrylic acid polymer, a polyvinyl acetate polymer, a polyvinyl chloride polymer, a polyvinylidene chloride polymer, an acrylic acid/ethyl acrylate copolymer, a carboxyvinyl polymer, a silicone dioxide, a poly(acrylic)acid, a poly(methylvinyl ether/maleic anhydride) copolymer, a chitosan, an alginic acid, a hyaluronic acid, a pectin, a karaya gum, a cyclodextrin, a chemically modified cyclodextrin, hydroxypropyl-β-cyclodextrin, a poly(N-isopropylamide), a poloxamer, and mixtures of any two or more thereof; and
   wherein the composition is provided in an aerosol container and upon release expands to form a breakable foam that collapses upon application of shear force.

31. The composition of claim 30, further comprising 0.1% to 5% by weight of the pharmaceutical composition of a therapeutically active foam adjuvant is selected from the group consisting of a fatty alcohol having 15 or more carbons in their carbon chain; a fatty acid having 16 or more carbons in their carbon chain; fatty alcohols derived from beeswax and including a mixture of alcohols, a majority of which has at least 20 carbon atoms in their carbon chain; a fatty alcohol having an double bond; a fatty acid having an double bond; a branched fatty alcohol; a branched fatty acid; a fatty acid substituted with a hydroxyl group; cetyl alcohol; stearyl alcohol; arachidyl alcohol; behenyl alcohol; 1-triacontanol; hexadecanoic acid; stearic acid; arachidic acid; behenic acid; octacosanoic acid; 12-hydroxy stearic acid; and a mixture of any two or more thereof.

32. The composition of claim 31, wherein the concentration of the polymeric agent is 0.01% to 5% by weight of the pharmaceutical composition.

33. A composition of any of claim 1, 12, 13, 14, 15, 16, 17, or 18, further comprising an antibiotic, a coal tar, a dicarboxylic acid, or a steroid.

34. The composition of any of claim 12, 13, 14, 15, 16, 17, or 18, wherein the composition provides increased solubility of the active or beneficial agent.

35. The composition of any of claim 12, 13, 14, 15, 16, 17, or 18, wherein the composition provides increased delivery of the active or beneficial agent.

36. The composition of any of claim 1, 12, 13, 14, 15, 16, 17, or 18, wherein the composition provides enhanced skin barrier build up.

37. The composition of any of claim 12, 13, 14, 15, 16, 17, or 18, wherein the composition provides increased penetration of the active agent.

38. The composition of claim 16, wherein the at least one polar solvent comprises a polar solvent component of the liquid organic carrier and a polar solvent component of the extracts.

39. The composition of claim 13, wherein the polar solvent further comprises propylene glycol; wherein the triglyceride comprises capric-caprylic triglycerides; wherein the surface-active agent comprises glyceryl stearate, PEG-40 stearate, polysorbate 80, or any mixtures of two or more thereof; wherein the polymeric agent comprises a xanthan gum, a methyl cellulose, or mixtures thereof; and wherein the composition further comprises a foam adjuvant comprising a cetostearyl alcohol.

40. The composition of claim 30, wherein the polar solvent further comprises propylene glycol; wherein the triglyceride comprises capric-caprylic triglycerides; wherein the surface-active agent comprises glyceryl stearate, PEG-40 stearate, polysorbate 80, or any mixtures of two or more thereof; wherein the polymeric agent comprises a xanthan gum, a methyl cellulose, or mixtures thereof; and wherein the composition further comprises a foam adjuvant comprising a cetostearyl alcohol.

41. The method of claim 24, wherein the polar solvent further comprises propylene glycol; wherein the triglyceride comprises capric-caprylic triglycerides; wherein the surface-active agent comprises glyceryl stearate, PEG-40 stearate, polysorbate 80, or any mixtures of two or more thereof; wherein the polymeric agent comprises a xanthan gum, a methyl cellulose, or mixtures thereof; and wherein the composition further comprises a foam adjuvant comprising a cetostearyl alcohol.

42. The composition of claim 12, wherein the active agent is azelaic acid.

43. The composition of claim 42, wherein the surface active agent is 0.1% to 5% by weight of the composition.

44. The composition of claim 42, wherein the polymeric agent is 0.01% to 5% by weight of the composition.

45. The composition of claim 42, wherein the polymeric agent is 0.01% to 1% by weight of the composition.

46. The composition of claim 42, further comprising 0.1% to 5% by weight of the composition of a therapeutically active foam adjuvant selected from the group consisting of a fatty alcohol having 15 or more carbons in their carbon chain; a fatty acid having 16 or more carbons in their carbon chain; fatty alcohols derived from beeswax and including a mixture of alcohols, a majority of which has at least 20 carbon atoms in their carbon chain; a fatty alcohol having an double bond; a fatty acid having an double bond; a branched fatty alcohol; a branched fatty acid; a fatty acid substituted with a hydroxyl group; cetyl alcohol; stearyl alcohol; arachidyl alcohol; behenyl alcohol; 1-triacontanol; hexadecanoic acid; stearic acid; arachidic acid; behenic acid; octacosanoic acid; 12-hydroxy stearic acid; and a mixture of any two or more thereof.

47. The composition of claim 42, wherein the triglyceride is capric-caprylic triglyceride.

48. The method of claim 20, wherein the active agent is azelaic acid.

49. The method of claim 48, wherein the surface active agent is 0.1% to 5% by weight of the composition.

50. The method of claim 48, wherein the polymeric agent is 0.01% to 5% by weight of the composition.

51. The method of claim 48, wherein the polymeric agent is 0.01% to 1% by weight of the composition.

52. The method of claim 48, further comprising 0.1% to 5% by weight of the composition of a therapeutically active foam adjuvant selected from the group consisting of a fatty alcohol having 15 or more carbons in their carbon chain; a fatty acid having 16 or more carbons in their carbon chain; fatty alcohols derived from beeswax and including a mixture of alcohols, a majority of which has at least 20 carbon atoms in their carbon chain; a fatty alcohol having an double bond; a fatty acid having an double bond; a branched fatty alcohol; a branched fatty acid; a fatty acid substituted with a hydroxyl group; cetyl alcohol; stearyl alcohol; arachidyl alcohol; behenyl alcohol; 1-triacontanol; hexadecanoic acid; stearic acid; arachidic acid; behenic acid; octacosanoic acid; 12-hydroxy stearic acid; and a mixture of any two or more thereof.

53. The method of claim 48, wherein the triglyceride is capric-caprylic triglyceride.

54. The composition of claim 12, wherein the active agent comprises an anti-oxidant, a radical scavenger or mixtures thereof.

55. The composition of claim 54, wherein the composition further comprises a foam adjuvant comprising behenyl alcohol.

56. The method of claim 20, wherein the active agent comprises an anti-oxidant, a radical scavenger, or mixtures thereof.

57. The method of claim 56, wherein the composition further comprises a foam adjuvant comprising behenyl alcohol.

58. The composition of claim 12, further comprising a humectant, a film forming agent, or mixtures thereof.

59. The composition of claim 40, further comprising an active agent.

60. The composition of claim 59, wherein the propylene glycol is about 10% to about 20% by weight of the composition; wherein the dimethyl isosorbide is about 5% to about 10% by weight of the composition; wherein the capric-caprylic triglycerides is about 10% to about 20% by weight of the composition; wherein the surface-active agent comprises about 0.1% to about 5% by weight of the composition of glyceryl stearate, PEG-40 stearate, polysorbate 80, or mixtures of any two or more thereof; wherein the polymeric agent comprises about 0.01% to about 5% by weight of the composition of a xanthan gum, a methyl cellulose, or mixtures thereof; and wherein the cetostearyl alcohol is about 0.4% to about 2.5% by weight of the composition.

61. The composition of claim 60, further comprising a humectant, a film forming agent, or mixtures thereof.

62. The composition of claim 39, wherein the hydrophobic organic carrier is in an amount of about 10% to about 20% by weight of the composition, or about 20% to about 50% by weight of the composition.

63. The composition of claim 39, wherein the ratio between the polar solvent and the hydrophobic organic carrier is selected from the group consisting of between about 1:4 and about 4:1, between about 1:1 and about 4:1, between about 2:8 and about 1:1, about 1:4, about 1:2, about 3:4, about 1:1, about 5:4, about 4:2, about 3:1, about 4:1, about 6:4, and about 7:4.

64. The composition of claim 62, wherein the surface-active agent is less than about 2% or less than about 1% by weight of the composition.

65. The composition of claim 39, wherein the propylene glycol is about 10% to about 20% by weight of the composition; wherein the dimethyl isosorbide is about 5% to about 10% by weight of the composition; wherein the capric-caprylic triglycerides is about 10% to about 20% by weight of the composition; wherein the surface-active agent comprises about 0.1% to about 5% by weight of the composition of glyceryl stearate, PEG-40 stearate, polysorbate 80, or mixtures of any two or more thereof; wherein the polymeric agent comprises about 0.01% to about 5% by weight of the composition of a xanthan gum, a methyl cellulose, or mixtures thereof; and wherein the cetostearyl alcohol is about 0.4% to about 2.5% by weight of the composition.

66. The composition of claim 13, further comprising a humectant, an emollient, or a mixture thereof, wherein the emollient is selected from the group consisting of isopropyl myristate, isopropyl palmitate, isopropyl isostearate, diisopropyl adipate, diisopropyl dimerate, maleated soybean oil, octyl palmitate, cetyl lactate, cetyl ricinoleate, tocopheryl acetate, cetyl acetate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, isononyl isononanoate, isotridecyl isononanoate, myristyl myristate, octyl dodecanol, sucrose esters of fatty acids, octyl hydroxystearate and mixtures of any two or more thereof; and wherein upon release from a pressurized container, the composition expands to form a foam that collapses upon application of shear force but does not immediately collapse upon exposure to skin temperature.

67. The method of claim 27, wherein the at least one polar solvent comprises a polar solvent component of the liquid organic carrier and a polar solvent component of the extracts.

\* \* \* \* \*

UNITED STATES PATENT AND TRADEMARK OFFICE
CERTIFICATE OF CORRECTION

PATENT NO. : 10,117,812 B2
APPLICATION NO. : 11/488989
DATED : November 6, 2018
INVENTOR(S) : Dov Tamarkin Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1455 days.

Signed and Sealed this
Eighteenth Day of June, 2019

Andrei Iancu
*Director of the United States Patent and Trademark Office*